United States Patent
Solomon et al.

(10) Patent No.: US 9,114,915 B2
(45) Date of Patent: Aug. 25, 2015

(54) DISINFECTING CAPS FOR MEDICAL MALE LUER CONNECTORS

(71) Applicant: Catheter Connections, Inc., Salt Lake City, UT (US)

(72) Inventors: Donald D. Solomon, North Salt Lake, UT (US); F. Mark Ferguson, Salt Lake City, UT (US); Robert Hitchcock, Sandy, UT (US); Steven Bandis, West Jordan, UT (US); James V. Mercer, West Jordan, UT (US); Michael W. Howlett, Salt Lake City, UT (US)

(73) Assignee: Catheter Connections, Inc., Salt Lake City, UT (US)

(*) Notice: Subject to any disclaimer, the term of this patent is extended or adjusted under 35 U.S.C. 154(b) by 0 days.

(21) Appl. No.: 14/277,885

(22) Filed: May 15, 2014

(65) Prior Publication Data

US 2014/0248182 A1    Sep. 4, 2014

Related U.S. Application Data

(60) Continuation of application No. 14/275,296, filed on May 12, 2014, which is a continuation of application No. 14/162,207, filed on Jan. 23, 2014, which is a continuation of application No. 13/736,166, filed on
(Continued)

(51) Int. Cl.
*B65D 41/02* (2006.01)
*A61B 19/00* (2006.01)
*A61M 25/00* (2006.01)
(Continued)

(52) U.S. Cl.
CPC ............... *B65D 41/02* (2013.01); *A61B 19/34* (2013.01); *A61L 2/16* (2013.01); *A61L 2/18* (2013.01); *A61M 25/0097* (2013.01);
(Continued)

(58) Field of Classification Search
CPC ...... A61B 19/34; A61L 2/18; A61L 2202/24; A61M 39/16; A61M 39/162; A61M 39/165; A61M 39/18; A61M 39/20; A61M 2005/3104; B65D 41/02
USPC ................. 604/192, 198, 199, 263, 265, 905; 422/28, 292, 294, 300–302
See application file for complete search history.

(56) References Cited

U.S. PATENT DOCUMENTS

| 2,351,804 A | 6/1944 | Blum ........................ B65D 3/22 |
| 3,446,596 A | 5/1969 | Salivar et al. ............. C12Q 1/10 |

(Continued)

FOREIGN PATENT DOCUMENTS

| EP | 0 462 355 A1 | 12/1991 | ............ A61M 39/00 |
| WO | WO 2006/099306 | 9/2006 | ............ A61M 25/16 |

(Continued)

OTHER PUBLICATIONS

U.S. Appl. No. 13/281,413, filed Oct. 25, 2011, Howlett.
(Continued)

*Primary Examiner* — Kami A Bosworth
(74) *Attorney, Agent, or Firm* — Sunstein Kann Murphy & Timbers LLP

(57) ABSTRACT

Disclosed herein are disinfecting caps that can be used to cover and disinfect both a male medical connector and needleless injection site when not in use or when disconnected from each other. The caps contain a disinfecting agent.

15 Claims, 58 Drawing Sheets

Related U.S. Application Data

Jan. 8, 2013, now Pat. No. 8,641,681, which is a continuation of application No. 13/664,641, filed on Oct. 31, 2012, now Pat. No. 8,647,308, which is a continuation of application No. 13/281,404, filed on Oct. 25, 2011, now Pat. No. 8,328,767, and a continuation of application No. 12/917,336, filed on Nov. 1, 2010, now Pat. No. 8,523,830, said application No. 13/281,404 is a continuation-in-part of application No. 12/610,141, filed on Oct. 30, 2009, now Pat. No. 8,172,825, and a continuation-in-part of application No. 12/610,033, filed on Oct. 30, 2009, now Pat. No. 8,647,326, and a continuation-in-part of application No. 12/171,997, filed on Jul. 11, 2008, now Pat. No. 8,197,749, and a continuation-in-part of application No. 12/164,310, filed on Jun. 30, 2008, now Pat. No. 8,177,761, and a continuation-in-part of application No. 12/014,388, filed on Jan. 15, 2008, now abandoned, said application No. 12/610,141 is a continuation-in-part of application No. 12/014,388, filed on Jan. 15, 2008, now abandoned, said application No. 12/610,033 is a continuation-in-part of application No. 12/014,388, filed on Jan. 15, 2008, now abandoned, said application No. 12/171,997 is a continuation-in-part of application No. 12/014,388, filed on Jan. 15, 2008, now abandoned, said application No. 12/164,310 is a continuation-in-part of application No. 12/014,388, filed on Jan. 15, 2008, now abandoned, application No. 14/277,885, which is a continuation of application No. 13/678,057, filed on Nov. 15, 2012, which is a continuation of application No. 12/956,704, filed on Nov. 30, 2010, now Pat. No. 8,343,112, which is a continuation-in-part of application No. 12/610,141, filed on Oct. 30, 2009, now Pat. No. 8,172,825, and a continuation-in-part of application No. 12/917,336, filed on Nov. 1, 2010, now Pat. No. 8,523,830, application No. 14/277,885, which is a continuation of application No. 13/794,338, filed on Mar. 11, 2013, which is a continuation of application No. 13/564,122, filed on Aug. 1, 2012, now Pat. No. 8,419,713, application No. 14/277,885, which is a continuation of application No. 13/972,101, filed on Aug. 21, 2013, now Pat. No. 8,961,475, which is a division of application No. 12/957,263, filed on Nov. 30, 2010, now Pat. No. 8,523,831, which is a continuation-in-part of application No. 12/610,141, filed on Oct. 30, 2009, now Pat. No. 8,172,825, and a continuation-in-part of application No. 12/917,336, filed on Nov. 1, 2010, now Pat. No. 8,523,830.

(60) Provisional application No. 60/880,541, filed on Jan. 16, 2007, provisional application No. 61/265,207, filed on Nov. 30, 2009, provisional application No. 61/265,216, filed on Nov. 30, 2009.

(51) Int. Cl.
*A61M 39/16* (2006.01)
*A61M 39/20* (2006.01)
*A61L 2/18* (2006.01)
*A61L 2/16* (2006.01)

(52) U.S. Cl.
CPC ............ *A61M 39/162* (2013.01); *A61M 39/20* (2013.01); *A61L 2202/24* (2013.01); *Y10S 604/905* (2013.01)

(56) References Cited

U.S. PATENT DOCUMENTS

| | | |
|---|---|---|
| 3,987,930 A | 10/1976 | Fuson .................. A61M 39/20 |
| 4,232,677 A | 11/1980 | Leibinsohn ............. A61F 5/441 |
| 4,324,239 A | 4/1982 | Gordon et al. ......... A61M 39/26 |
| 4,340,052 A | 7/1982 | Dennehey et al. ...... A61M 3/00 |
| 4,346,703 A | 8/1982 | Dennehey et al. ...... A61J 1/100 |
| 4,354,490 A | 10/1982 | Rogers .................. A61M 1/28 |
| 4,369,781 A | 1/1983 | Gilson et al. ........... A61M 5/34 |
| 4,402,691 A | 9/1983 | Rosenthal et al. ..... A61M 39/16 |
| 4,432,764 A | 2/1984 | Lopez ..................... A61M 1/28 |
| 4,432,766 A | 2/1984 | Bellotti et al. ......... A61M 39/16 |
| 4,440,207 A | 4/1984 | Genatempo et al. .... A61L 31/16 |
| 4,450,624 A | 5/1984 | Collier .................. H01R 43/20 |
| 4,597,758 A | 7/1986 | Aalto et al. ............ A61M 5/005 |
| 4,624,664 A | 11/1986 | Peluso et al. .................. 604/256 |
| 4,671,306 A | 6/1987 | Spector ............................ 132/73 |
| 4,778,447 A | 10/1988 | Velde et al. ........... A61M 39/10 |
| 4,838,875 A | 6/1989 | Somor ...................... A61J 1/05 |
| 5,184,742 A | 2/1993 | DeCaprio et al. .............. 215/356 |
| 5,205,821 A | 4/1993 | Kruger et al. ......... A61M 39/00 |
| 5,242,425 A | 9/1993 | White et al. .......... A61M 5/158 |
| 5,466,219 A | 11/1995 | Lynn et al. ............... A61B 5/15 |
| 5,554,135 A | 9/1996 | Menyhay .............. A61M 39/16 |
| 5,694,978 A | 12/1997 | Heilmann et al. ....... F16L 57/00 |
| 5,792,120 A | 8/1998 | Menyhay .............. A61M 39/16 |
| 5,894,015 A | 4/1999 | Rechtin .................. A61M 5/00 |
| 5,951,519 A | 9/1999 | Utterberg ............... A61M 39/02 |
| 5,954,957 A | 9/1999 | Chin-Loy et al. ............. 210/232 |
| 6,045,539 A | 4/2000 | Menyhay .............. A61M 29/16 |
| 6,171,287 B1 | 1/2001 | Lynn et al. ............. A61M 5/168 |
| 6,932,795 B2 | 8/2005 | Lopez et al. .......... A61M 39/26 |
| 6,960,191 B2 | 11/2005 | Howlett et al. ........ A61M 25/06 |
| 7,040,598 B2 | 5/2006 | Raybuck .................. F16L 37/28 |
| 7,198,611 B2 | 4/2007 | Connell et al. .......... A61M 1/00 |
| D547,446 S | 7/2007 | Racz et al. |
| D550,355 S | 9/2007 | Racz et al. |
| 7,316,669 B2 | 1/2008 | Ranalletta ............... A61M 5/32 |
| D607,325 S | 1/2010 | Rogers et al. |
| 7,762,524 B2 | 7/2010 | Cawthon et al. ........ F16L 37/28 |
| 7,780,794 B2 | 8/2010 | Rogers et al. ........... B08B 17/04 |
| 7,922,701 B2 | 4/2011 | Buchman ..................... 604/256 |
| 7,985,302 B2 | 7/2011 | Rogers et al. ............. B08B 3/04 |
| 8,172,825 B2 | 5/2012 | Solomon et al. ........ A61M 5/14 |
| 8,177,761 B2 | 5/2012 | Howlett et al. .......... A61M 5/14 |
| 8,197,749 B2 | 6/2012 | Howlett et al. ............. A61L 2/00 |
| 8,231,587 B2 | 7/2012 | Solomon et al. ........ A61M 5/32 |
| 8,328,767 B2 | 12/2012 | Solomon et al. ........ A61M 5/32 |
| 8,343,112 B2 | 1/2013 | Solomon et al. ........ A61M 5/14 |
| 8,419,713 B1 | 4/2013 | Solomon et al. ....... A61M 39/00 |
| 8,523,830 B2 | 9/2013 | Solomon et al. ........ A61M 5/14 |
| 8,523,831 B2 | 9/2013 | Solomon et al. ........ A61M 5/14 |
| 8,641,681 B2 | 2/2014 | Solomon et al. ........ A61M 5/32 |
| 8,647,308 B2 | 2/2014 | Solomon et al. ........ A61M 5/32 |
| 8,647,326 B2 | 2/2014 | Solomon et al. ........ A61M 5/00 |
| 2002/0093192 A1 | 7/2002 | Matkovich ................ A61J 1/05 |
| 2003/0140441 A1 | 7/2003 | Stafford .................. A47L 13/12 |
| 2003/0153865 A1 | 8/2003 | Connell et al. .......... A61M 1/16 |
| 2003/0198502 A1 | 10/2003 | Maloney et al. ........ A61M 9/28 |
| 2004/0201216 A1 | 10/2004 | Segal et al. ............ A61M 39/10 |
| 2004/0214316 A1 | 10/2004 | O'Connell ................ C12M 1/30 |
| 2004/0258560 A1 | 12/2004 | Lake, Jr. et al. ................. 422/28 |
| 2005/0033267 A1 | 2/2005 | Decaria .................... A61J 15/00 |
| 2005/0124970 A1 | 6/2005 | Kunin et al. ........... A61M 39/10 |
| 2005/0147524 A1 | 7/2005 | Bousquet ......................... 422/28 |
| 2005/0183971 A1 | 8/2005 | Petricca ........................ 206/210 |
| 2005/0203460 A1 | 9/2005 | Kim ....................... A61M 39/20 |
| 2005/0245883 A1 | 11/2005 | Baldwin ................ A61M 39/22 |
| 2005/0266714 A1 | 12/2005 | Higgins et al. ......... H01R 13/52 |
| 2006/0030827 A1 | 2/2006 | Raulerson et al. ..... A61M 25/06 |
| 2007/0112333 A1 | 5/2007 | Hoang et al. ........... A61M 39/10 |
| 2007/0202177 A1 | 8/2007 | Hoang ...................... A61K 9/14 |
| 2007/0287989 A1 | 12/2007 | Crawford |
| 2007/0293818 A1 | 12/2007 | Stout et al. ............. A61M 31/00 |
| 2007/0293822 A1 | 12/2007 | Crawford et al. ....... A61M 5/00 |
| 2008/0021381 A1 | 1/2008 | Lurvey et al. ......... A61M 25/00 |
| 2008/0027399 A1 | 1/2008 | Harding et al. ........ A61M 25/00 |

(56) References Cited

U.S. PATENT DOCUMENTS

| | | | |
|---|---|---|---|
| 2008/0038167 A1 | 2/2008 | Lynn | A61L 2/18 |
| 2008/0039803 A1 | 2/2008 | Lynn | A61M 39/16 |
| 2008/0086091 A1 | 4/2008 | Anderson et al. | A61M 5/31 |
| 2008/0095680 A1 | 4/2008 | Steffens et al. | A61L 2/18 |
| 2008/0105704 A1 | 5/2008 | Pritchard | B67D 7/16 |
| 2008/0107564 A1 | 5/2008 | Sternberg et al. | G01N 21/78 |
| 2008/0132880 A1 | 6/2008 | Buchman | A61M 39/02 |
| 2008/0147047 A1 | 6/2008 | Davis et al. | A61M 39/16 |
| 2008/0177250 A1 | 7/2008 | Howlett et al. | A61M 39/16 |
| 2008/0235888 A1 | 10/2008 | Vaillancourt et al. | B08B 9/00 |
| 2009/0008393 A1 | 1/2009 | Howlett et al. | B65D 43/03 |
| 2009/0062766 A1 | 3/2009 | Howlett et al. | A61B 19/02 |
| 2009/0205151 A1 | 8/2009 | Fisher et al. | B08B 1/00 |
| 2010/0047123 A1 | 2/2010 | Solomon et al. | A61L 2/18 |
| 2010/0049170 A1 | 2/2010 | Solomon et al. | A61M 39/00 |
| 2010/0242993 A1 | 9/2010 | Hoang et al. | B08B 7/00 |
| 2010/0306938 A1 | 12/2010 | Rogers et al. | B08B 1/00 |
| 2010/0313366 A1 | 12/2010 | Rogers et al. | B08B 1/00 |
| 2011/0044850 A1 | 2/2011 | Solomon et al. | A61L 2/16 |
| 2011/0165020 A1 | 7/2011 | Tryggvason et al. | 422/28 |
| 2011/0213341 A1 | 9/2011 | Solomon et al. | A61L 2/00 |
| 2011/0217212 A1 | 9/2011 | Solomon et al. | A61L 2/18 |

FOREIGN PATENT DOCUMENTS

| | | | |
|---|---|---|---|
| WO | WO 2008/089196 | 7/2008 | A61M 39/16 |
| WO | WO 2008/100950 | 8/2008 | A61B 19/00 |
| WO | WO 2010/002808 | 1/2010 | F16L 21/00 |
| WO | WO 2010/141508 | 12/2010 | A61L 2/00 |
| WO | WO 2011/053924 | 5/2011 | A61M 5/14 |
| WO | WO 2011/066565 | 6/2011 | A61M 39/00 |
| WO | WO 2011/066586 | 6/2011 | A61M 39/20 |

OTHER PUBLICATIONS

Unomedical Medical Products catalog, circa Jan. 2006, available at www.unomedical.net/au/section10/localssI/..%5Cpdf%5Cmedical.

Tego Connector product brochure, circa Nov. 2008, 2 pages, available at www.icumed.com/Docs-Tego/M1148%20TEGO%2020Folder%20Brochure%20Rev.3.

Ron Stoker, One Less Problem, *Managing Infection Control*, Jun. 2008, 4 pages, available at www.baxa.com/resources/docs/onelesspropaper.com.

Notification of Transmittal of the International Search Report and the Written Opinion of the International Searching Authority issued Aug. 1, 2008 in International Application No. PCT/US2008/051087.

Notification of Transmittal of the International Search Report and the Written Opinion of the International Searching Authority issued Jan. 6, 2011 in International Application No. PCT/US2010/054995.

Notification of Transmittal of the International Search Report and the Written Opinion of the International Searching Authority issued Jan. 26, 2011 in International Application No. PCT/US2010/0548404.

Notification of Transmittal of the International Search Report and the Written Opinion of the International Searching Authority issued Feb. 7, 2011 in International Application No. PCT/US2010/0548453.

International Search Report and Written Opinion for PCT/US2009/049094 dated Aug. 31, 2009.

Maki, Dennis G., In Vitro Studies of a Novel Antimicrobial Luer-Activated Needleless Connector for Prevention of Catheter-Related Bloodstream Infection, *Clinical Infection Diseases*, Jun. 15, 2010, vol. 50, Issue 12, pp. 1580-1587.

Hospira Male/Female Sterile Cap product packaging insert and brochure, circa Aug. 2004, 1 page.

Curos Port Protector web page from http.iveramed.com dated Jul. 11, 2008, 1 page.

Curos Port Protector product brochure, Jul. 11, 2008, www.iveramed.com, 1 page.

Curos Port Protector product brochure, circa Nov. 2008, 2 pages available at www.iveramed.com/docs/curos%20brochure-final.

Braun product catalog, circa Aug. 2008, 2 pages.

BD Q-Syte Luer Access Split Septum product brochure, circa Nov. 2008, 4 pages, available at www.bd.com/infusion/pdfs/D16333.

Baxa Corporation Patlock catalog page, 3 pages, copyright 2009, available at www.baxa.com/searchresults/productdetail/?id=6452BFB9-3048-7B87-701697FB93902BA6.

Baxa Corporation Padlock Set Saver Specifications for Instructions and Use, copyright 2007, 2 pages, available at www.baxa.com/ressources/docs/5300103905C.

Baxa Corporation Padlock product brochure, copyright 2007, 1 page, available at www.baxa.com/resources/docs/5300104405A.

Baxa Corporation Padlock Microbial Testing Paper, copyright 2007, 4 pages, available at www.baxa.com/resources/docs/technicalpapers.padlockmicrobialchallengetechpaper.

Baxa Corporation Launches PadLock Set Saver for IV Safety press release, Oct. 10, 2007, 2 pages, available at www.pr.com/press-release/55432.

Buchman, et al., A New Central Venous Catheter Cap: Decreased Microbial Growth and Risk for Catheter-Related Bloodstream Infection, *The Journal of Vascular Access*, 2009, 10: pp. 11-21.

International Searching Authority, International Search Report—International Application No. PCT/US2009/049094, dated Aug. 31, 2009, together with the Written Opinion of the International Searching Authority, 9 pages.

Ivera Medical Corporation, Curos™ Port Protector, web page from http://www.iveramed.com, dated Jul. 11, 2008, 1 page.

Ivera Medical Corporation, The Curos™ Port Protector. Simply Changing Infection Control Practice, Part No. 3005-1, IMC 005, Nov. 2008, 2 pages.

Ivera Medical Corporation, The Curos® Port Protector. Simply Changing Infection Control. http://www.iveramed.com/curos-port-protector, May 13, 2010, 2 pages.

Extended European Search Report, dated Mar. 6, 2012, Application No./Patent No. 08727689.5-2319/2125074; PCTUS2008051087, 7 pages.

The KippGroup, Kippmed Vented and Non-Vented Female Luer Lock Caps. The KippGroup, Jan. 1995, 2 pages.

Leinsing, Karl R., Declaration of Karl R. Leinsing, MSME, PE in Support of Defendant Ivera Medical Corporation's Memorandum in Opposition to Catheter Connections Motion for Preliminary Injunction. U.S.D.C. C.Utah, Civil Action No. 2:14-CV-00070, Mar. 12, 2014.

Burton, H. Dickson, Catheter Connections's Reply Memorandum in Support of its Motion for Preliminary Injunction (Redacted-Nonconfidential Version). U.S.D.C. C.Utah, Civil Action No. 2:14-CV-00070, Apr. 2, 2014, 254 pages.

Nathan D. Thomas, Ivera's Memorandum in Opposition to Plaintiff's Motion for Preliminary Injunction (Redacted-Nonconfidential Version). U.S.D.C. C.Utah, Civil Action No. 2:14-CV-00070, Mar. 12, 2014, 94 pages.

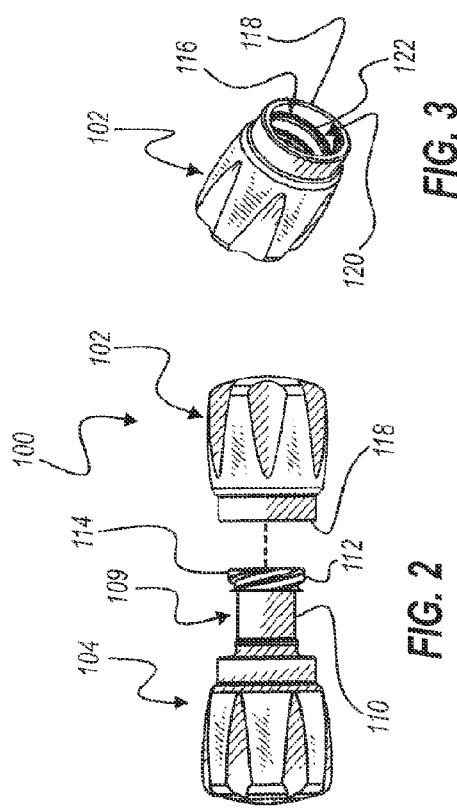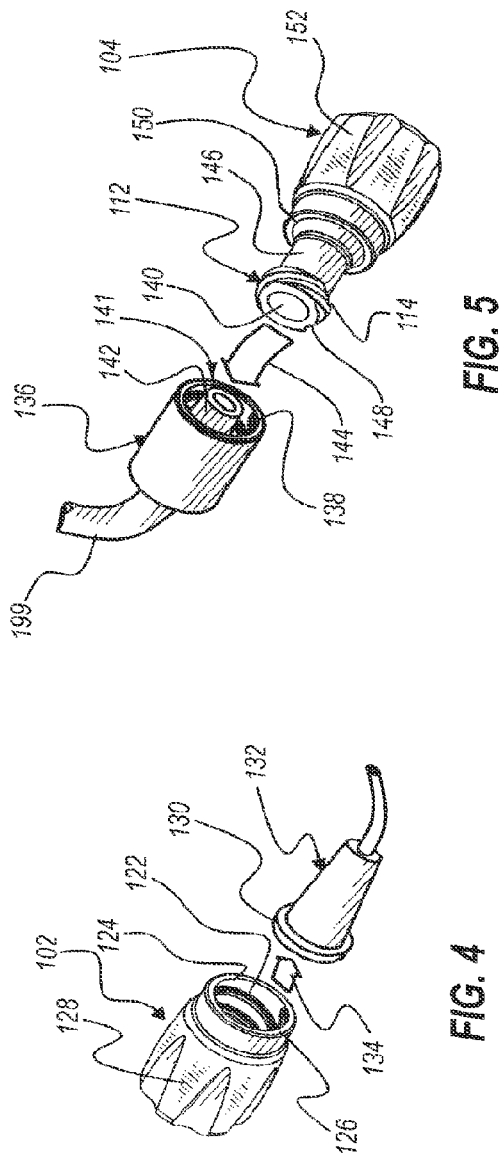

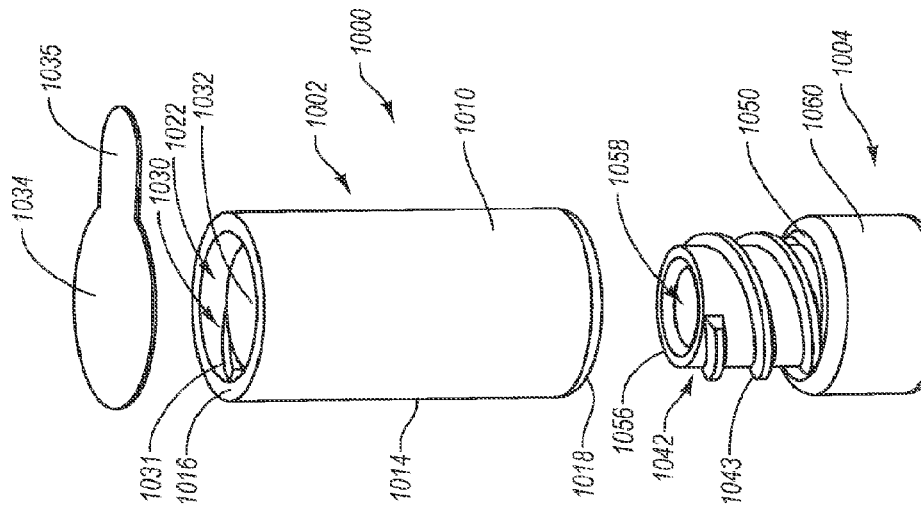
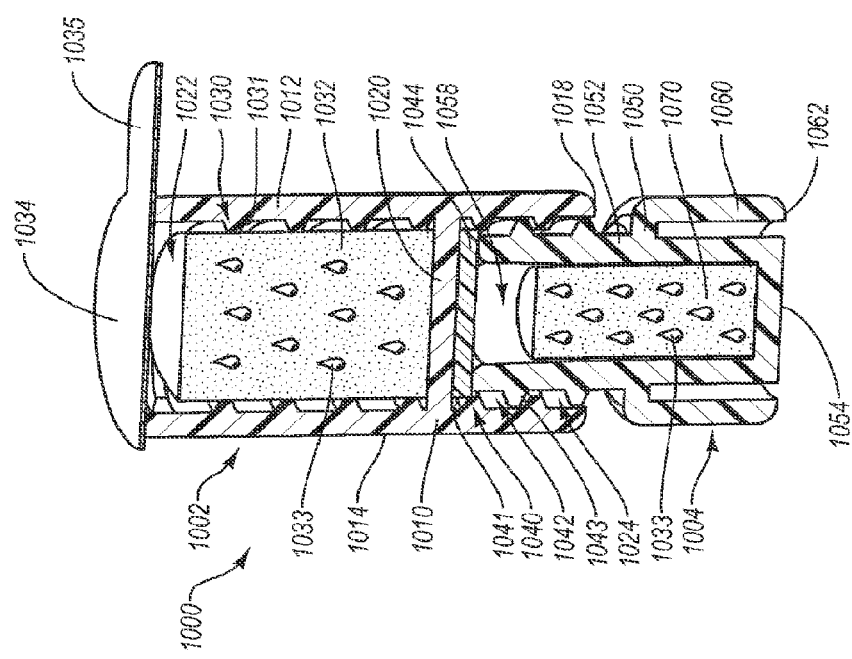

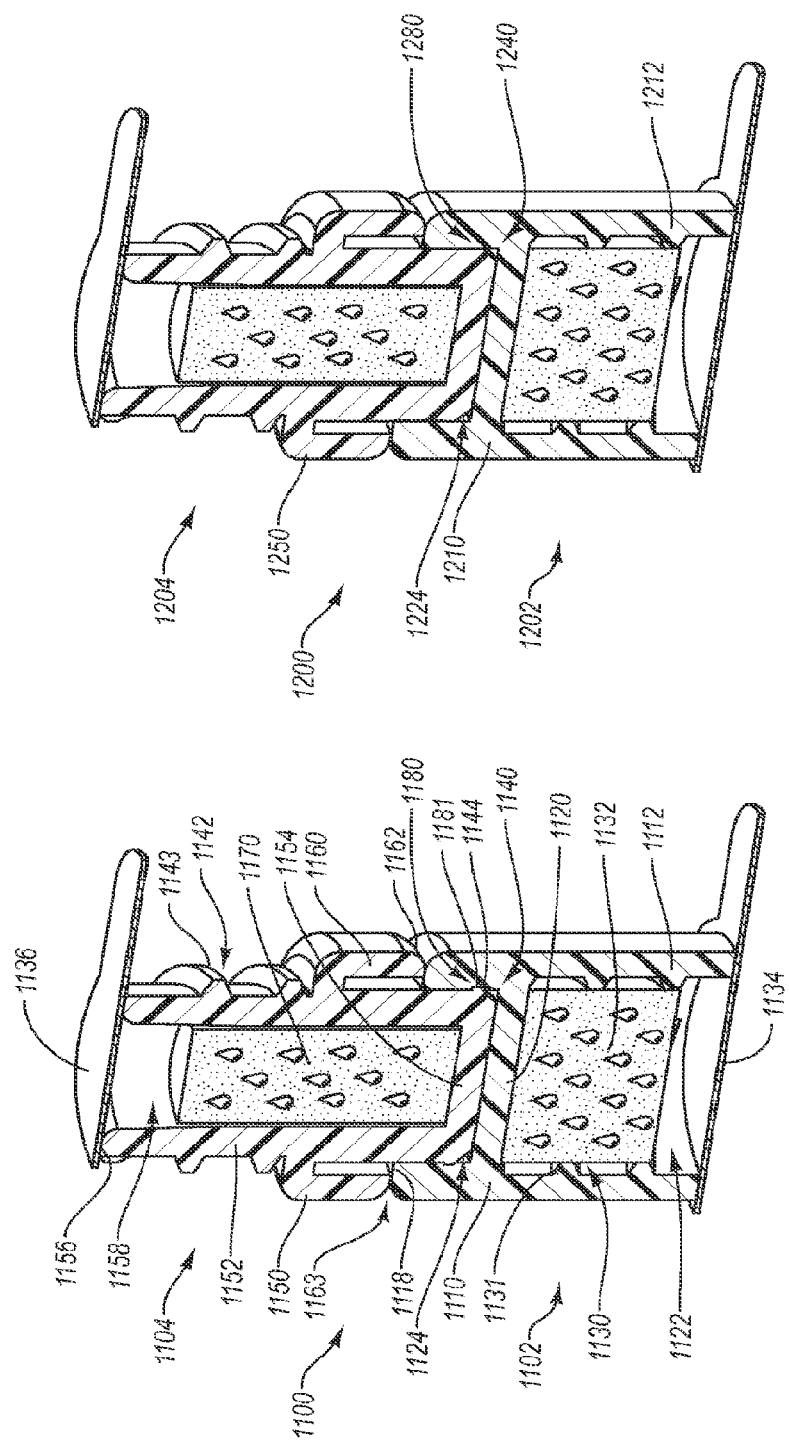

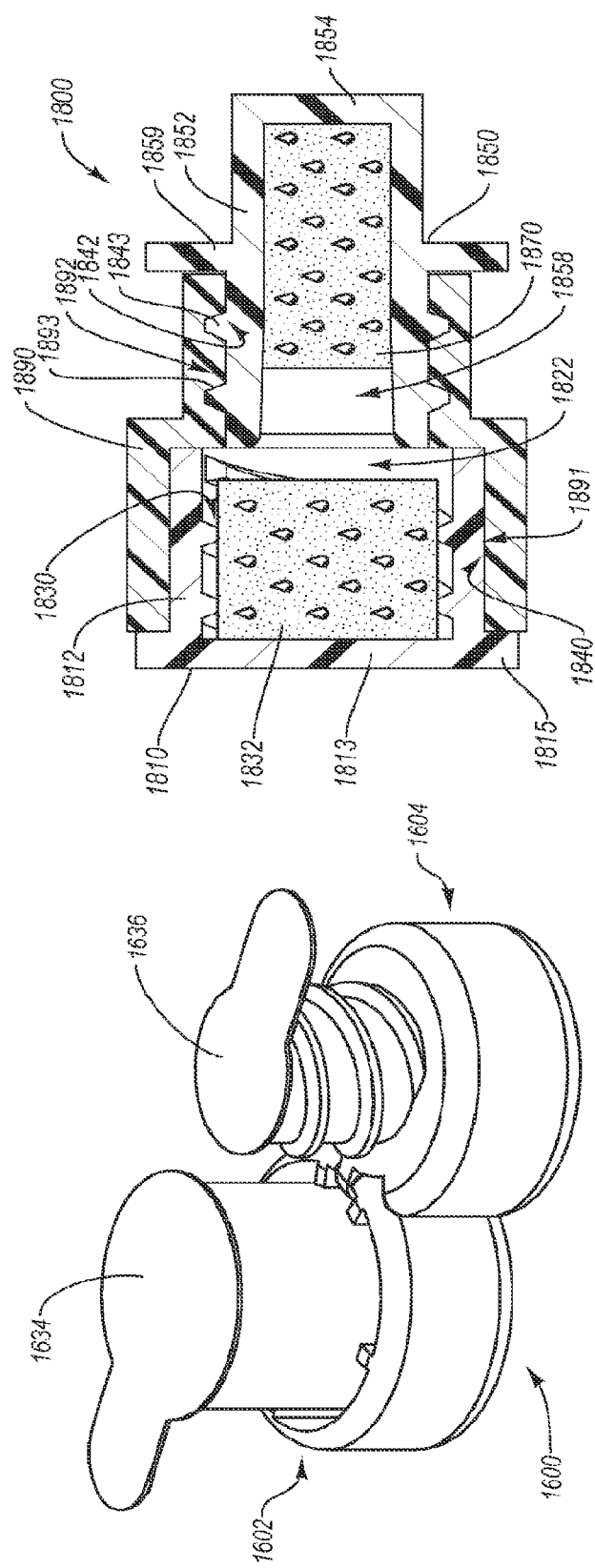

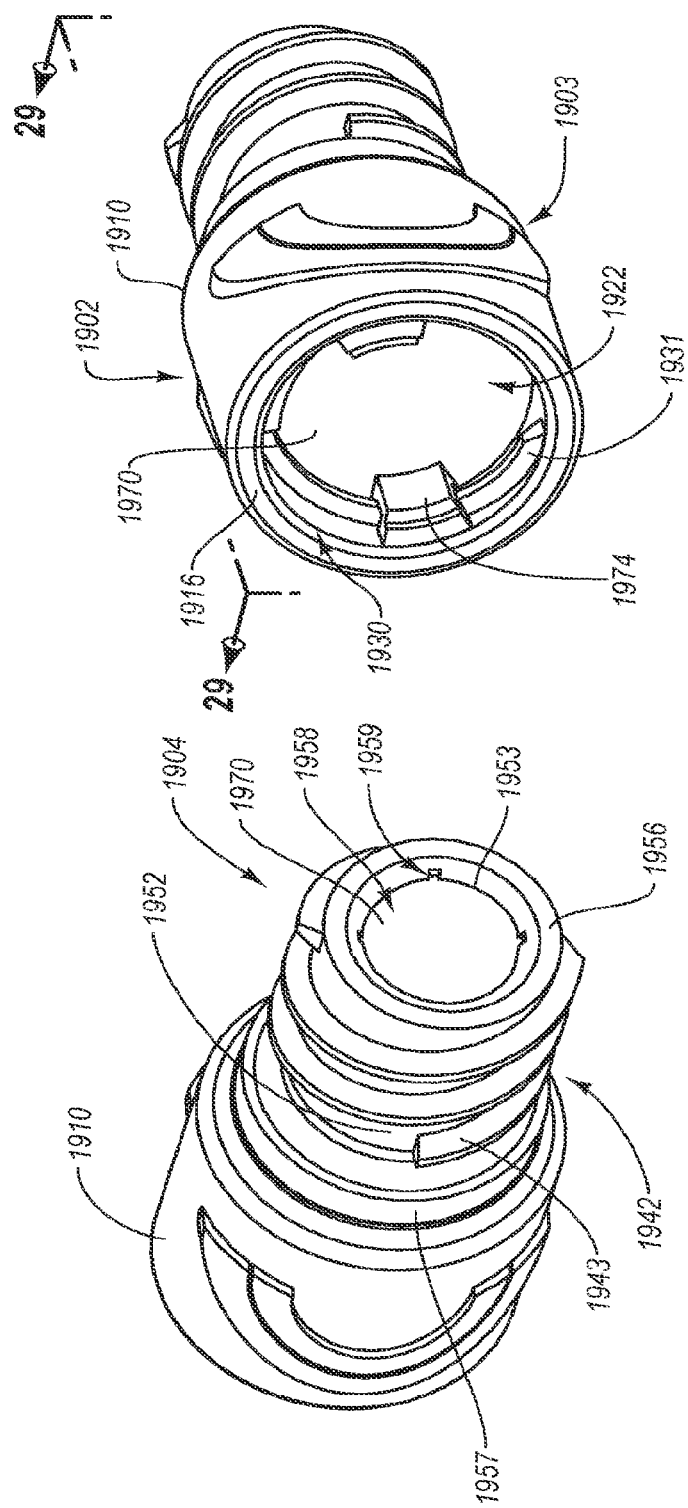

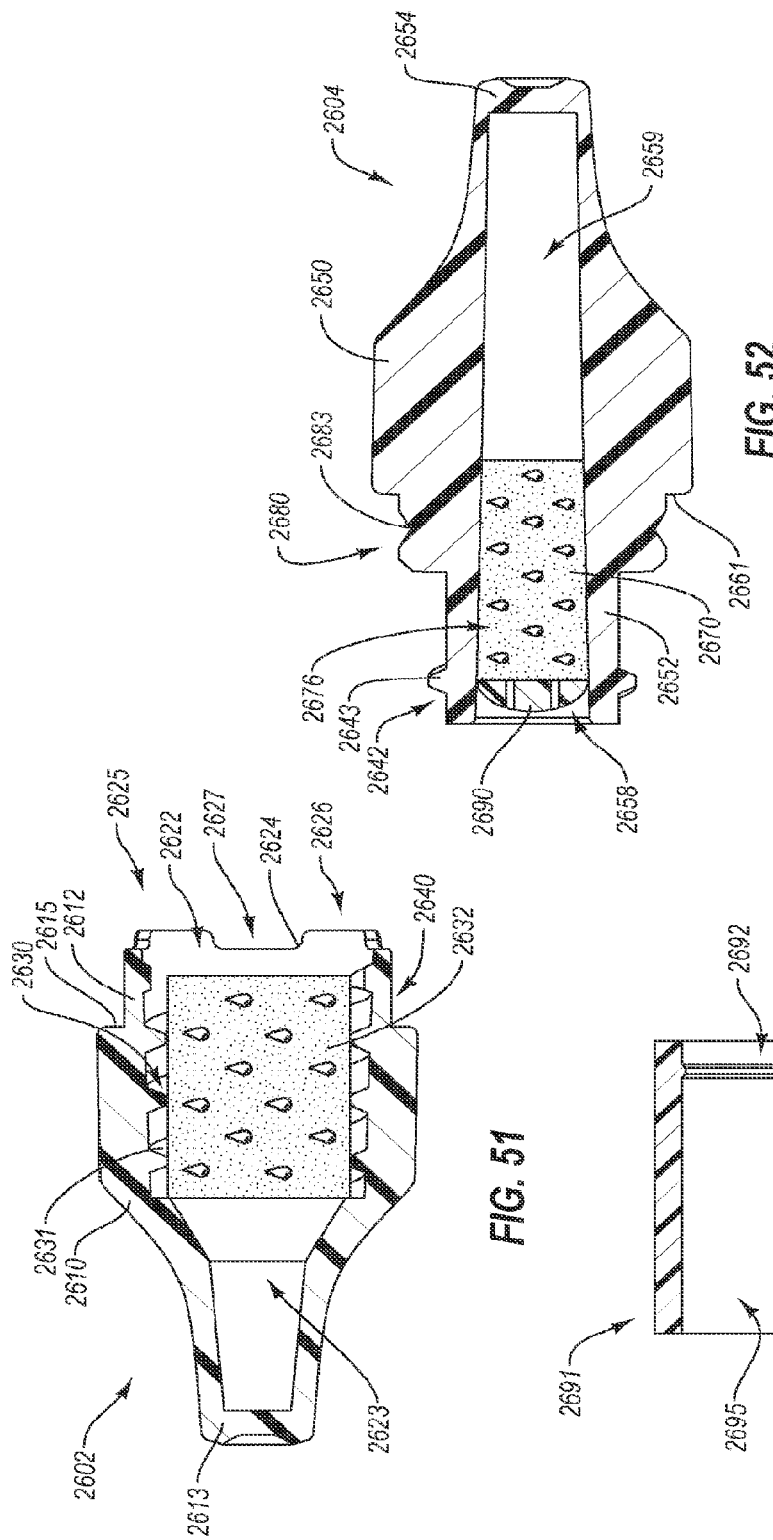
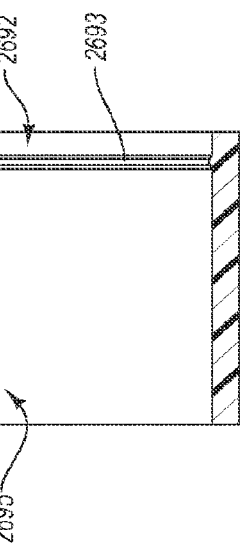
FIG. 51
FIG. 52
FIG. 53

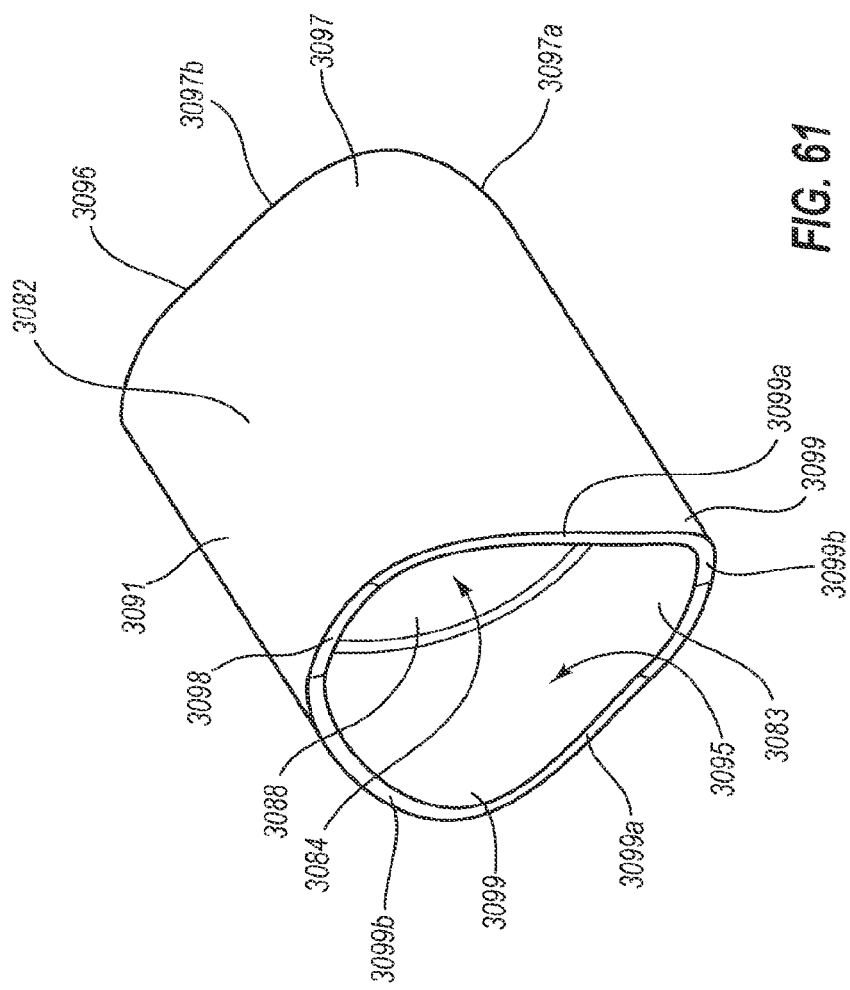

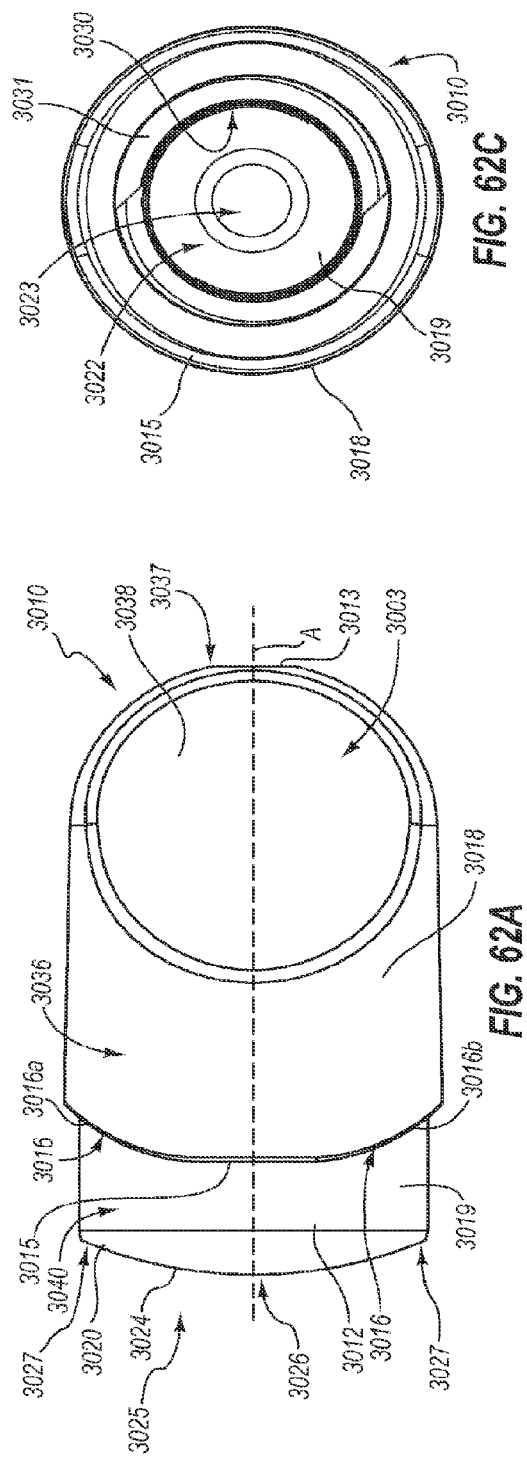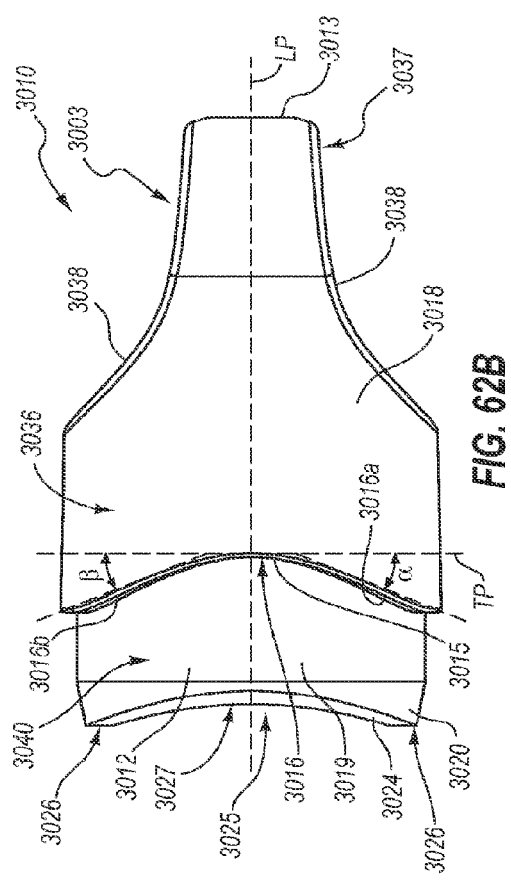

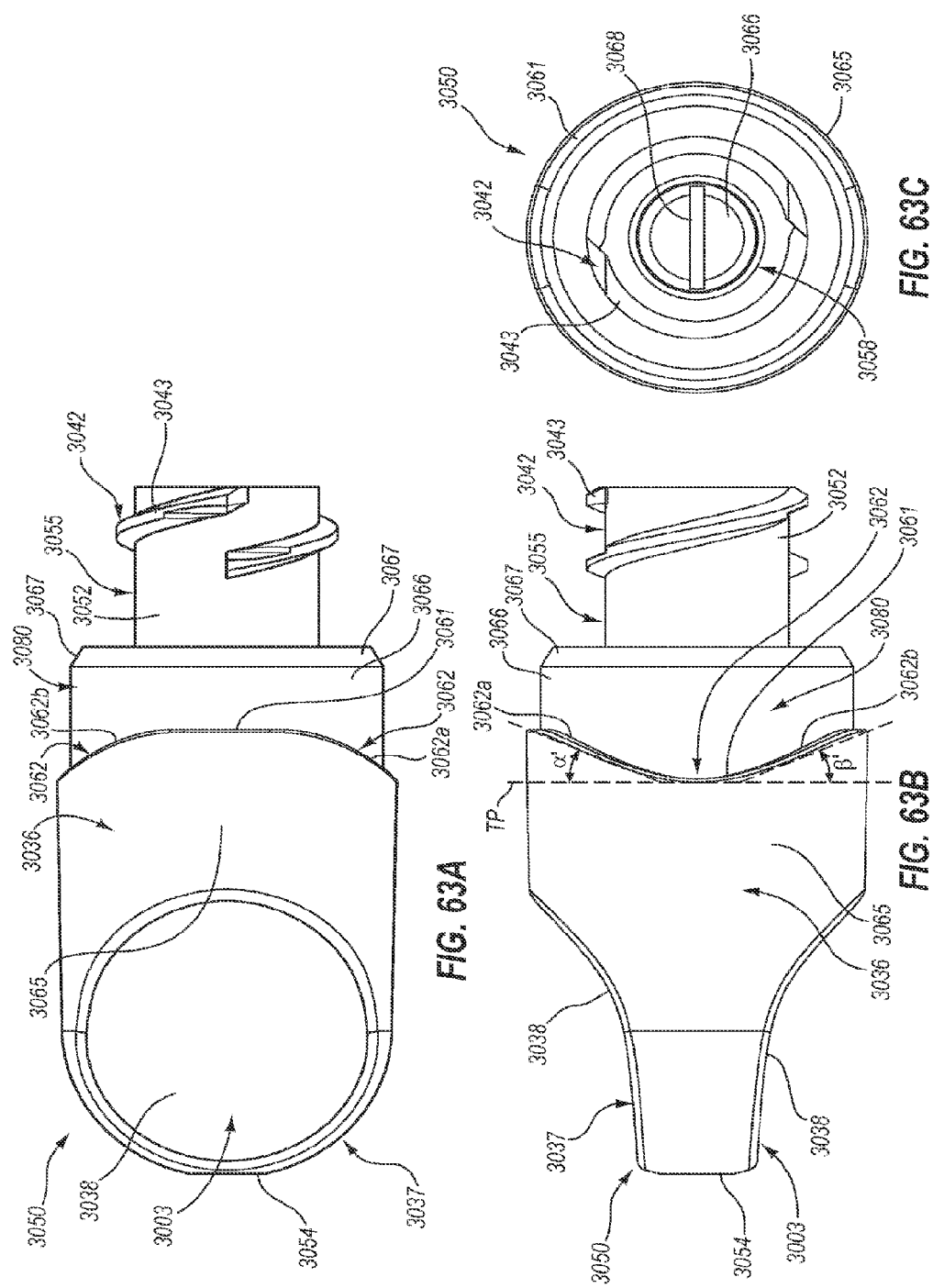

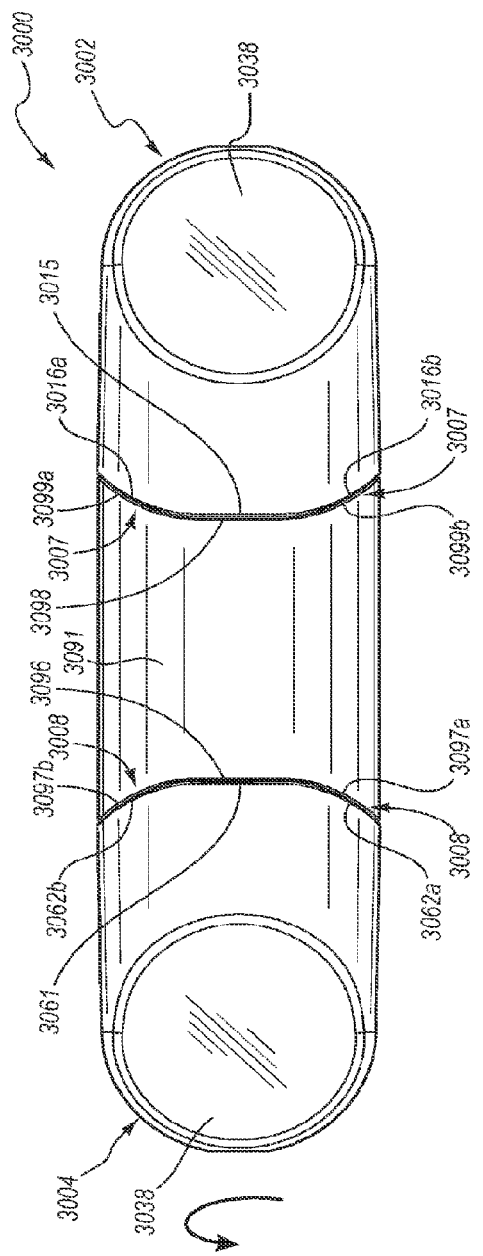
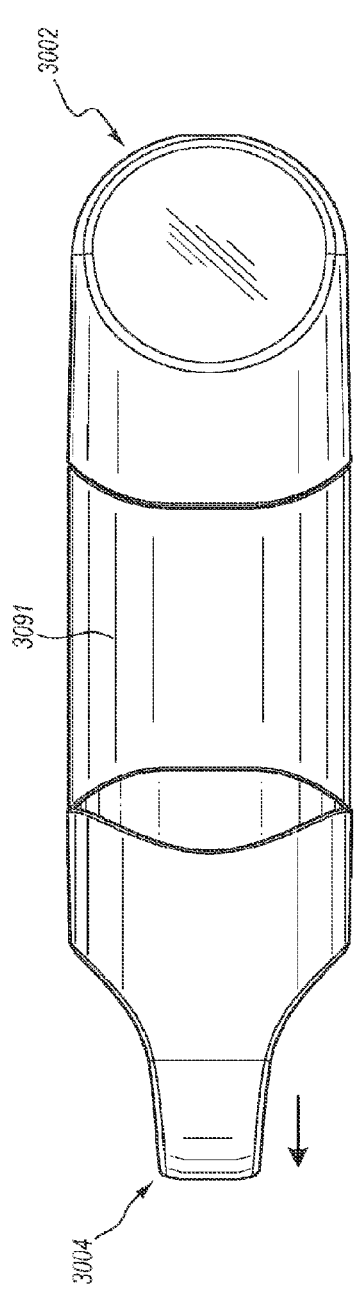
FIG. 65A
FIG. 65B

DISINFECTING CAPS FOR MEDICAL MALE LUER CONNECTORS

CROSS-REFERENCE TO RELATED APPLICATIONS

This application is a continuation of U.S. patent application Ser. No. 14/275,296 filed on May 12, 2014, which is a continuation of U.S. patent application Ser. No. 14/162,207 filed on Jan. 23, 2014, which is a continuation of U.S. patent application Ser. No. 13/736,166 filed on Jan. 8, 2013, which is a continuation of U.S. patent application Ser. No. 13/664,641 filed on Oct. 31, 2012, which is a continuation of U.S. patent application Ser. No. 13/281,404, filed Oct. 25, 2011, which issued as U.S. Pat. No. 8,328,767 on Dec. 11, 2012 and a continuation of U.S. patent application Ser. No. 12/917,336, filed Nov. 1, 2010, which issued as U.S. Pat. No. 8,523,830 on Sep. 3, 2013. Application Ser. No. 13/281,404 is a continuation-in-part of U.S. patent application Ser. No. 12/610,141, filed Oct. 30, 2009, which issued as U.S. Pat. No. 8,172,825 on May 8, 2012, U.S. patent application Ser. No. 12/610,033, filed Oct. 30, 2009, U.S. patent application Ser. No. 12/171,997, filed Jul. 11, 2008, which issued as U.S. Pat. No. 8,197,749 on Jun. 6, 2012, and U.S. patent application Ser. No. 12/164,310, filed Jun. 30, 2008, which issued as U.S. Pat. No. 8,177,761 on May 15, 2012, all of which are continuations-in-part of U.S. patent application Ser. No. 12/014,388, filed Jan. 15, 2008, which claims the benefit of U.S. Provisional Application No. 60/880,541, filed Jan. 16, 2007. This application is also a continuation of U.S. patent application Ser. No. 13/678,057, filed Nov. 15, 2012, which is a continuation of U.S. patent application Ser. No. 12/956,704, filed Nov. 30, 2010, which issued as U.S. Pat. No. 8,343,112 on Jan. 1, 2013, which is a continuation-in-part of U.S. patent application Ser. No. 12/610,141, filed Oct. 30, 2009, which issued as U.S. Pat. No. 8,172,825 on May 8, 2012, and of U.S. patent application Ser. No. 12/917,336, filed Nov. 1, 2010, which issued as U.S. Pat. No. 8,523,830 on Sep. 3, 2013. U.S. patent application Ser. No. 12/956,704, filed Nov. 30, 2010, also claims priority from U.S. Provisional Application No. 61/265,207, filed Nov. 30, 2009. This application is also a continuation of U.S. patent application Ser. No. 13/794,338, filed Mar. 11, 2013, which is a continuation of U.S. patent application Ser. No. 13/564,122, filed Aug. 1, 2012, which issued as U.S. Pat. No. 8,419,713 on Apr. 16, 2013. This application is also a continuation of U.S. patent application Ser. No. 13/972,101, filed Aug. 21, 2013, which is a division of U.S. patent application Ser. No. 12/957,263, filed Nov. 30, 2010, which issued as U.S. Pat. No. 8,523,831 on Sep. 3, 2013, which is a continuation-in-part of U.S. patent application Ser. No. 12/610,141, filed Oct. 30, 2009, which issued as U.S. Pat. No. 8,172,825 on May 8, 2012, and of U.S. patent application Ser. No. 12/917,336, filed Nov. 1, 2010, which issued as U.S. Pat. No. 8,523,830 on Sep. 3, 2013. U.S. patent application Ser. No. 12/957,263, filed Nov. 30, 2010, also claims priority from U.S. Provisional Application No. 61/265,216, filed Nov. 30, 2009. All of these applications are incorporated herein by reference in their entirety.

BACKGROUND

1. Technical Field

The present disclosure generally relates to caps for medical connectors and more specifically relates to caps that can be used to protect the sterility of unconnected medical connectors, such as connectors that may be used for fluid flow or for fluid delivery systems. Some embodiments are directed to caps for medical connectors that include elongated male portions.

2. Related Art

Bloodstream infections, such as may be caused by microorganisms that enter patients via intravascular catheters, are a significant cause of illness and excess medical costs. A substantial number of such infections occur in U.S. intensive care units annually. Additionally, a significant fraction of these infections result in death.

Guidelines from the Centers for Disease Control and Prevention describe various ways to limit bloodstream infections in hospital, outpatient, and home care settings. The guidelines address issues such as hand hygiene, catheter site care, and admixture preparation. However, despite these guidelines, such infections continue to plague healthcare systems at relatively unchanged rates.

Impregnating catheters with various antimicrobial agents is one approach for reducing these infections. Impregnated catheters, however, provide less than satisfactory results. Additionally, some microbes have developed resistance to the various antimicrobial agents used in the catheters. Other systems and approaches have also been developed, but these likewise suffer from a variety of limitations and drawbacks.

SUMMARY

Disclosed herein are disinfecting caps, and related systems and methods, that can reduce the threat of microorganisms entering the bloodstream of a patient via fluid flow or fluid delivery systems, such as, for example, needleless injection sites and/or fluid transfer devices having an elongated male portion or male protrusion, such as, for example, a male luer. In some embodiments, a cap is configured to couple with and disinfect a medical connector having a male protrusion. In further embodiments, the cap can include an antiseptic, and can be configured to create a seal with the male protrusion so as prevent antiseptic from entering a lumen of the male protrusion. In some embodiments, the antiseptic may be contained within a pad prior to the coupling of the cap to the medical connector, and the act of coupling the cap to the medical connector can force at least a portion of the antiseptic from the pad and into contact with the male protrusion. Other or further features of various embodiments are also disclosed below and are set forth in the appended claims, which are hereby incorporated by reference in this summary section.

BRIEF DESCRIPTION OF THE DRAWINGS

FIG. 2 is an exploded side elevation view of the medical caps of FIG. 1;

FIG. 3 is a perspective view of a female medical cap from the assembly of FIG. 1, which shows internal threads;

FIG. 4 is a perspective view of the female cap of FIG. 3 and an associated medical connector about to be connected therewith;

FIG. 5 is a perspective view of male cap from the assembly of FIG. 1 and a luer lock connector to which the male cap may be affixed;

FIG. 10 is a cross-sectional perspective view of another embodiment of an assembly that includes a pair of caps, which are attached to each other via a threaded interface;

FIG. 11 is an exploded perspective view of the assembly of FIG. 10 showing the caps detached from each other;

FIG. 12 is a cross-sectional perspective view of another embodiment of an assembly that includes a pair of caps, which are attached to each other via a snapping interface;

FIG. 13 is a cross-sectional perspective view of another embodiment of an assembly that includes a pair of caps, which are attached to each other via a friction-fit interface;

FIG. 22 is a perspective view of another embodiment of an assembly that includes a pair of caps, which are attached to each other via a snapping interface;

FIG. 23 is a cross-sectional view of another embodiment of an assembly that includes a pair of caps and a sleeve, wherein the caps are shown attached to the sleeve;

FIG. 27 is a perspective view focusing on one cap portion of the assembly of FIG. 25, with covers removed from the assembly;

FIG. 28 is a perspective view focusing on the other cap portion of the assembly of FIG. 25, with covers removed from the assembly;

FIG. 51 is a cross-sectional view of the female cap of FIG. 50 taken along the view line 51-51;

FIG. 52 is a cross-sectional view of the male cap of FIG. 49 taken along the view line 52-52;

FIG. 53 is a cross-sectional view of the sleeve of FIG. 49 taken along the view line 53-53;

FIG. 61 is a perspective view of an embodiment of a sleeve that is compatible with the assembly of FIG. 59;

FIG. 62A is a top plan view of an embodiment of a housing portion of a female cap that is compatible with the assembly of FIG. 59;

FIG. 62B is a side elevation view of the housing portion of the female cap of FIG. 62A;

FIG. 62C is a front elevation view of the housing portion of the female cap of FIG. 62A;

FIG. 63A is a top plan view of an embodiment of a housing portion of a male cap that is compatible with the assembly of FIG. 59;

FIG. 63B is a side elevation view of the housing portion of the male cap of FIG. 63A;

FIG. 63C is a front elevation view of the housing portion of the male cap of FIG. 63A;

FIG. 65A is a top plan view of the assembly of FIG. 59;

FIG. 65B is a top plan view of the assembly of FIG. 59 showing a male cap portion thereof having been rotated so as to assist in the release of the male cap from the assembly;

DETAILED DESCRIPTION

Disclosed herein are caps that can be used to protect and/or disinfect medical connectors. Systems and methods related to such caps are also disclosed. An example of medical connectors for which caps disclosed herein may be used are intravascular connectors associated with a fluid pathway, such as an IV line. Commonly, a fluid pathway is used to intermittently administer medications to a patient. For example, a fluid pathway, which communicates fluids with a patient's blood stream, may have one or more connectors associated therewith. Each of the fluid pathway connectors can be connected to other connectors, such as a connector associated with a central line. In such a situation, the medical connectors, such as luer lock connectors, are connected and disconnected at various times, and may remain disconnected for several minutes or hours. Medical connector caps are used to cover and protect the various medical connectors while the connectors are separated from one another. When the medical connectors are separated from each other, there are two connectors that each can benefit from being covered by a cap. Therefore, in some cases, it can be advantageous to have a single connector set that can be used to provide protection for both ends of a separated connection. In other or further embodiments, a cap can include an antiseptic for disinfecting a medical connector. In some cases, it can be advantageous for the cap to form a seal with the medical connector to thereby prevent the antiseptic from exiting the cap into the fluid pathway.

Figure 1:
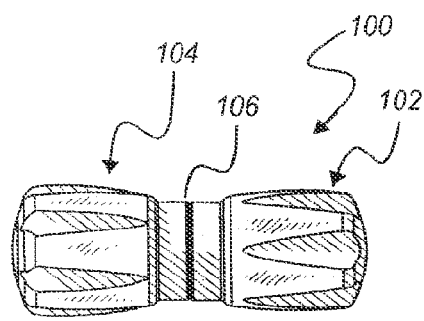
FIG. 1 is a side elevation view of an embodiment of an assembly that includes an attached pair of medical caps.
Figure 1A:
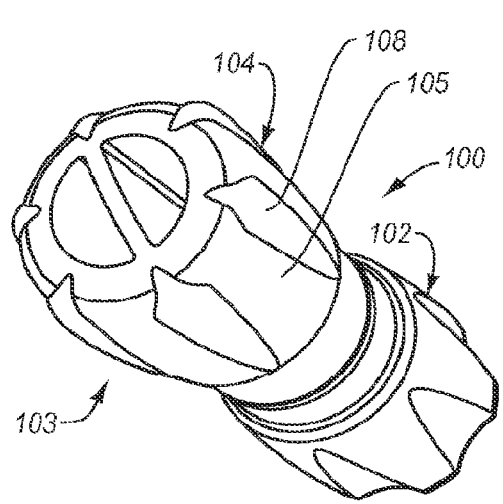
FIG. 1A is an end perspective view of the caps of FIG. 1.
Figure 1B:
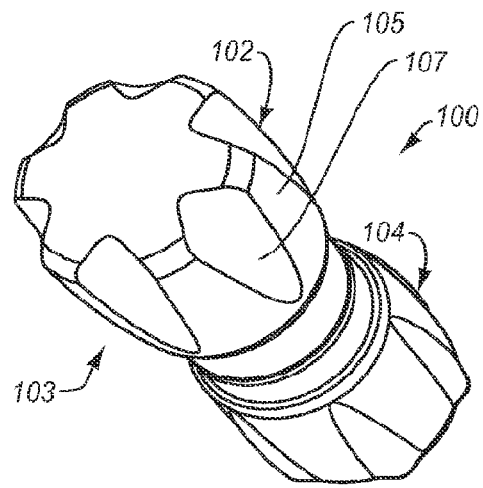
FIG. 1B is an end perspective view of the caps of FIG. 1 shown from a vantage point opposite of that shown in FIG. 1A.

Shown in FIGS. 1-1B, is a system, unit, or assembly 100 of a pair of separable caps 102 and 104, which are securely, but releasably, affixed one to the other across a common interface 106. When assembly 100 is in a pre-use or initially packaged state, the internal parts and surfaces thereof can be sterile, and these are able to reduce, prevent, or eliminate contamination of connectors with which caps 102, 104 can be coupled.

As further discussed below, in various embodiments, caps 102 and 104 can be distributed in a coupled state, such as that shown in FIGS. 1-1B, and may be decoupled by a user (e.g., a medical professional) and subsequently coupled with separate medical connectors. Caps 102 and 104 can include features to aid in such a decoupling action and/or in the coupling of caps 102, 104 with the respective connectors. For example, in the illustrated embodiment, each cap 102, 104 includes gripping features 103.

The gripping features 103 can comprise longitudinally extending lands or ridges 105 that taper from a relatively wide width near the interface 106 of the caps 102, 104 to a narrower width at or near an outer end of the cap 102, 104. The gripping features 103 can further include longitudinally extending depressions or grooves 107 between adjacent ridges 105. For example, as can be seen in FIGS. 1-8B, the grooves 107 can extend radially inwardly from an outer surface of the cap 102 that comprises the ridges 105, and the grooves 107 can also commence at a position near the interface 106 and can grow wider and deeper toward an outer end of the cap 102. The gripping features 103 can further include longitudinally extending bumps or protrusions 108 between adjacent ridges 105. As can be seen in FIGS. 1-8B, the protrusions 108 can extend radially outwardly from an outer surface of the cap 104 that comprises the ridges 105, and the protrusions 108 can also commence at a position near the interface 106 and can grow wider and taller toward an outer end of the cap 104. The uneven surfaces provided by the ridges 105 and the grooves 107 or protrusions 108 can facilitate rotational movement of the caps 102, 104 (e.g., rotational movement relative to each other), which can aid in decoupling the caps 102, 104 from each other and/or securing the caps 102, 104 to separated connectors. For example, the uneven surfaces may be easily gripped by the fingertips of a medical practitioner.

As can be seen, for example, in FIGS. 1A and 1B, the patterns of the ridges 105, grooves 107, and/or protrusions 108 can be different for the caps 102, 104. In the illustrated embodiment, cap 102 includes only ridges 105 and grooves 107, whereas cap 104 includes only ridges 105 and protrusions 108. Such differences can aid in distinguishing the caps 102, 104 from each other. Other features and methods for distinguishing the caps 102, 104 from each other are discussed further below.

Caps 102 and 104 are shown as separated from each other, or in a decoupled state, in FIG. 2, wherein cap 104 is shown as having an insertable or male section 109. Section 109 has an elongated portion 110 that ends at an exteriorly disposed threaded segment 112. Threaded segment 112 comprises threads 114 that are sized and shaped to be inserted and joined by threading into cap 102.

Cap 102, as shown in FIG. 3, has a closed, hollow interior 116, which may also be referred to as a disinfection cavity or chamber, which opens outwardly at a proximal end 118 to expose an interiorly disposed threaded segment 120 that includes threads 122. Threads 122 are of a size and pitch to complementarily engage threads 114 of cap 104 for a screw or push-on tight fit with cap 104.

As illustrated in FIG. 4, cap 102 has an interior surface 124, an opening edge 126 and an exterior surface 128, opening edge 126 being a common link between interior surface 124 and exterior surface 128. Further, threads 122 also have a size and pitch to engage a threadable segment 130 of a female connector, such as for example, female luer connector 132. Such connectors are generally and commonly used as catheter and other fluid-tight protective connectors in medical applications. As seen in FIG. 4, cap 102 provides a protective cover for connector 132 when encased about connector 132 (displaced in direction of arrow 134) whereupon threadable segment 130 engages and is drawn into a secure, but releasable connection with threads 122 of cap 102.

In some embodiments, the connector 132 comprises a needleless injection site, which may sometimes referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). Stated otherwise, in some embodiments, cap 102 can be suitably connected with any of a variety of different needleless injection sites, such as those previously listed. In certain embodiments, once cap 102 has been applied to or coupled with connector 132, it is unnecessary to disinfect (e.g. treat with an alcohol swab) the connector 132 prior to each reconnection of the connector 132 with another connector, as the connector 132 will be kept in an uncontaminated state while coupled with the cap 102. Use of the cap 102 thus can replace the standard swabbing protocol.

As seen in FIG. 5, threads 114 of cap 104 are of a size and pitch to engage threads 138 of a male luer-lock connector 136. For example, connector 136 can comprise the end of an IV tubing set that is disconnected from an IV catheter needleless injection site. Note that cap 104 has a medially disposed, elongated hole 140, which may also be referred to as a disinfection chamber, into which a male protrusion 141 of connector 136 may be facilely and securely inserted when cap 104 is displaced in the direction of arrow 144 to engage connector 136. The male protrusion 141 may be of any suitable variety. The term "male protrusion" is used broadly herein, and includes any elongated structure. In the illustrated embodiment, the male protrusion 141 comprises a frustoconical luer 142.

Cap 104 also has a surface 146 which continues through to a circular edge 148. Further, distally displaced from circular edge 148, surface 146 abruptly ends at a circular ring shaped edge 150, which is therefrom joined to an outside surface 152. It may be noted that opening edge 126 (see FIG. 4) and ring shaped edge 150 combine to form common interface 106 (see FIG. 1) when cap 102 is affixed to cap 104 to construct assembly 100. It should also be noted that, in certain embodiments, surfaces of assembly 100, which contact internal surfaces of a connector, such as connector 132 or connector 136, are sufficiently sterile or aseptic to not contaminate the inner surfaces thereof.

Internal portions and associated edges of caps 102 and 104 can be pre-sterilized and so maintained until use. Caps 102 and 104 may be injection molded using polypropylene or other material that can be sterilized and which is impervious to contaminating agents while cap 102 is nested with cap 104, before being opened for use. Caps 102 and 104 can be impregnated or coated with an antimicrobial substance. As an example, each cap 102 and cap 104 may be individually sterilized by ethylene oxide (ETO) before final assembly and aseptically paired, or assembly 100 may be finally consolidated as a single unit and then sterilized, such as by radiation (e.g. gamma). Assembly 100 can be kept intact until the time of use, with internal surfaces of nested parts 102 and 104 remaining clean and sterile until assembly 100 is opened for use.

Figure 7:
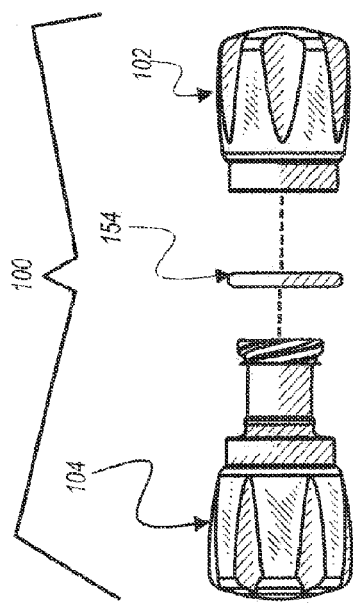
FIG. 7 is an exploded side elevation view of the cap assembly of FIG. 6.
Figure 7B:
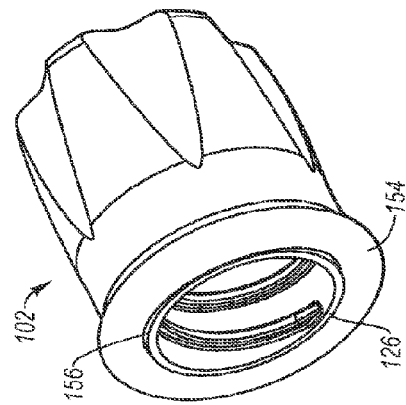
FIG. 7B is a perspective view of the other cap of FIG. 7 with a sealing mechanism disposed thereon.
Figure 6:
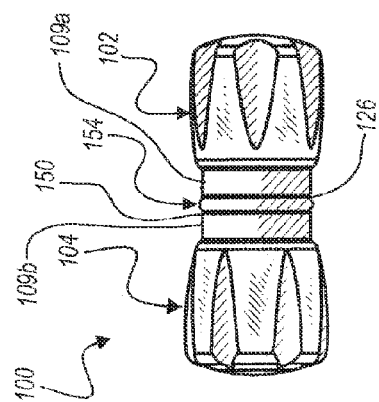
FIG. 6 is a side elevation view of an attached pair of medical caps, similar to the caps of FIG. 1, but having an embodiment of a sealing mechanism at connecting edges of the caps.
Figure 7A:
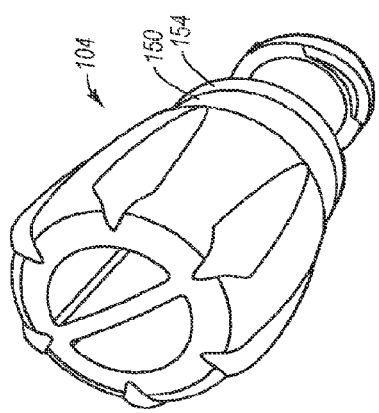
FIG. 7A is a perspective view of one of the caps of FIG. 7 with a sealing mechanism disposed thereon.

Reference is now made to FIGS. 6 through 7B, wherein a seal, such as an O-ring, is disposed between surfaces 126 and 150 to provide yet another barrier against internal surface contamination of caps 102 and 104. As seen in FIG. 6, an O-ring 154 is disposed between surfaces 126 and 150 to provide a seal thereby. While O-ring 154 can be displaced from caps 102 and 104 as illustrated in FIG. 7, it is anticipated that O-ring 154 can be adapted to remain affixed to one of caps 102 and 104. For example, as illustrated in FIG. 7A, O-ring 154 can remain positioned adjacent surface 150 on cap 104 when caps 102 and 104 are disconnected from one another, rather than being separated when cap 104 is displaced from cap 102, as seen in FIG. 7.

Alternatively, O-ring 154 can be associated with cap 102, as seen in FIG. 7B. In particular, opening edge 126 of cap 102 can have an annular groove 156 for receiving O-ring 154 therein Annular groove 156 can be sized and shaped such that O-ring 154 sealingly engages cap 104 or a medical connector when cap 102 is coupled thereto. It will be appreciated that annular groove 156 can be disposed in opening edge 126 toward the exterior of cap 102 as illustrated in FIG. 7B, or annular groove 126 can be disposed in opening edge 126 towards the interior of cap 102. In some exemplary embodiments, opening edge 126 of cap 102 does not have annular groove 126 therein. In such embodiments, O-ring 154 can be mounted directly to opening edge 126. O-ring 154 can be mounted on or to caps 102 or 104 in any suitable manner, including with the use of an adhesive, such as glue, a mechanical fastener, or a friction fitting.

While the seal between caps 102 and 104 has been described as being an O-ring mounted on one of caps 102 or 104, it will be appreciated that other seals are contemplated. For example, each of caps 102 and 104 can have an O-ring mounted thereon. In such a configuration, the two O-rings abut each other when caps 102 and 104 are coupled together, thereby forming a seal to antiseptically partition the internal and external surfaces of caps 102 and 104. In an alternate embodiment, an O-ring or other sealing mechanism can be mounted on surfaces 109*a* and 109*b*. Alternatively, one or both of caps 102 and 104 can be formed with a lip, bump, or groove that provides a sealing function when caps 102 and 104 are coupled to each other or to separated medical connectors. In one exemplary embodiment, one of caps 102 and 104 has a ridge extending around its interfacing surface, and the other cap has a corresponding groove in its interfacing surface into which the ridge is received to create the seal. In yet another exemplary embodiment, one or both of caps 102 and 104 can be overmolded or comolded using any known and suitable overmolding or comolding process. For example, one or both of caps 102 and 104, and associated surfaces 126 and 150, can be overmolded or comolded. Thus, caps 102 and 104 can be formed of a polymer, and surfaces 126 and 150 can be formed of a softer polymer that is comolded or overmolded to the rest of caps 102 or 104. Surfaces 126 and 150, formed of the softer polymer, are thus able to be compressed or deformed sufficiently to create an impermeable seal when caps 102 and 104 are coupled together or coupled to separated medical connectors. Other suitable seals or sealing mechanisms are also possible, such as those described below with respect to further embodiments.

As noted elsewhere herein, a sealing mechanism can be used to limit or prevent evaporation or loss of an antiseptic agent disposed within caps 102 and 104 when caps 102 and 104 are coupled together. Additionally, a sealing mechanism, as described herein, can also limit or prevent evaporation or loss of an antiseptic agent disposed within caps 102 and 104 when caps 102 and 104 are coupled to separated medical connectors. Further, a sealing mechanism can limit or prevent microbial ingress within caps 102 and 104 when they are coupled to each other, or within caps 102 and 104 when caps 102 and 104 are individually coupled to separated medical connectors. Moreover, a sealing mechanism can be configured to maintain an antiseptic agent within caps 102 and 104 when caps 102 and 104 are either coupled to one another or to separated medical connectors for a predetermined amount of time. Thus, the seal may be adapted to limit or prevent microbial ingress, while also partially or completely preventing evaporation of an antiseptic agent disposed within caps 102 and 104 when caps 102 and 104 are coupled together or when caps 102 and 104 are coupled to separated medical connectors. Similarly, the seal may be configured to limit or prevent microbial ingress while not preventing evaporation of an antiseptic agent disposed within caps 102 and 104. In yet other embodiments, no seal is provided between caps 102 and 104 when coupled together or between caps 102 and 104 when coupled to separated medical connectors.

Figure 8B:
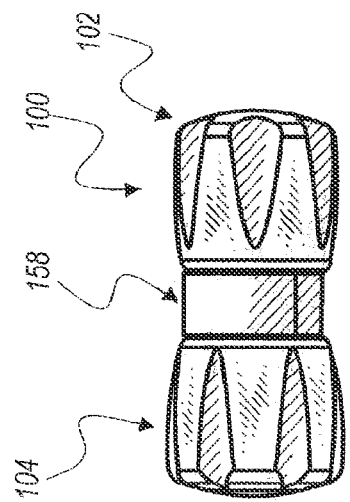
FIG. 8B is a side elevation view of the interconnected cap assembly of FIG. 8A with the seal fully in place.
Figure 8A:
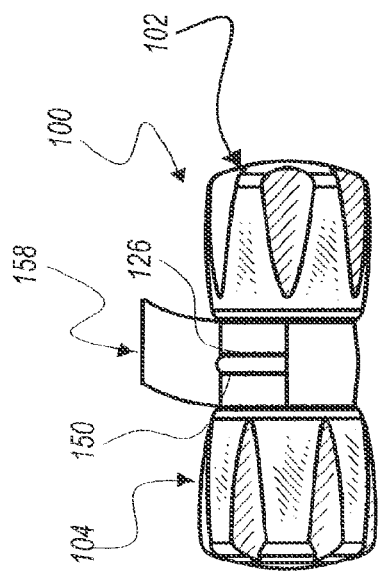
FIG. 8A is a side elevation view of the interconnected cap assembly of FIG. 6 with an embodiment of a seal partially displaced about connecting edges of the cap assembly.

Further safety in sealing against internal surface contamination may be provided by a sealing tape, or a planar or foil seal, such as tape 158 seen in FIG. 8A. Tape 158 is disposed to fully cover exposed edges of surfaces 126 and 150. Tape 158 may, for example, be of an impervious pliable material, such as a metallized-surface mylar. As seen in FIG. 8B, tape 158 is wrapped about surfaces 126 and 150 to provide a secure seal. It is preferred that tape 158 frangibly divides when cap 102 is separated from cap 104 to facilitate separation of caps 102 and 104 and provide a visible indication that the seal is broken. Thus tape 158 provides both a seal to prevent microbial ingress and a mechanism for maintaining the secure connection between caps 102 and 104 prior to use. It will be appreciated, however, that any suitable sealing mechanism can be used to maintain the secure connection between caps 102 and 104 prior to use. For example, any sealing mechanism can be used that securely and selectively couples caps 102 and 104 together, requires deliberate action to break the seal, and provides a visual indication of whether the seal has been broken. By way of example and not limitation, a suitable sealing mechanism may include a heat stake, a frictional seal, a barbed seal, a ratchet seal, and the like.

Figure 9A:
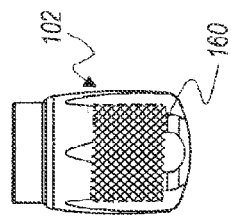
FIG. 9A is a side elevation view of the cap portion of FIG. 3 and an absorbent pad positioned above the cap portion.
Figure 9B:
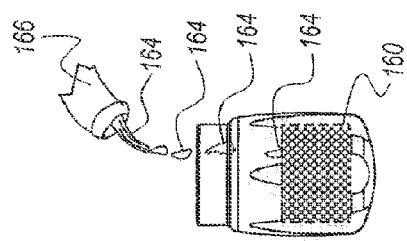
FIG. 9B is a side elevation view of the cap portion and pad of FIG. 9A schematically showing the absorbent pad disposed within the cap portion.
Figure 9C:
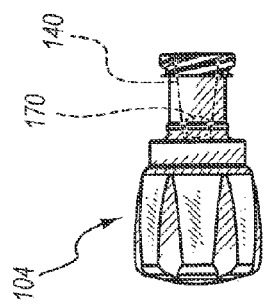
FIG. 9C is a side elevation view of the cap portion and pad of FIG. 9B with a quantity of antiseptic material being dispensed into the cap and pad.

When capping disconnected medical connectors, it can be desirable to do more than merely cover the connectors. For example, an absorbent pad, such as pad 160, seen in FIG. 9A, may be included within cap 102 (e.g., within the disinfection chamber 116), such as by displacing pad 160 into cap 102 as indicated by arrow 162. Pad 160 is seen disposed in cap 102 in FIG. 9B. An antiseptic 164 can also be disposed within cap 102 as illustrated in FIG. 9C. Antiseptic 164 can be in liquid or solid form. For example, alcohol or another stable liquid antiseptic may be added from a container 166 to be received within, wet, soak, or saturate pad 160 to a predetermined concentration level. Note that once assembly 100 is fully assembled, pad 160 will substantially remain at the predetermined concentration level due to the exterior seals provided for assembly 100 as described herein. Alternatively, or additionally, pad 160 may receive or be impregnated with a dry antiseptic, such as, for example, chlorhexidine gluconate.

Figure 9D:
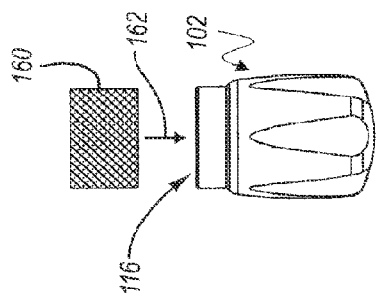
FIG. 9D is a perspective view of the cap portion containing the pad of FIGS. 9B and 9C affixed to an associated complementary cap.

Further note that once cap 104 is securely affixed to cap 102, as seen in FIG. 9D, pad 160 is disposed to contact at least circular edge 148 (see also FIG. 5). (In FIG. 9D, parts of cap 104 which are internal to assembly 100 are seen with hidden or dashed lines.) Such contact provides a wiping action preferred to make contact with a surface before contact is made with an associated connector. Note also that residual antiseptic on associated internal surfaces of cap 104 may be transferred to related parts of the associated connector for cleaning and/or disinfecting purposes.

Pad 160 can be formed of a deformable, resilient material such that when cap 104 is coupled to cap 102, elongated portion 110 can compress pad 160 within cap 102, as illustrated in FIG. 9D. Further, pad 160 can expand to its original shape when cap 104 is removed from cap 102. Similarly, pad 160 can be compressed within cap 102 when cap 102 is coupled to a medical connector, such as medical connector 132. More specifically, during the connection of cap 102 to a medical connector, cap 102 and pad 160 rotate relative to an opening edge of the medical connector, thereby drawing the medical connector into cap 102. The rotation of cap 102 causes pad 160 to wipe or scrub the opening edge of the medical connector. Pad 160 and any antiseptic disposed within cap 102 can thus cleanse and disinfect the opening edges of the medical connector. Pad 160 can also be formed such that when a medical connector is coupled to cap 102, pad 160 is deformed such that pad 160 extends around the opening edges and/or threads of the medical connector. For example, pad 160 can be formed such that as cap 102 is twisted onto medical connector 132, pad 160 deforms around threads 130 and/or the opening edges of medical connector 132, thereby scrubbing threads 130 and/or the opening edge of medical connector 132.

Pad 160 can also provide additional functionality when a liquid antiseptic is disposed within cap 102. In particular, pad 160 acts as a sponge to absorb or release the liquid antiseptic within cap 104. More specifically, when pad 160 is compressed by elongate portion 110 of cap 104 (FIG. 9D; see also elongate portion 268 compressing pad 160 in FIG. 14) or the opening edges of a medical connector coupled to cap 102, pad 160 releases at least a portion of the antiseptic so that the antiseptic can be transferred to elongate portion 110 or the opening edges of the medical connector. Conversely, when cap 102 or a medical connector is disconnected from cap 102, pad 160 expands and absorbs excess antiseptic so that the antiseptic does not drip or spill out of cap 102.

Figure 9E:
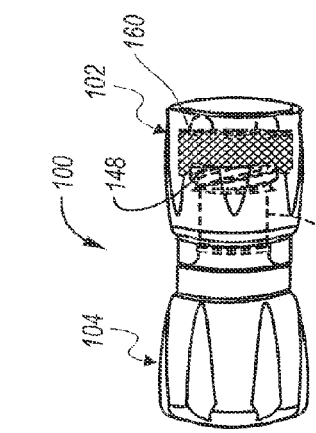
FIG. 9E is a side elevation view of the cap portion of FIG. 5 and an absorbent pad disposed therein.

Similar to pad 160 and antiseptic 164 disposed within cap 102, cap 104 may also have a pad and/or an antiseptic disposed therein. For example, as illustrated in FIG. 9E, a pad 170 may be disposed within elongate hole 140 of cap 104. An antiseptic can also be disposed within cap 104 in a manner similar to antiseptic 164 in cap 102. Antiseptic can be in liquid or solid form. For example, alcohol or another stable liquid antiseptic may be added from a container to saturate pad 170 to a predetermined level. Alternatively, or additionally, pad 170 may be impregnated with a dry antiseptic, such as chlorhexidine gluconate. Once assembly 100 is fully assembled, an antiseptically saturated pad 170 disposed within cap 104 will substantially remain at the predetermined saturation level due to the exterior seals for assembly 100 as described above. Once caps 102 and 104 are disconnected from each other and connected to individual medical connectors, pad 170 disposed within cap 104 may scrub related parts of the associated connector for cleaning and/or disinfecting purposes. It will be appreciated, however, that in some embodiments, pad 170 may not contact a medical connector coupled to cap 104. Additionally, the antiseptic disposed within cap 104 may be transferred to the related parts of the associated medical connector for cleaning and/or disinfecting purposes.

Additional embodiments of caps such as the caps 102, 104 are provided in FIGS. 10-29 and the associated written description of U.S. patent application Ser. No. 12/171,997, titled STERILITY-PROTECTING CAPS WITH FLUID RESERVOIR FOR SEPARATED CONNECTORS, which was filed on Jul. 11, 2008 and was published as U.S. Patent Application Publication No. 2009/0062766 on Mar. 5, 2009 ("the Publication"), which is hereby incorporated by reference herein. As indicated in the Publication, any suitable feature of the illustrative embodiments of FIGS. 16-29 of the Publication, which are described with respect to a female-type cap similar to the cap 102, may be applied to or incorporated within a male-type cap, similar to the cap 104. Likewise, the female-type caps described with reference to FIGS. 16-29 of the Publication can be coupled to a male-type cap in a manner similar to that described with reference to caps 102 and 104, in which the caps 102, 104 are nested with each other. In other embodiments, any suitable feature of the caps described with respect to FIGS. 1-29 of the Publication, whether of a male or female variety, can be formed and/or employed without being nested or otherwise associated with a complementary cap.

Discussed hereafter are additional embodiments of caps, which can have coupling arrangements and/or other features that differ in certain respects from those of the caps 102, 104 described above and other caps described in the Publication. Any suitable feature of such caps can be incorporated into the caps described hereafter, and vice versa.

FIGS. 10 and 11 depict a system or assembly 1000 that includes a first protective medical connector, shield, or cap 1002 and a second protective medical connector, shield, or cap 1004. As shown in FIG. 10, the caps 1002, 1004 are connected to each other when the assembly 1000 is in a shipping or pre-use state. As shown in FIG. 11, the caps 1002, 1004 can be separated from each other such that each may be coupled with a corresponding or complementary medical connector. For example, as with the cap 102, the cap 1002 can be configured to be coupled with a female connector, such as a female luer lock or a needleless injection site (see, e.g., FIG. 4). Accordingly, the cap 1002 may be referred to as a female cap. As with the cap 104, the cap 1004 can be configured to couple with a male connector, such as a male luer lock (see, e.g., FIG. 5). Accordingly, the cap 1004 and may be referred to as a male cap.

With continued reference to FIGS. 10 and 11, the cap 1002 can comprise a housing 1010. The housing 1010 can be elongated, and may define a cylinder or any other suitable shape. For example, in the illustrated embodiment, the housing 1010 includes a sidewall 1012 that defines a substantially cylindrical outer surface 1014. The outer surface can be smooth, as shown, which can enhance comfort to a patient if the cap 1002 contacts the patient when coupled with a medical connector. In other embodiments, the outer surface can include gripping features, which can aid in rotating the cap 1002 relative to the cap 1004 to permit separation of the caps 1002, 1004 and/or aid in rotating the cap 1002 relative to a medical connector. Such gripping features can include, for example, ridges, grooves, an/or protrusions similar to the ridges 105, grooves 107, and protrusions 108 described above and/or an elastomeric or other coating or layer having a relatively high coefficient of friction. The sidewall 1012 can define a sealing surface 1016 at one end thereof and can define a terminal edge 1018 at an opposite end thereof.

The housing 1010 can further include a transverse wall or partition 1020. In the illustrated embodiment, the partition 1020 defines a plane that is substantially perpendicular to a longitudinal axis of the sidewall 1012. A first portion of the sidewall 1012 can cooperate with one side of the partition 1020 to define a disinfection chamber 1022, which is closed at one end by the partition 1020 and open at an opposite end thereof (e.g., the sealing surface 1016 can define an open end of the disinfection chamber 1022). Similarly, a second portion of the sidewall 1012 can cooperate with an opposite side of the partition 1020 to define a coupling chamber 1024, which likewise is closed at one end by the partition 1020 and open at an opposite end thereof (e.g., the terminal edge 1018 can define an open end of the coupling chamber 1024).

An interior surface of the sidewall 1012 can include a connecting geometry or connection interface 1030 in the region of the disinfection chamber 1022. The connection interface 1030 can comprise inwardly projecting threads 1031 similar to the threads 122 described above, and can be configured to complementarily engage a connection interface of a medical connector, such as, for example, outwardly projecting threads of a needleless injection site. The threaded connection interface 1030 thus can allow for selective coupling of the cap 1002 to a medical connector in a secure, yet selectively removable fashion. Other configurations of the connection interface 1030 may permit the cap 1002 to be coupled with a medical connector in a secure, yet selectively removable fashion, such as friction-fit, snap-fit, or other suitable interfacing arrangements.

The disinfection chamber 1022 can include a pad 1032 therein. The pad 1032 can resemble the pads 160, 170 described above. In various embodiments, the pad 1032 can be deformable, and can also be configured to retain an antiseptic 1033, such as, for example, the antiseptic 164 described above. In further embodiments, the pad 1032 can be resiliently deformable. For example, the pad 1032 can comprise any suitable sponge-like material, such as an elastomeric foam, any open-cell foam, felt, or non-woven fiber matrix, and can be configured to conform to the contours of a portion of a medical connector that is introduced into the disinfection chamber 1022 (e.g., uneven surfaces of an end of a needleless injection site; see also FIGS. 32-34 and the associated written description herein). The pad 1032 can also comprise any closed-cell foam, as well as a solid elastomeric foam such as silicone or the like.

The pad 1032 can have a series or network of openings or spaces therein that can retain the antiseptic 1033 when the pad 1032 is in an expanded state. For example, the antiseptic 1033 can be received within, occupy, fill (or partially fill), wet, soak, or saturate at least a fraction of the pad 1032, or stated otherwise, can fill the pad 1032 to a given concentration level. Compression of the pad 1032 can cause antiseptic 1033 to egress from the pad 1032 so as to contact the medical connector. Resilient expansion of the foam upon removal of a compressive force can allow the pad 1032 to soak up or absorb at least some of the antiseptic 1033 that had previously been forced from the pad 1032. In some embodiments, the antiseptic 1033 can comprise any liquid antiseptic, such as alcohol (e.g., isopropyl alcohol) at various concentrations ranging from 50-90%, ethanol at various concentrations ranging from 50-95%, and combinations of any alcohols with any antiseptics, or a dry material, such as chlorhexidine, ethylenediaminetetraacetic acid (EDTA), lodaphors, or any suitable combination thereof. Accordingly, although the antiseptic 1033 is schematically depicted in FIG. 10 as a series of droplets, the antiseptic 1033 is not necessarily liquid and may fill the pad 1032 to a greater or lesser extent than what is shown. In the illustrated embodiment, when the disinfection chamber 1022 is in a sealed state (e.g., in its pre-use condition), the pad 1032 is in a relaxed, expanded, or uncompressed state in a longitudinal direction. It is noted that the pad 1032 may be uncompressed in one or more dimensions, yet compressed in one or more other dimensions, when the assembly 1000 is in the pre-use state. For example, the pad 1032 can be expanded or in a relaxed state in a longitudinal direction, yet compressed radially inwardly via the sidewall 1012, when the assembly 1000 is in the pre-use state. Such a lack of compression of the pad 1032 in the longitudinal direction can result from the fact that the cap 1004 does not interact with the connection interface 1030 of the cap 1002 to seal the cap 1002, and thus no portion of the cap 1004 contacts the pad 1032 when the caps 1002, 1004 are in the pre-use configuration.

In the illustrated embodiment, the pad 1032 is substantially cylindrical and defines an outer diameter that is approximately the same size as an inner diameter of the threads 1031. In other embodiments, the outer diameter of the pad 1032 can be larger than the inner diameter of the threads 1031 so as to be radially compressed and held tighter within the disinfection chamber 1022. In further embodiments, the pad 1032 can include threading that projects radially inwardly and that is complementary to the threads 1031 to thereby secure the pad 1032 within the chamber 1022.

The disinfection chamber 1022 can be sealed at the sealing surface 1016 via a cover 1034 that can span an open end of the disinfection chamber 1022. The cover 1034 can be secured to the housing 1010 in any suitable manner, such as, for example, via an adhesive. Preferably, the cover 1034 can be readily removed by a practitioner. For example, in some embodiments, the cover 1034 can include a tab 1035 and a practitioner can readily remove the cover 1034 by holding the housing 1010 in one hand and pulling the tab 1035 away from the housing 1010 with the other hand. The removable cover 1034 can be formed of any suitable material, such as, for example, an impervious pliable material (e.g., foil, plastic, metallized-surface mylar, and the like). The cover 1034 can provide a hermetic seal that can assist in maintaining the sterility of the disinfection chamber 1022 prior to use of the cap 1002 and/or can prevent evaporative loss of antiseptic 1033 from the disinfection chamber 1022.

When the cap 1002 is coupled with a medical connector, the coupling action can bring a portion of the medical connector into contact with the pad 1032 and can allow the pad 1032 to wipe or scrub the medical connector, as described above. Likewise, the antiseptic 1033 can be forced into contact with the medical connector during the coupling phase and can remain in contact with the medical connector, while the cap 1002 is coupled with the medical connector. The connection interface 1030 can cooperate with a connection interface of the medical connector to maintain the cap 1002 in an attached configuration relative to the connector. Moreover, the connection interface 1030 can couple with the medical connector, such as via complementary threading, so as to prevent antiseptic from leaking from the disinfection chamber 1022.

In some embodiments, such as where the pad 1032 is formed of a material that is not fully elastically resilient or that requires a relatively long relaxation time in which to transition from a compressed state to a relaxed or uncompressed state (e.g., in a longitudinal direction), pre-use storage in the relaxed or uncompressed state in at least one dimension can preserve or enhance the cleaning, scrubbing, or disinfection properties of the pad 1032. For example, as the cap 1002 is coupled with the medical connector (e.g., the medical connector 132 of FIG. 4), an end of the medical connector can come into contact with a proximal surface (e.g., the surface furthest from the partition 1020) of the pad 1032. Further advancement of the cap 1002 onto the medical connector can cause the pad 1032 to deform to complement a contour of the end of the medical connector as the pad 1032 is compressed, which can permit a relatively tight or continuous contact between the pad 1032 and the medical connector. In the illustrated embodiment, the cap 1002 is rotated relative to the medical connector, as it is advanced onto the medical connector. This rotational motion causes the contoured surface of the pad 1032 to rub the medical connector. In certain embodiments, increasingly greater compression of the pad 1032 yields increasingly stronger rubbing of the medical connector, coupled with greater amounts of the antiseptic 1033 being expelled from the pad 1032. Accordingly, when the pad 1032 is uncompressed in at least one dimension (e.g., in a longitudinal direction) in a pre-use state, and thus is not plastically deformed or is not subject to time-consuming elastic recovery from pre-compression, the pad 1032 can be in disinfecting contact with the medical connector for a relatively greater portion of the coupling procedure. In some embodiments, a practitioner can more quickly couple the cap 1002 to the medical connector, as there is no need to first wait for the pad 1032 to relax to an uncompressed or expanded state to achieve better disinfection of the medical connector.

Various parameters can be adjusted to determine the amount of antiseptic 1033 that is expelled from the pad 1032 when the cap 1002 is coupled with a medical connector. For example, the depth to which the medical connector is received within the disinfection chamber 1022, the concentration of antiseptic 1033 within the pad 1032, and/or other parameters can be altered. In various embodiments, no less than about ¼, no less than about ⅓, no less than about ½, no less than about ⅔, or no less than about ¾ of the antiseptic 1033 is expelled from the pad 1032 when the cap 1002 is coupled with a medical connector. In some embodiments, all, or substantially all, of the antiseptic 1033 is expelled from the pad 1032.

With reference to FIG. 10, an interior surface the sidewall 1012 can include another connecting geometry or connection interface 1040 in the region of the coupling chamber 1024. The connection interface 1040 can be configured to complementarily engage a connection interface 1042 of the cap 1004. For example, in the illustrated embodiment, the connection interface 1040 of the cap 1002 comprises inwardly projecting threads 1041, and the connection interface 1042 of the connector 1004 comprises outwardly projecting threads 1043 complementary thereto at an exterior surface of the cap 1004. The connection interfaces 1040, 1042 thus can allow the caps 1002, 1004 to be coupled to each other in a secure, yet selectively removable fashion. Other configurations of the connection interfaces 1040, 1042 may similarly permit the caps 1002, 1004 to be coupled with each other in a secure, yet selectively removable fashion, such as friction-fit, snap-fit, or other suitable interfacing arrangements, as discussed further below. The coupling chamber 1024 can further include a sealing member 1044, such as an elastomeric gasket described further below.

With reference to FIGS. 10 and 11, the male cap 1004 can comprise a housing 1050. The housing 1050 can be elongated, and may define a stepped, substantially cylindrical shape, or may define any other suitable shape. For example, in the illustrated embodiment, the housing 1050 includes a sidewall 1052, which is substantially cylindrical, and a base wall 1054 at one end of the sidewall 1052. A sealing end 1056 of the sidewall 1052 can be located opposite the base wall 1054, and can define an opening into a disinfection chamber 1058. The sidewall 1052 and the base wall 1054 thus can cooperate to define the disinfection chamber 1058.

In some embodiments, the housing 1050 includes a skirt 1060, which can extend radially outwardly from the sidewall 1052. In some embodiments, the skirt 1060 provides a convenient surface for manipulation of the cap 1004. For example, in some embodiments, an outer diameter of the sidewall 1052 is smaller than an outer diameter of the sidewall 1012 of the cap 1002 such that the disparity between the outer diameters could complicate the gripping and rotation of the caps 1002, 1004 relative to each other. Moreover, in some embodiments, the sidewall 1052 defines a relatively small outer surface area, which could make it difficult to grip the cap 1004. The larger outer diameter and corresponding larger surface area of the skirt can facilitate gripping of the cap 1004. The outer surface of the skirt 1060 can be smooth, as shown, or may include gripping features, which can aid in rotating the cap 1004 relative to the cap 1002 to permit separation of the caps 1002, 1004 and/or aid in rotating the cap 1004 relative to a medical connector. Such gripping features can include, for example, ridges, grooves, and/or protrusions similar to the ridges 105, grooves 107, and protrusions 108 described above and/or an elastomeric or other coating having a relatively high coefficient of friction.

In some embodiments, a terminal edge 1062 of the skirt 1060 can be substantially coplanar with an outer surface of the base wall 1054. In certain of such embodiments, the skirt 1060 can increase the stability of the assembly 1000. For example, the assembly 1000 can stand uprightly on the base wall 1054, and the skirt 1060 can inhibit tipping of the assembly 1000.

With reference to FIG. 10, the disinfection chamber 1058 can include a pad 1070 such as the pad 1032. The pad 1070 can be deformable, so as to conform to the contours of a portion of a medical connector that is introduced into the disinfection chamber 1058 (e.g., an outer surface of a male luer). Compression and/or decompression of the pad 1070 can cause an antiseptic 1033 to exit from and/or be absorbed by the pad 1070, respectively, in a manner such as described above with respect to the pad 1032 (it is noted that the antiseptic 1033 used with the pad 1070 need not necessarily be the same antiseptic as that used with the pad 1032, although such is possible). Likewise, scrubbing or sanitization of a medical connector via the pad 1070 can proceed in a manner such as that described above with respect to the pad 1032. In the illustrated embodiment, the pad 1070 is in a relaxed or uncompressed state in at least a longitudinal direction when the disinfection chamber 1058 is in a sealed or pre-use configuration.

As previously discussed, the cap 1004 can include the connection interface 1042, which can interact with the connection interface 1040 of the cap 1002. The connection interfaces 1040, 1042 can cooperate to hold the cap 1004 tightly against the sealing member 1044. For example, where the connection interfaces 1040, 1042 comprise threading, appropriate rotation of the cap 1004 relative to the cap 1002 can draw the sealing end 1056 of the sidewall 1052 into abutment with the sealing member 1044, and additional rotation in the same direction may deform the sealing member 1044. The sealing end 1056 and the sealing member 1044 can form a hermetic seal that can assist in maintaining the sterility of the disinfection chamber 1058 prior to use of the cap 1004, and can prevent evaporative loss of an antiseptic from the disinfection chamber 1058. In further embodiments, a sealing tape (not shown), such as the sealing tape 158 (see FIGS. 8A and 8B), can be positioned about the caps 1002, 1004 so as to contact a lower edge of the housing 1010 (e.g., an outer surface of the portion of the sidewall 1012 that defines the coupling chamber 1058) and an outer surface of the skirt 1060 of the housing 1050. The tape can aid in preventing evaporative loss of the antiseptic and/or can indicate whether the caps 1002, 1004 have been separated or otherwise moved from their initial or pre-use configuration. For example, in some embodiments, the tape can be frangible.

In the illustrated embodiment, the connection interface 1042 comprises outwardly projecting threads similar to the threads 114 described above, and can be configured to complementarily engage a connection interface of a medical connector, such as, for example, inwardly projecting threads of a skirt that surrounds a male luer. The threaded connection interface 1042 thus can allow for selective coupling of the cap 1004 to a medical connector in a secure, yet selectively removable fashion. Other configurations of the connection interface 1042 may permit the cap 1004 to be coupled with a medical connector in a secure, yet selectively removable fashion, such as friction-fit, snap-fit, or other suitable interfacing arrangements.

With continued reference to FIG. 10, additional description of the illustrated embodiment of the assembly 1000 in the pre-use state will now be provided. As previously discussed, each disinfection chamber 1022, 1058 can be defined by a separate housing 1012, 1050. The chambers 1022, 1058 can be isolated from each other in the pre-use condition, or stated otherwise, no fluid communication may exist between the chambers 1022, 1058.

The caps 1002, 1004 can cooperate to seal one of the chambers (e.g., the chamber 1058 in the illustrated embodiment) such that manipulation of the caps 1002, 1004 away from their pre-use configuration can unseal the chamber 1058, whereas the other chamber (e.g., the chamber 1022 in the illustrated embodiment) can remain in a sealed orientation independent of the relative orientations of the caps 1002, 1004. At least a portion of the housing 1050 of the cap 1004 can be received within, or can nest within, a portion of the housing 1010 of the cap 1002. In the illustrated embodiment, the pad 1032 is free of any compression from the cap 1004 and the pad 1070 is free of any compression from the cap 1002 when the disinfection chambers 1022, 1058, in which the pads 1032, 1070 are housed, are in a pre-use, sealed condition.

In the illustrated embodiment, the caps 1002, 1004 are substantially coaxial with each other. As previously discussed, the disinfection chambers 1022, 1058 defined by the caps 1002, 1004 each can have an open end and a closed end, and in the pre-use configuration, the chambers 1022, 1058 can be oriented such that their sealed open ends face in the same direction along the common axis of the caps 1002, 1004.

With reference to FIG. 11, in order to prepare the cap 1004 for use with a medical connector (e.g., the connector 136 of FIG. 5), the caps 1002, 1004 are decoupled from each other. For example, in the illustrated embodiment, the caps 1002, 1004 are rotated in opposite directions about a common longitudinal axis such that the connection interfaces 1040, 1042 urge the caps 1002, 1004 away from each other and are eventually released from each other. The cap 1004 can then be coupled with the medical connector via the connection interface 1042, such as in a secure, yet selectively removable manner.

The cap 1002 can be prepared for use with a medical connector (e.g., the connector 132 of FIG. 4) and connected to the medical connector independent of the coupling status of the caps 1002, 1004 relative to each other. The cover 1034 can be removed from the cap 1002, thereby permitting the cap 1002 to be coupled with the medical connector via the connection interface 1040, such as in a secure, yet selectively removable manner.

The pre-use configuration of the system 1000, in which the caps 1002, 1004 are coupled with each other, can ease clinician handling of the system 1000. As the caps 1002, 1004 may be used to cover female and male connectors, respectively, immediately upon decoupling of the female and male connectors from each other, having the caps 1002, 1004 available in a coupled yet easily separable configuration can be convenient and time saving. Moreover, the system 1000 can include relatively few parts, which can reduce manufacturing costs. In some embodiments, the pre-use coupled configuration of the caps 1002, 1004 likewise can reduce packaging costs of the system 1000.

FIG. 12 illustrates another embodiment of an assembly 1100, which can resemble the assembly 1000 described above in certain respects. Accordingly, like features are designated with like reference numerals, with the leading digits incremented to "11." Relevant disclosure set forth above regarding similarly identified features thus may not be repeated hereafter. Moreover, specific features of the assembly 1100 may not be identified by a reference numeral in the drawings or specifically discussed in the written description that follows. However, such features may clearly be the same, or substantially the same, as features depicted in other embodiments and described with respect to such embodiments. Accordingly, the relevant descriptions of such features apply equally to the features of the assembly 1100. Any suitable combination of the features and variations of the same described with respect to the assembly 1000 and components thereof can be employed with the assembly 1100 and components thereof, and vice versa. This pattern of disclosure applies equally to further embodiments depicted in subsequent figures and described hereafter.

As with the assembly 1000, the assembly 1100 can include a female cap 1102 and a male cap 1104 that are coupled with each other when in a pre-use state and that can be removed from each other. The cap female 1102 can be configured to couple with a female connector, and the male cap 1104 can be configured to couple with a male connector. The female cap 1102 can include a housing 1110, which can include a sidewall 1112 and a partition 1120. A portion of the sidewall 1112 can cooperate with the partition 1120 to define a disinfection chamber 1122 such as the disinfection chamber 1022. In the illustrated embodiment, the disinfection chamber 1122 is somewhat shorter than the disinfection chamber 1022 (see FIG. 10). The disinfection chamber 1122 can include a connection interface 1130, which, in the illustrated embodiment, includes threading 1131. The disinfection chamber 1122 can include a pad 1132, such as the pad 1032, and can be sealed via a removable cover 1134.

Another portion of the sidewall 1112 can cooperate with the partition 1120 to define a coupling chamber 1124 that extends in a direction opposite the disinfection chamber 1122. A terminal edge 1118 of the sidewall 1112 can define an opening of the disinfection chamber 1122. The sidewall 1112 can define a connection interface 1140 that is configured to aid in coupling the caps 1102, 1104 with each other, as described further below.

With continued reference to FIG. 12, the cap 1104 can include a housing 1150 that includes a sidewall 1152 and a base wall 1154. The sidewall 1152 and the base wall 1154 can cooperate to define a disinfection chamber 1158, which can include a pad 1170 therein. The disinfection chamber 1158 can be sealed at a sealing end 1156 of the sidewall 1152 via a removable cover 1136, which can resemble the cover 1134. A portion of the sidewall 1152 can define a connection interface 1142, which includes one or more threads 1143 in the illustrated embodiment.

The housing 1150 can define a skirt 1160 that projects radially outwardly from the sidewall 1152. The skirt 1160 can terminate at a terminal edge 1162. In the illustrated embodiment, the skirt 1160 is shorter than the skirt 1060 of the housing 1050 (see FIG. 10) and is spaced above a plane that is defined by an outer surface of the base wall 1154. In some embodiments, the terminal edge 1162 contacts or is in close proximity to the terminal edge 1118 of the housing 1110 when the caps 1102, 1104 are coupled with each other in a pre-use configuration, which can provide continuity to an outer surface of the assembly 1100 when it is in a pre-use configuration. The skirt 1160 can be rounded or beveled at the terminal edge 1162, and an end of the sidewall 1112 can be rounded or beveled at the terminal edge 1118, which can provide the system 1100 with an annular recess 1163 that can provide a visual and/or tactile indication of the transition from the skirt 1160 to the sidewall 1112. The rounded ends can also enhance practitioner and/or patient comfort during use of the caps 1102, 1104.

In the illustrated embodiment, the sidewall 1152 of the housing 1150 defines a connection interface 1180 that is configured to couple with the connection interface 1140 of the housing 1110. In particular, the connection interface 1180 includes an outward projection 1181 and the connection interface 1140 includes a recess 1144 that extends radially outwardly relative to the connection chamber 1124 and that is sized to receive the annular projection 1181 therein in a snap-fit engagement. In the illustrated embodiment, each of the projection 1181 and the recess 1144 is annular and extends about the cap 1104 and the cap 1102, respectively, in its entirety. In other embodiments, the projection 1181 and/or the recess 1144 extend about only a portion of the caps 1102, 1104. In still other or further embodiments, the connection interface 1180 can include a recess in the sidewall 1152 and the connection interface 1140 can include an inward projection sized to fit within the recess in a snap-fit engagement. In still other or further embodiments, the connection interfaces 1140, 1180 can include complementary threading, such as the connection interfaces 1040, 1042 described above. Other coupling arrangements are also possible.

Features, usage, and operation of the assembly 1100 can resemble that of the assembly 1000 described above. For example, when the assembly 1100 is in the pre-use condition, each disinfection chamber 1122, 1158 can be defined by a separate housing 1112, 1150, and the disinfection chambers 1122, 1158 can be fluidly isolated from one another (e.g., no fluid communication may exist between the disinfection chambers 1122, 1158). Likewise, at least a portion of the housing 1150 of the cap 1104 can be received within, or can nest within, a portion of the housing 1110 of the cap 1102. In the illustrated embodiment, each of the pads 1132, 1170 is in an uncompressed or expanded state when each of the disinfection chambers 1122, 1158 in which it is housed is in a pre-use, sealed condition.

However, certain differences can exist between the assembly 1100 and the assembly 1000. For example, each of the disinfection chambers 1122, 1158 can remain sealed independent of the coupling status of the caps 1102, 1104. Stated otherwise, the caps 1102, 1104 do not cooperate to seal either of the chambers 1122, 1158. Accordingly, one or both of the caps 1102, 1104 can be unsealed (e.g., the covers 1134, 1136 can be removed) and coupled with a separate medical connector (e.g., via the connection interfaces 1130, 1142) without detaching the caps 1102, 1104 from each other. Stated in yet another manner, either of the caps 1102, 1104 can be installed on a medical connector without being detached from and/or without unsealing the other cap 1102, 1104. Alternatively, the caps 1102, 1104 can be detached from each other, one or both of the caps 1102, 1104 each can be connected with a separate medical connector (i.e., via the connection interfaces 1130, 1142), and the caps 1102, 1104 can be reattached to each other (i.e., via the connection interfaces 1140, 1180), while remaining connected to the one or more medical connectors.

Moreover, in the illustrated embodiment, the caps 1102, 1104 are substantially coaxial with each other, thus resembling the caps 1002, 1004. However, the disinfection chambers 1122, 1158 are oriented such that their sealed open ends face away from each other (e.g., outwardly in opposite directions) along the common axis of the caps 1102, 1104, when the assembly 1100 is in the pre-use configuration.

FIG. 13 illustrates another embodiment of an assembly 1200, which can resemble one or more of the assemblies described above in certain respects. Accordingly, like features are designated with like reference numerals, with the leading digits incremented to "12." As with the assembly 1100, the assembly 1200 can include a cap 1202 and cap 1204 that are coupled with each other, when in a pre-use state, and that can be removed from each other.

The caps 1202, 1204 can differ from the caps 1102, 1104 in the manner by which they are coupled with each other. In particular, the cap 1202 includes a housing 1210 that defines a connection chamber 1224 configured to receive a portion of a housing 1250 of the cap 1204. The housing 1210 defines a connection interface 1240, and the housing 1250 defines a connection interface 1280. Rather than cooperating in a snap-fit engagement, however, the connection interfaces 1240, 1280 cooperate with each other in a friction-fit engagement to provide a secure attachment between the caps 1202, 1204 and yet to permit the caps 1202, 1204 to be selectively removable from each other and to permit selective reattachment of the caps 1202, 1204 to each other. Features, usage, and operation of the assembly 1200 can otherwise resemble that of the assembly 1100 described above.

Figure 15:
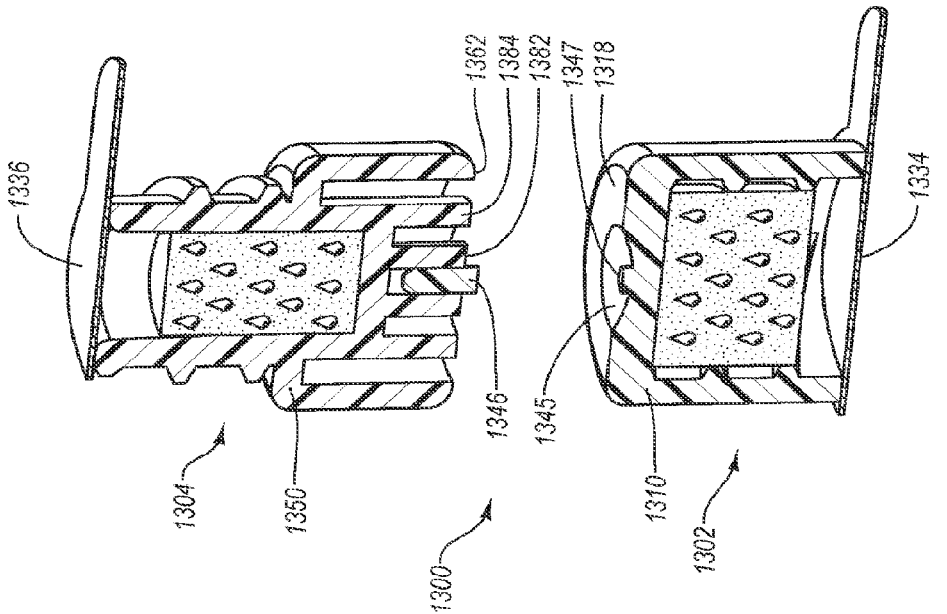
FIG. 15 is a cross-sectional perspective view of the assembly of FIG. 14 showing the caps detached from each other.
Figure 14:
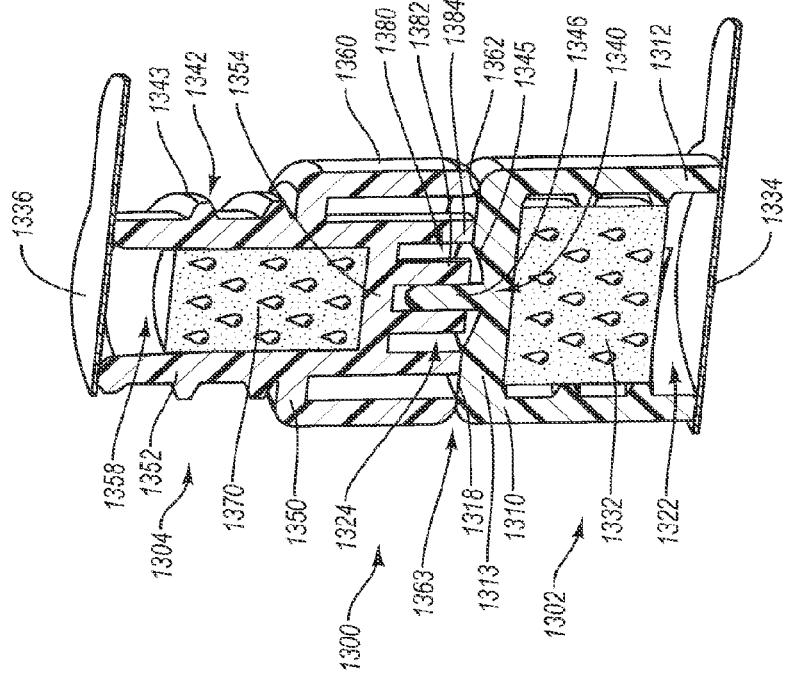
FIG. 14 is a cross-sectional perspective view of another embodiment of an assembly that includes a pair of caps, which are attached to each other via a press-fit interface.

FIGS. 14 and 15 illustrate another embodiment of an assembly 1300, which can resemble one or more of the assemblies described above in certain respects. Accordingly, like features are designated with like reference numerals, with the leading digits incremented to "13." The assembly 1300 can include a cap 1302 and cap 1304 that are coupled with each other when in a pre-use state and that can be removed from each other. However, as discussed further below, the caps 1302, 1304 can include connection interfaces 1340, 1380, respectively, that attach the caps 1302, 1304 to each other in a pre-use configuration, and that permit ready detachment of the caps 1302, 1304 one from another, but that do not themselves permit reattachment of the caps 1302, 1304.

The cap 1302 can include a housing 1310, which can include a sidewall 1312 and a base wall 1313. The sidewall 1312 and the base wall 1313 can cooperate to define a disinfection chamber 1322 that can include a pad 1332 therein and that can be sealed via a removable cover 1334. The base wall 1313 can include a terminal surface 1318 and can define the connection interface 1340. In the illustrated embodiment, the connection interface 1340 includes a depression or recess 1345 that bows the terminal surface 1318 inwardly, or toward the disinfection chamber 1322. The connection interface 1340 further includes a pin 1346 that extends outwardly, or away from the disinfection chamber 1322.

With continued reference to FIGS. 14 and 15, the cap 1304 can include a housing 1350 that includes a sidewall 1352 and a base wall 1354. The sidewall 1352 and the base wall 1354 can cooperate to define a disinfection chamber 1358, which can include a pad 1370 therein. The disinfection chamber 1358 can be sealed via a removable cover 1336. A portion of the sidewall 1352 can define a connection interface 1342, which includes one or more threads 1343 in the illustrated embodiment.

The housing 1350 can define a skirt 1360 that projects radially outwardly from the sidewall 1352. The skirt 1360 can terminate at a terminal edge 1362. In the illustrated embodiment, the skirt 1360 extends past a plane that is defined by an outer surface of the base wall 1354 and is sufficiently long to permit the terminal edge 1362 thereof to contact the terminal surface 1318 of the housing 1310 when the caps 1302, 1304 are in a pre-use configuration. As with the skirt 1160 and the sidewall 1112, the skirt 1360 can be rounded or beveled at its terminal edge 1362, and the sidewall 1112 can be rounded or beveled at the terminal surface 1118, which can provide the system 1300 with an annular recess 1363.

The housing 1350 defines the connection interface 1380, which is configured to couple with the connection interface 1340 of the housing 1310. The connection interface 1380 includes a protrusion 1382 that extends from the base wall 1354 in a direction opposite the disinfection chamber 1358. The protrusion 1382 is sized and shaped to receive therein at least a portion of the pin 1346, and may be substantially annular. In various embodiments, the protrusion 1382 is joined to the pin in any suitable manner, such as, for example, press-fit or friction-fit engagement and/or any suitable adhesive.

In the illustrated embodiment, an additional protrusion 1384 is coaxial with and encircles the protrusion 1382, and may also be substantially annular. The protrusion 1384 can contact the terminal surface 1318 of the housing 1310 when the caps 1302, 1304 are in a pre-use configuration, and can provide stability to the connection interfaces 1340, 1380 and assist in preventing premature separation of the caps 1302, 1304. The protrusion 1384 can be said to define a connection chamber 1324 in which the connection interface 1380 is located.

As shown in FIG. 15, the caps 1302, 1304 can be separated from each other, which can facilitate coupling of the caps 1302, 1304 to separate medical connectors by removing a constraint on the range of motion of the caps 1302, 1304 relative to each other. In the illustrated embodiment, the pin 1346 can be sufficiently thin, sufficiently weak, or otherwise configured to break away from the housing 1310, and can remain attached to the protrusion 1382 of the housing 1350. In various embodiments, in order to break the pin 1346, a practitioner can rotate the caps 1302, 1304 relative to each other about their common longitudinal axis and/or can rotate one or more of the caps 1302, 1304 about an axis perpendicular to its longitudinal axis so as to move the longitudinal axes of the caps 1302, 1304 out of alignment with each other.

Breaking the pin 1346 can leave a nub 1347 on the housing 1310. In certain embodiments, the nub 1347 can be fully below the terminal surface 1318 of the housing 1310 due to the recess 1345, which can prevent or reduce contact with the nub 1347, such as by a patient or practitioner.

In certain embodiments, the connection interfaces 1340, 1380 are configured so as to not rejoin with each other once the caps 1302, 1304 have been separated from the pre-use configuration. For example, once the pin 1346 has been broken, the caps 1302, 1304 cannot readily be rejoined to each other via the pin 1346. Accordingly, the caps 1302, 1304 can be configured to be attached with each other in a pre-use configuration and readily separated from each other as desired, but not readily rejoined with each other once separated.

Features, usage, and operation of the assembly 1300 can resemble those of one or more of the assemblies described above in other respects. For example, when the assembly 1300 is in the pre-use condition, each disinfection chamber 1322, 1358 can be defined by a separate housing 1312, 1350, and the disinfection chambers 1322, 1358 can be fluidly isolated from one another. Likewise, at least a portion of one of the housings 1310, 1350 can be received within, or can nest within, a portion of the other housing 1310, 1350. To this end, it is noted that in other embodiments of the assembly 1300, the housing 1350 of the cap 1304 may define the pin 1346 (or, more generally, the connection interface 1340), and the housing 1310 of the cap 1302 may define the annular extension 1382 (or, more generally, the connection interface 1380). In the illustrated embodiment, each of the pads 1332, 1370 is in an uncompressed or expanded state when the disinfection chamber 1322, 1358 in which it is housed is in a pre-use, sealed condition. Like the assemblies 1100, 1200, each of the disinfection chambers 1322, 1358 can remain sealed independent of the coupling status of the caps 1302, 1304. One or both of the disinfection chambers 1322, 1358 can be opened and used, while the caps 1302, 1304 are connected with each other, or the caps 1302, 1304 can be separated from each other and one or both of the disinfection chambers 1322, 1358 can then be opened and each used with a separate medical connector.

Figure 17:
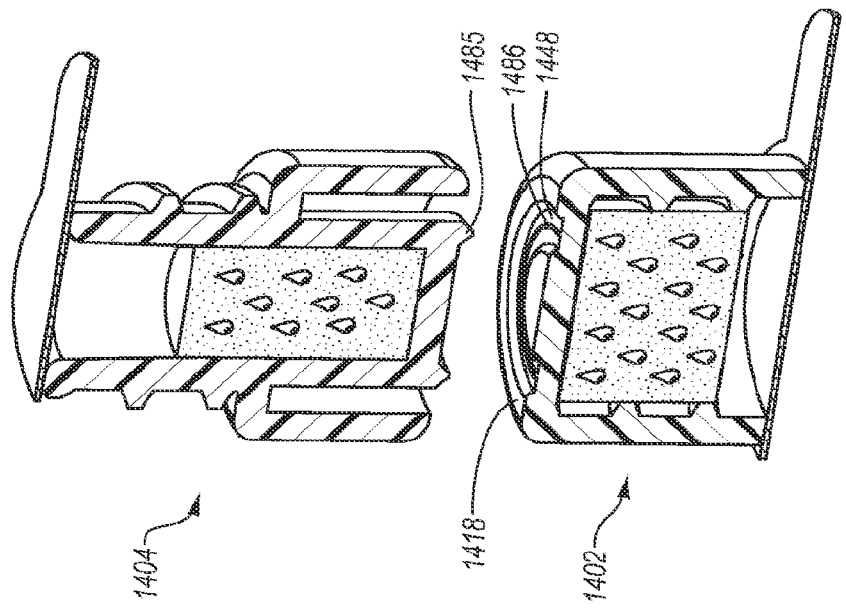
FIG. 17 is a cross-sectional perspective view of the assembly of FIG. 16 showing the caps detached from each other.
Figure 16:
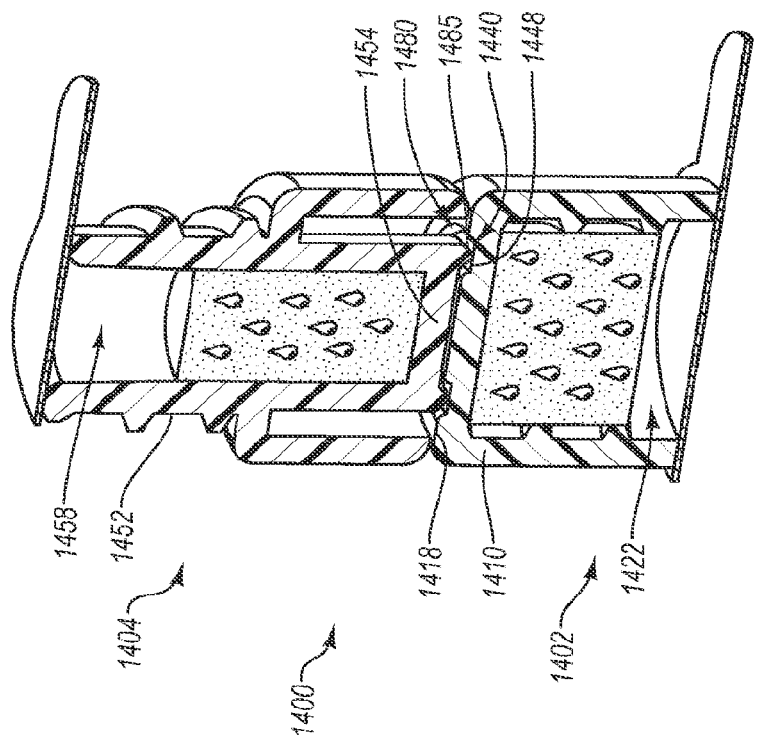
FIG. 16 is a cross-sectional perspective view of another embodiment of an assembly that includes a pair of caps, which are attached to each other via a welded interface.

FIGS. 16 and 17 illustrate another embodiment of an assembly 1400, which can resemble the assembly 1300 described above in certain respects. Accordingly, like features are designated with like reference numerals, with the leading digits incremented to "14." The assembly 1400 can include a cap 1402 and cap 1404 that are coupled with each other when in a pre-use state, and that can be removed from each other in a manner similar to the caps 1302, 1304. However, connection interfaces 1440, 1480 of the caps differ from the connection interfaces 1340, 1380 of the caps 1302, 1304.

The connection interface 1440 can be defined by a terminal surface 1418 of a housing 1410 of the cap 1402. The connection interface 1440 can include a depression or recess 1448 that bows the terminal surface 1418 inwardly, or toward a disinfection chamber 1422. The recess 1448 can be annular, although other shapes and configurations are possible.

A sidewall 1452 of the cap 1404 can be somewhat longer than the sidewall 1352 of the cap 1304, and a base wall 1454 of the cap 1404 can be in close proximity with or adjacent to the terminal surface 1418 of the cap 1402. A protrusion 1485 can extend outwardly from the base wall 1454, or in a direction away from a disinfection chamber 1458. The protrusion 1485 can be annular so as to be received within the annular recess 1448, although other shapes and configurations are possible. The protrusion 1485 can be joined to the recess 1448 in any suitable manner, such as via an adhesive or via welding (e.g., spin, ultra-sonic, laser, radio frequency, thermal, etc.).

In the illustrated embodiment, the protrusion 1485 is welded to the recess 1448, and the weld is configured to be broken to permit separation of the caps 1402, 1404. As shown in FIG. 17, a weld edge 1486 can remain within the recess 1448 when the caps 1402, 1404 are separated. In certain embodiments, the weld edge 1486 can be fully below the terminal surface 1418 of the housing 1410, which can prevent or reduce contact with the weld edge 1486, such as by a patient or practitioner. In order to break the weld, a practitioner can rotate the caps 1402, 1404 relative to each other about their common longitudinal axis and/or can rotate one or more of the caps 1402, 1404 about an axis perpendicular to its longitudinal axis, so as to move the longitudinal axes of the caps 1402, 1404 out of alignment with each other. In other embodiments, the connection interfaces 1440, 1480 can be reversed such that the cap 1402 includes the protrusion 1485 and the cap 1404 can includes the recess 1448.

Figure 18:
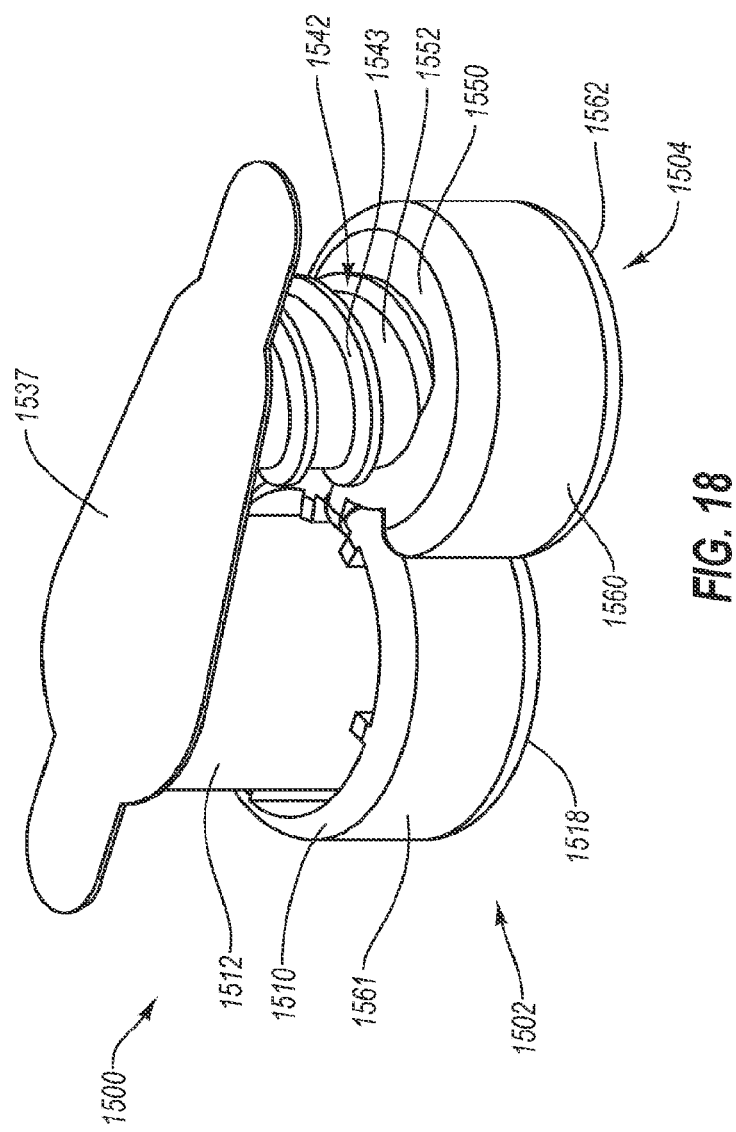
FIG. 18 is a perspective view of another embodiment of an assembly that includes a pair of caps, which are attached to each other at least partially via a snapping interface.
Figure 19:
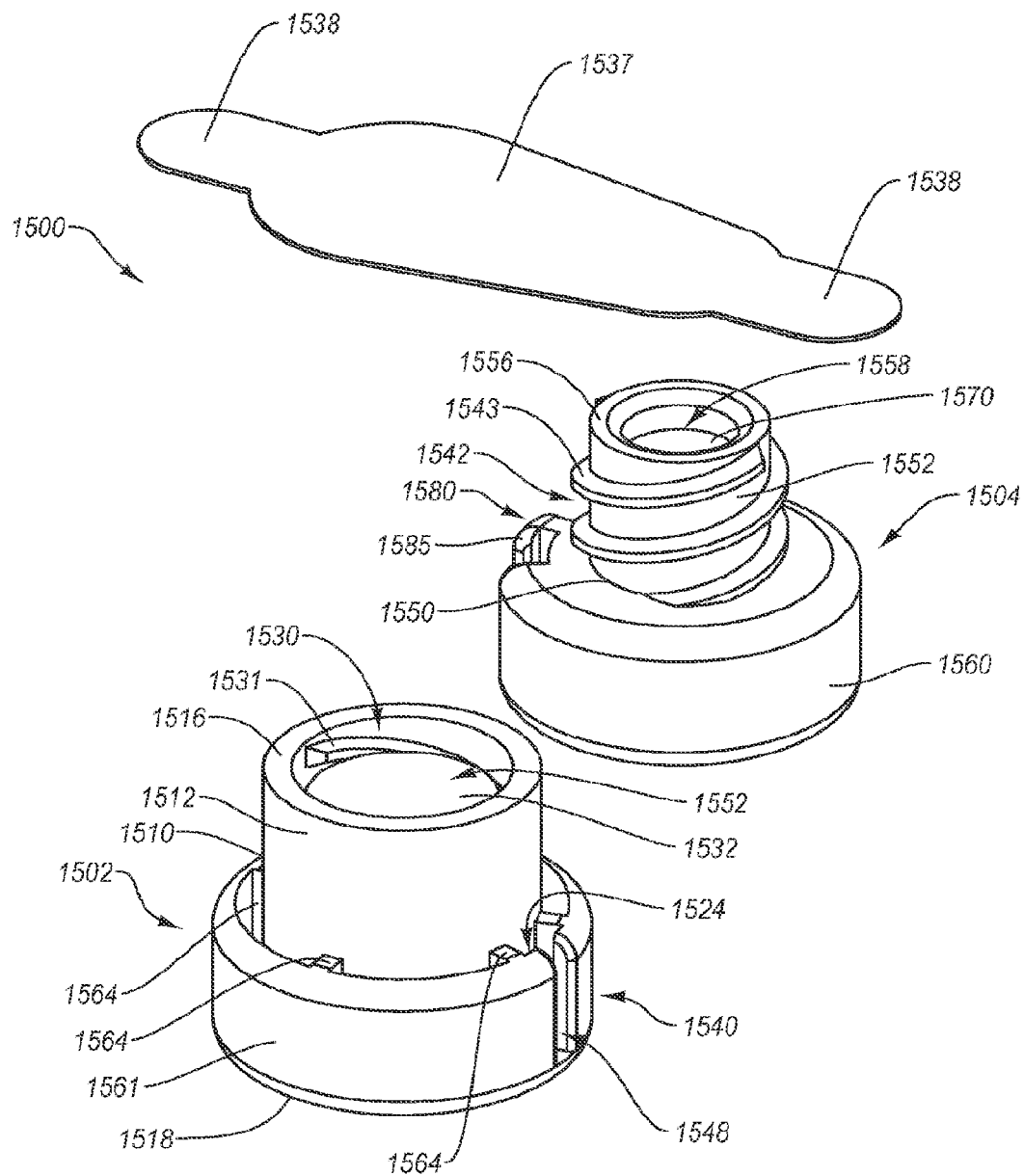
FIG. 19 is a perspective view of the assembly of FIG. 18 showing the caps detached from each other.

FIGS. 18-21 illustrate another embodiment of an assembly 1500, which can resemble one or more of the assemblies described above in certain respects. Accordingly, like features are designated with like reference numerals, with the leading digits incremented to "15." As can be seen in FIGS. 18 and 19, and as discussed hereafter, the assembly 1500 can include a cap 1502 and cap 1504 that are coupled with each other when in a pre-use state and that can be removed from each other. The cap 1502 can be configured to couple with a female connector, and the cap 1504 can be configured to couple with a male connector. The caps 1502, 1504 can be in a side-by-side arrangement when connected to each other in a pre-use configuration. In the illustrated embodiment, both caps 1502, 1504 can be sealed shut in the pre-use configuration via a common cover 1537.

The cap 1502 can include a housing 1510, which can include a sidewall 1512 and a base wall 1513. The sidewall 1512 can cooperate with the base wall 1513 to define a disinfection chamber 1522. The disinfection chamber 1522 can include a connection interface 1530, which, in the illustrated embodiment, includes threading 1531 disposed on an interior surface of the housing 1512. The connection interface 1530 can be configured to attach the cap 1502 to a medical connector in a secure yet selectively removable manner. The disinfection chamber 1522 can include a pad 1532.

Figure 21:
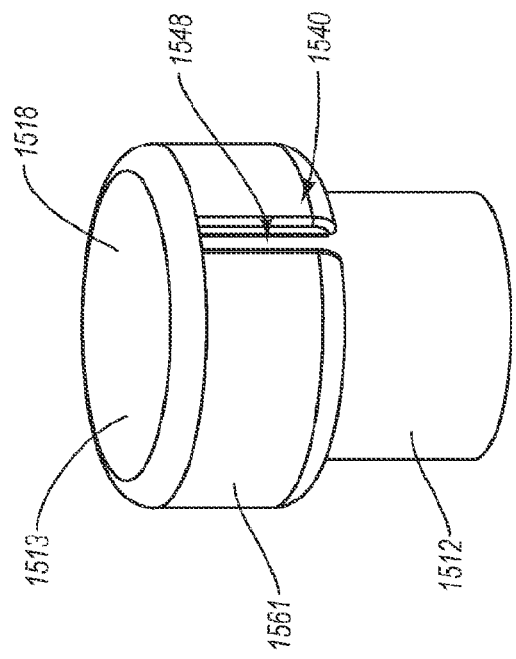
FIG. 21 is a perspective view from a different angle of another of the caps of FIG. 18.

The housing 1510 can further include a skirt 1561 that projects radially outwardly from the sidewall 1512 and that can also extend substantially parallel to the sidewall 1512. The skirt 1561 can include one or more spacers or supports 1564 that can provide structural rigidity to the skirt 1561. As shown in FIGS. 19 and 21, the housing 1510 can define a connection interface 1540 that is configured to aid in coupling the caps 1502, 1504 with each other in a pre-use configuration, as discussed further below. The connection interface 1540 can include a slot 1548 defined by the skirt 1561, which can extend in a direction substantially parallel to a longitudinal axis of the disinfection chamber 1522. The sidewall 1512 and the skirt 1561 can cooperate to define an open connection chamber 1524, which is also discussed below. The slot 1548 can define a side opening of the connection chamber 1524.

Figure 20:
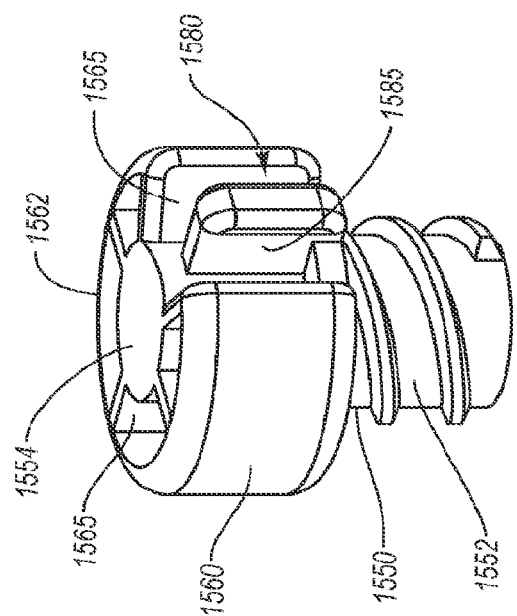
FIG. 20 is a perspective view from a different angle of one of the caps of FIG. 18.

With reference to FIGS. 19 and 20, the cap 1504 can include a housing 1550 that includes a sidewall 1552 and a base wall 1554. The sidewall 1552 and the base wall 1554 can cooperate to define a disinfection chamber 1558, which can include a pad 1570 therein. A portion of the sidewall 1552 can define a connection interface 1542, which includes one or more threads 1543 in the illustrated embodiment. The connection interface 1542 can be configured to attach the cap 1504 to a medical connector in a secure yet selectively removable manner. The housing 1550 can define a skirt 1560 that projects radially outwardly from the sidewall 1552 and that can also extend substantially parallel to the sidewall 1552. In the illustrated embodiment, the skirt 1560 extends about only a portion of the cap 1504. The skirt 1560 can include one or more spacers or supports 1565 that can provide structural rigidity to the skirt 1560.

The housing 1550 can further define a connection interface 1580 that is configured to interact with the connection interface 1540 of the housing 1510 to couple the caps 1502, 1504. The connection interfaces 1540 can maintain the caps 1502, 1504 in a pre-use configuration, and can permit the caps 1502, 1504 to be selectively removed from this configuration. In the illustrated embodiment, the connection interfaces 1540, 1580 can further interact with each other to permit selective reattachment of the caps 1502, 1504 to each other.

In the illustrated embodiment, the connection interface 1580 includes a locking member, snapping member, or radial extension 1585. The extension 1585 projects radially from the sidewall 1552 and includes an enlarged region at its outermost end. The extension 1585 is configured to be received within the slot 1548 and the connection chamber 1524 of the cap 1502. The enlarged portion of the extension 1585 can prevent the extension 1585 from moving out of the slot 1548 in a lateral direction. Although not shown, in some embodiments, the slot 1548 and the extension 1585 can include keying, such as a protrusion and recess that cooperate in a snapping fashion, which can selectively prevent the extension 1585 from moving out of the slot 1548 in a longitudinal direction in the absence of application of sufficient force by a practitioner. In other embodiments, the connection interfaces 1540, 1580 can be reversed such that the cap 1402 includes the extension 1585 and the cap 1504 includes the slot 1548.

In the illustrated embodiment, a terminal surface 1518 of the cap 1502 and a terminal surface 1562 of the cap 1504 are substantially coplanar when the system 1500 is in the pre-use configuration. This can contribute to the stability of the pre-use system 1500, as the connected system 1500 can be set on a planar surface without a predisposition to tipping. Likewise, in the illustrated embodiment, a sealing end 1516 of the cap 1502 and a sealing end 1556 of the cap 1504 are substantially coplanar when the system 1500 is in the pre-use configuration. Each sealing end 1516, 1556 can be sealed closed via a single or common removable cover 1537. In the illustrated embodiment, the cover 1537 includes two tabs 1538 that can permit selective opening of just one of the caps 1502, 1504, or the opening both of the caps 1502, 1504 by beginning with opening one of the caps 1502, 1504 by removing a portion of the cover 1537 from that cap 1502, 1504 and then continuing to remove the cover 1537 from the remaining cap 1502, 1504. Other arrangements are also possible.

The cover 1537 can assist in maintaining the caps 1502, 1504 coupled with each other in the pre-use configuration, as it can be sufficiently tight to resist longitudinal movement of the caps 1502, 1504 relative to each other. In various embodiments, the cover 1537 is removed from one or both of the caps 1502, 1504 prior to removing the caps 1502, 1504 from each other, as shown in FIG. 19. In other embodiments, the connection interfaces 1540, 1580 of the caps 1502, 1504 can be decoupled from each other prior to removing the cover 1537.

Features, usage, and operation of the assembly 1500 can resemble that of one or more of the assemblies described above. For example, when the assembly 1500 is in the pre-use condition, each disinfection chamber 1522, 1558 can be defined by a separate housing 1512, 1550, and the disinfection chambers 1522, 1558 can be fluidly isolated from one another. Likewise, at least a portion of the housing 1550 of the cap 1504 can be received within, or can nest within, a portion of the housing 1510 of the cap 1502. In the illustrated embodiment, each of the pads 1532, 1570 is in an uncompressed or expanded state when the disinfection chamber 1522, 1558 in which it is housed is in a pre-use, sealed condition.

However, certain differences can exist. For example, in the illustrated embodiment, the caps 1502, 1504 are side-by-side, rather than coaxial, when in the pre-use configuration. Stated otherwise, each cap 1502, 1504 can define a longitudinal axis, and the longitudinal axes can be substantially parallel with each other or non-collinear relative to each other when the caps 1502, 1504 are in the pre-use configuration. In the illustrated embodiment, the disinfection chambers 1522, 1558 are oriented such that their sealed open ends face in substantially the same direction when the assembly 1500 is in the pre-use configuration.

FIG. 22 illustrates another embodiment of an assembly 1600, which can resemble one or more of the assemblies described above, particularly the assembly 1500, in certain respects. Accordingly, like features are designated with like reference numerals, with the leading digits incremented to "16." The assembly 1600 can include caps 1602, 1604 such as the caps 1502, 1504. Rather than including a single cover 1537, however, an individual cover 1634, 1636 is provided to each of the caps 1602, 1604. Such an arrangement can, in some instances, facilitate removal of the caps 1602, 1604 from each other while the caps 1602, 1604 are maintained in a sealed configuration.

Figure 24:
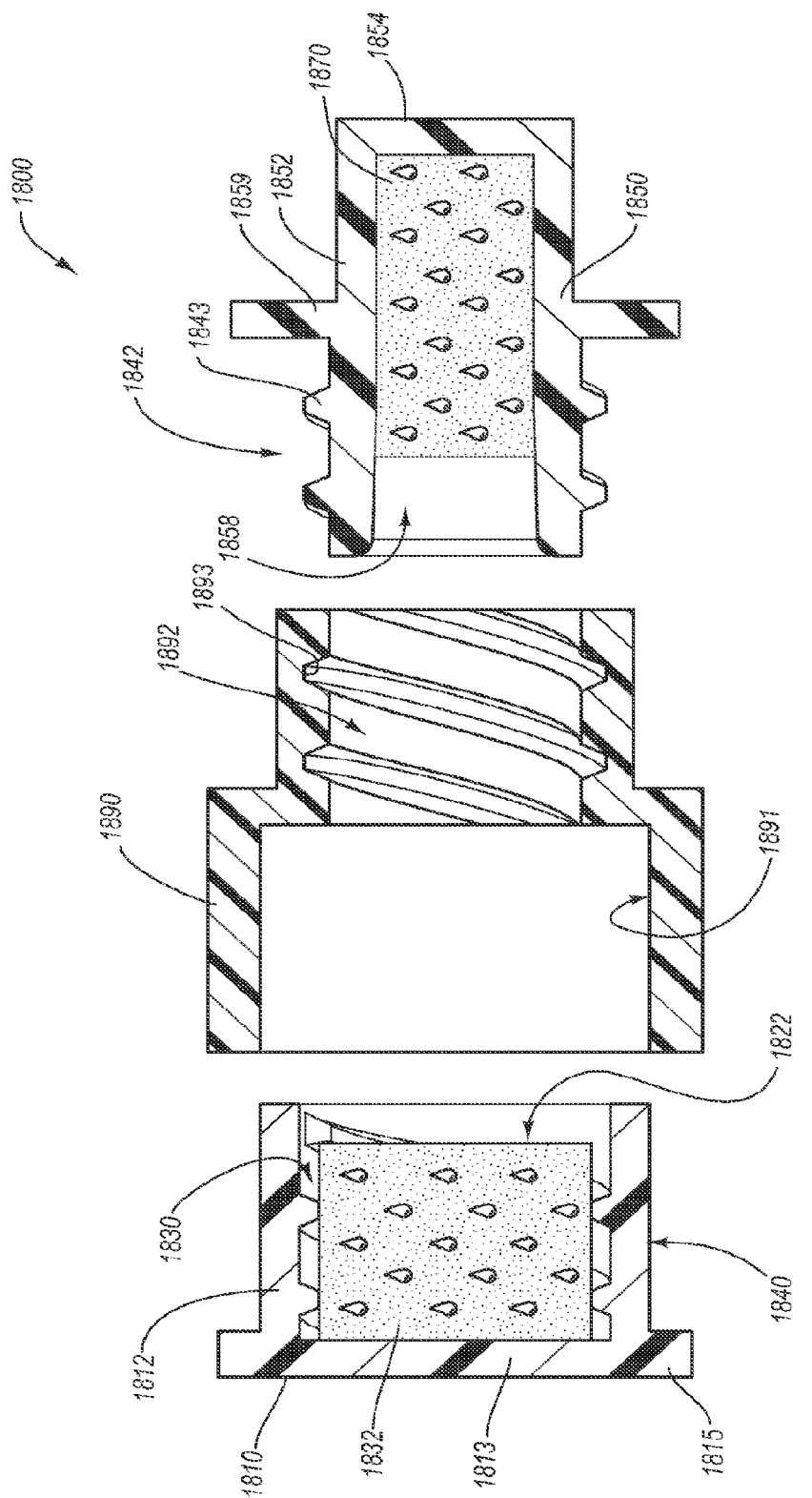
FIG. 24 is a cross-sectional view of the assembly of FIG. 23, wherein the caps are shown detached from the sleeve.
Figure 25:
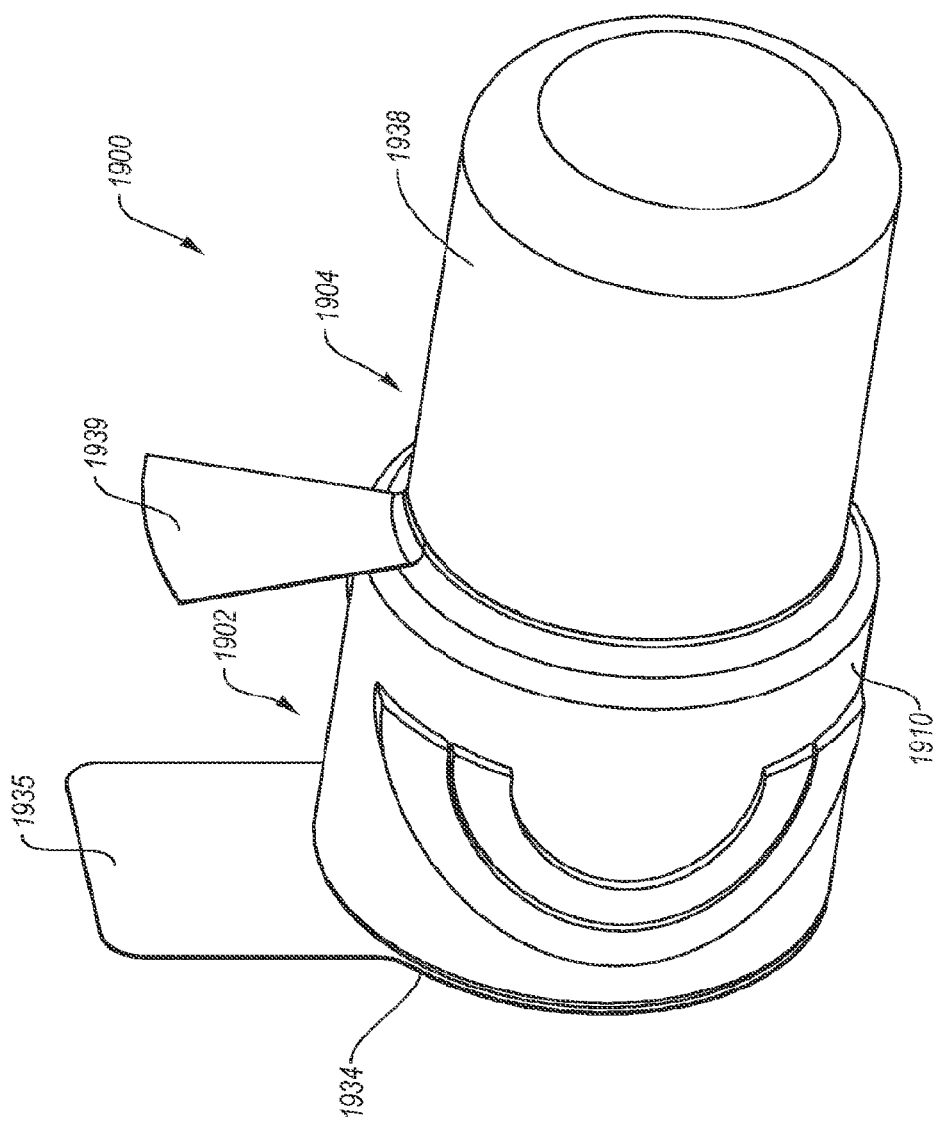
FIG. 25 is a perspective view of another embodiment of an assembly that includes two cap portions integrally connected to each other.

FIGS. 23 and 24 illustrate another embodiment of an assembly 1800, which can resemble one or more of the assemblies described above in certain respects. Accordingly, like features are designated with like reference numerals, with the leading digits incremented to "18." The assembly 1800 can include a cap 1802 and cap 1804 that are coupled with each other when in a pre-use state (FIG. 23) and that can be removed from each other (FIG. 24). In particular, the caps 1802, 1804 can be coupled with each other via a sealing mechanism. In the illustrated embodiment, the caps 1802, 1804 are coupled with each other via a sealing sleeve 1890. The caps 1802, 1804 can have open ends facing one another, and disinfection chambers 1822, 1858 of the caps 1802, 1804 can be in fluid communication with each other, when in the pre-use configuration.

The cap 1802 can include a housing 1810, which can include a sidewall 1812 and a base wall 1813. The sidewall 1812 can cooperate with the base wall 1813 to define the disinfection chamber 1822. The disinfection chamber 1822 can include a connection interface 1830, which, in the illustrated embodiment, includes threading 1831 disposed on an interior surface of the housing 1812. The connection interface 1830 can be configured to attach the cap 1802 to a medical connector in a secure yet selectively removable manner. The disinfection chamber 1822 can include a pad 1832.

An exterior surface of the sidewall 1812 can define a connection interface 1840 that is configured to couple the cap 1802 with a connection interface 1891 of the sleeve 1890. In the illustrated embodiment, the connection interfaces 1840, 1891 couple with each other via a friction-fit engagement. The friction fit can be sufficiently strong to provide a fluid-tight seal between the cap 1802 and the sleeve 1890, yet can allow the cap 1802 to be removed from the sleeve 1890 via mere manipulation by a medical practitioner (e.g., without the use of ancillary tools). The fluid-tight seal can prevent evaporative loss of antiseptic from the pad 1832 and/or can maintain the sterility of the disinfection chamber 1822. In other or further embodiments, the connection interfaces 1840, 1891 can include threading or other suitable attachment features.

In the illustrated embodiment, the base wall 1813 protrudes slightly beyond an end of the sleeve 1890, which can aid in manipulating the cap 1802 away from the sleeve 1890. In other embodiments, the base wall 1813 can protrude even further, or can include one or more protrusions or gripping features, that can aid in removing the cap 1802 from the sleeve 1890.

The cap 1802 can include a flange 1815 having an outer diameter larger than an inner diameter of the end of the sleeve 1890 that connects with the cap 1802. The flange 1815 can prevent the cap 1802 from being inserted into the sleeve 1890 too deeply. In other or further embodiments, the flange 1815 can cooperate with an end surface of the sleeve 1890 to create a fluid-tight seal. For example, in some embodiments, a sealing member, such as an O-ring, is included between the flange 1815 and the end of the sleeve 1890 to provide the fluid-tight seal.

The cap 1804 can include a housing 1850 that includes a sidewall 1852 and a base wall 1854. The sidewall 1852 and the base wall 1854 can cooperate to define a disinfection chamber 1858, which can include a pad 1870 therein. A portion of the sidewall 1852 can define a connection interface 1842, which includes one or more threads 1843 in the illustrated embodiment. The connection interface 1842 can be configured to attach the cap 1804 to a medical connector in a secure yet selectively removable manner. Additionally, the connection interface 1842 can cooperate with a connection interface 1892 defined by the sleeve 1890 to couple the cap 1804 with the cap 1802. The connection interface 1892 can include threading 1893 that is complementary to the threading 1843. The interfaces 1842, 1892, when coupled with each other, can provide a fluid-tight seal between the cap 1804 and the sleeve 1890. In other embodiments, the connection interfaces 1842, 1890 can instead define a friction-fit seal, such as that provided by the illustrated embodiment of the connection interfaces 1840, 1891 described above. In still other or further embodiments, a flange 1859 defined by the housing 1850 can cooperate with an end surface of the sleeve 1890 to create a fluid-tight seal, which can prevent evaporative loss of antiseptic from the pad 1870 and/or maintain the sterility of the disinfection chamber 1858. For example, in some embodiments, a sealing member, such as an O-ring, is included between the flange 1859 and the end of the sleeve 1890 to provide the fluid-tight seal.

Features, usage, and operation of the assembly 1800 can resemble that of one or more of the assemblies described above. For example, when the assembly 1800 is in the pre-use condition, each disinfection chamber 1822, 1858 can be defined by a separate housing 1812, 1850. Likewise, the caps 1802, 1804 can be coaxial with each other, and the open ends of the caps 1802, 1804 can face in opposite directions (e.g., towards each other). In the illustrated embodiment, each of the pads 1832, 1870 is in an uncompressed or expanded state when the disinfection chamber 1822, 1858 in which it is housed is in a pre-use, sealed condition.

However, certain differences can exist. For example, in the illustrated embodiment, the disinfection chambers 1822, 1858 are in fluid communication with each other when the caps 1802, 1804 are in the pre-use state. Moreover, in the illustrated embodiment, no portion of the housing 1850 of the cap 1804 is received within, or nested within, any portion of the housing 1810 of the cap 1802.

FIGS. 25-29 illustrate another embodiment of an assembly 1900, which can resemble one or more of the assemblies described above in certain respects. Accordingly, like features are designated with like reference numerals, with the leading digits incremented to "19." As shown, for example, FIGS. 25 and 26, the assembly 1900 can include a female cap portion or female cap 1902 and a male cap portion or male cap 1904 that are integrally formed or otherwise permanently attached with each other. For example, the caps 1902, 1904 can include a single, integrally molded housing 1910. The female cap 1902 can be configured to couple with a female connector, and the male cap 1904 can be configured to couple with a male connector. In the illustrated embodiment, the caps 1902, 1904 are in a coaxial arrangement. As shown, for example, in FIGS. 26 and 28, the assembly 1900 can include a pad 1970 that is received within one or more of the caps 1902, 1904. As shown, for example, in FIGS. 25 and 26, each cap 1902, 1904 can be sealed shut in the pre-use configuration via a separate cover 1934, 1938, respectively. Each cover 1934, 1938 can include a tab 1935, 1939, respectively, that can aid in removal of the cover.

Figure 29:
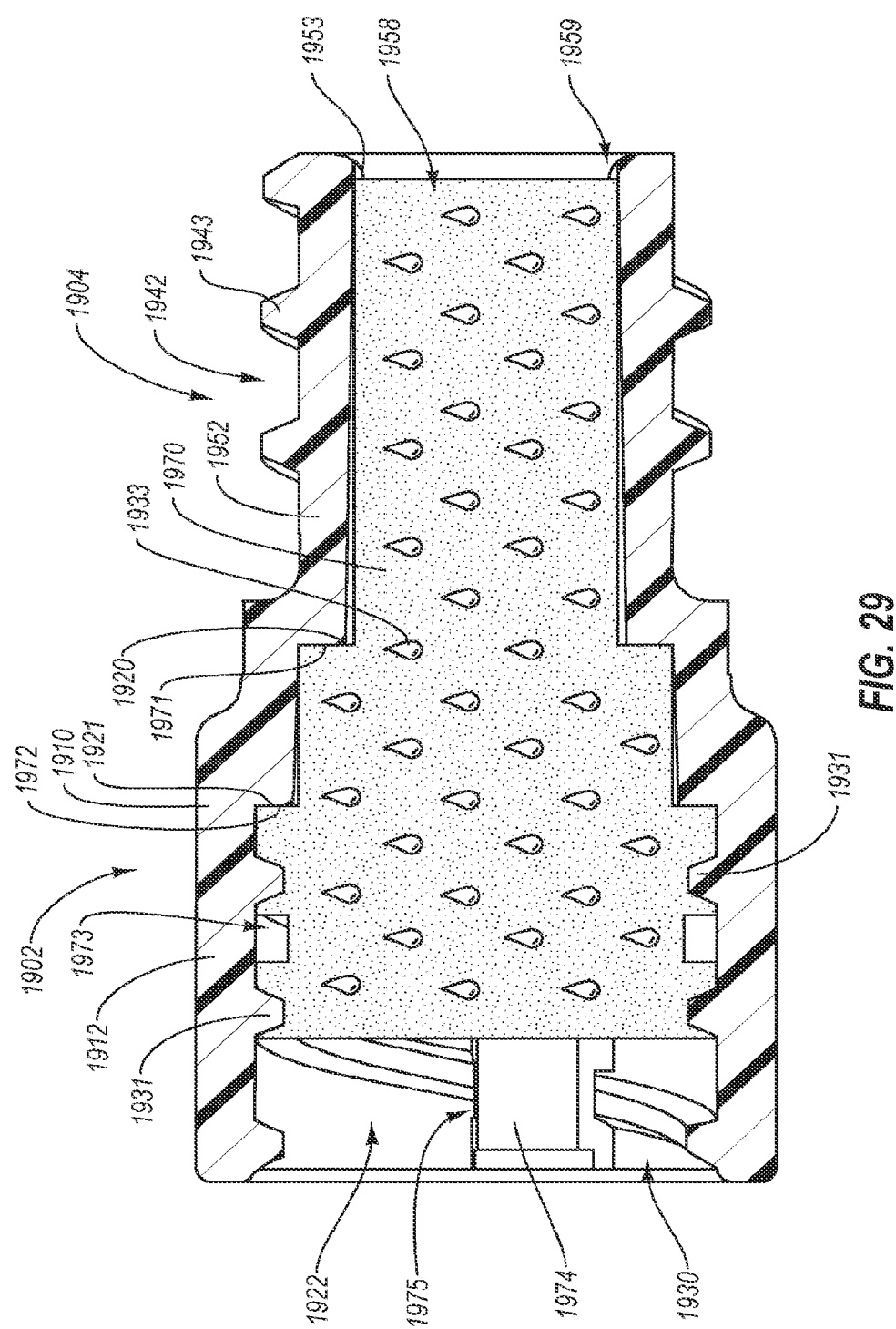
FIG. 29 is a cross-sectional view of the assembly of FIG. 28 taken along the view line 29-29.

With continued reference to FIGS. 25-29, the housing 1910 can define at least a portion of each of the caps 1902, 1904. The housing 1910 includes a first sidewall 1912 that defines a first disinfection chamber 1922 and includes a second sidewall 1952 that defines a second disinfection chamber 1958. As shown in FIG. 29, the first sidewall 1912 can define larger inner and outer diameters than those defined by the second sidewall 1952. The housing 1910 can transition from the first sidewall 1912 and the first disinfection chamber 1922 to the second sidewall 1952 and the second disinfection chamber 1958 at a constriction or abutment 1920. The housing 1910 can be substantially hollow such that the first and second disinfection chambers 1922, 1958 are in fluid communication with each other. The housing 1910 can define another abutment 1921, which is discussed further below.

Figure 26:
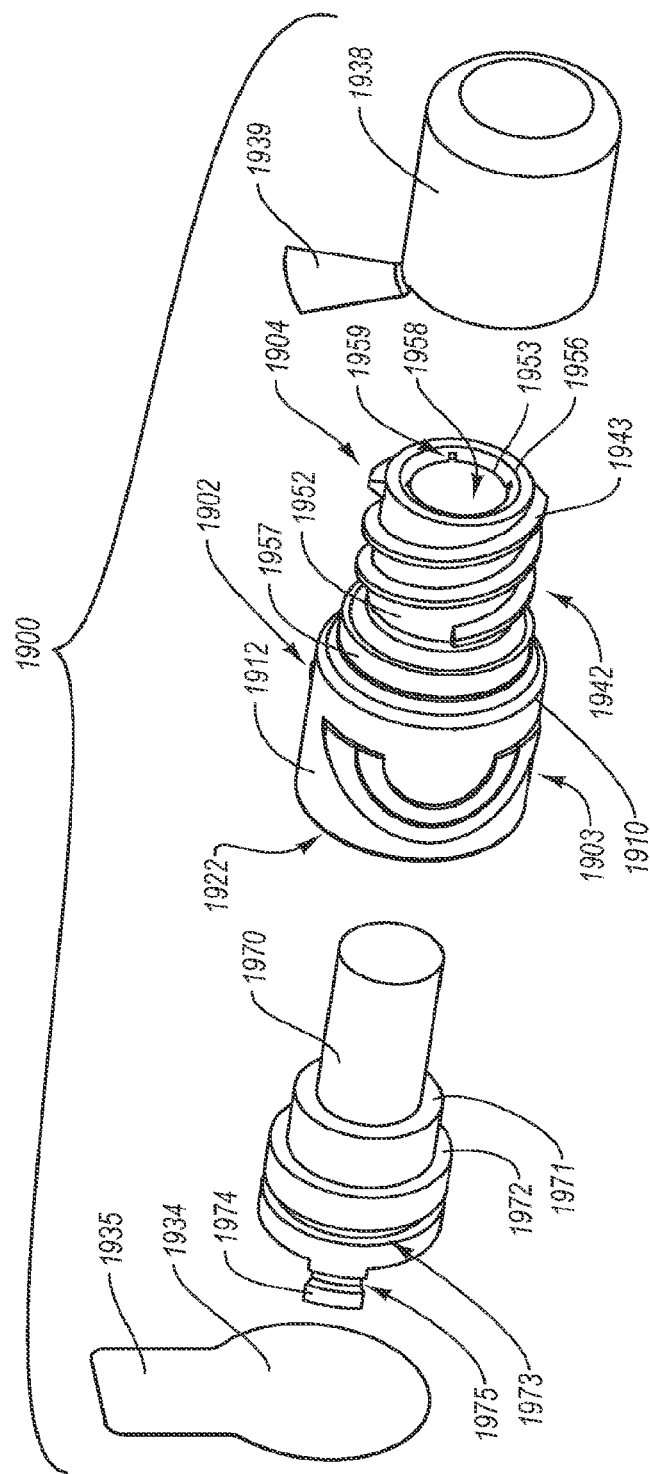
FIG. 26 is an exploded perspective view of the assembly of FIG. 25.

As shown in FIGS. 26, 28, and 29, the female cap 1902 can include a connection interface 1930 that is configured to couple with a connection interface of a medical connector, such as a needleless injection site. The connection interface 1930 can include threading 1931, which can be disposed at an interior of the sidewall 1912. In some embodiments, the male cap 1902 includes one or more gripping features 1903 at an exterior surface of the sidewall 1912. In the illustrated embodiment, the gripping features 1903 are raised areas. In other embodiments, the gripping features 1903 can include depressed areas. The gripping features 1903 can be formed in the shape of a company logo or any other suitable shape.

As shown in FIGS. 26, 27, and 29, the male cap 1904 can include a connection interface 1942 that is configured to couple with a connection interface of a medical connector, such as a medical attachment having a male luer. The connection interface 1942 can include threading 1943, which can be disposed at an exterior surface of the sidewall 1952. The cap 1904 can include one or more vents 1959, which can be located at an end of the sidewall 1952. The one or more vents can also extend along the length of sidewall 1952. In the illustrated embodiment, a constriction, rim, or lip 1953 projects radially inwardly at the end of the sidewall 1952, which can aid in maintaining the pad 1970 within the cap 1904. In particular, the lip 1953 can define a smaller inner diameter than an outer diameter of the pad 1970 (see FIG. 29). The vents 1959 can comprise notches in the lip 1953. The illustrated embodiment includes four vents 1959, although more or fewer vents are possible.

With reference to FIG. 26, the pad 1970 can define a shape generally resembling a series of tiered cylinders. A rim 1971 can extend transversely, or radially outwardly, from a cylinder that has the smallest diameter. Another rim 1972 can extend transversely from a cylinder having an intermediate diameter. The largest cylinder can have a recess 1973 disposed therein. In certain embodiments, such as the illustrated embodiment, one or more extensions 1974 protrude from an end of the pad 1970 in a longitudinal direction. Each extension 1974 can include a groove 1975 therein, as discussed further below. In other embodiments, the one or more extensions 1974 are omitted.

With reference to FIG. 29, the pad 1970 can be secured within the housing 1910 in any suitable manner, and thus can resist translational movement in either direction that would cause the pad 1970 to exit the housing 1910 from either open end of the housing. For example, in the illustrated embodiment, interaction of the threads 1931 with a left end of the pad 1970 can prevent the pad 1970 from moving out of the housing 1910 in a leftward direction as a portion of a medical connector (e.g., a male luer connector) is inserted into the housing 1910 from the right. As shown in FIG. 29, some portions of the pad 1970 can be compressed by the threads 1931, whereas the grooves 1975 of the extensions 1974 can accommodate the threads 1931. The enlarged tiered sections of the pad 1970, and the resultant interaction of the rims 1971, 1972 with the abutments 1920, 1921, respectively, can prevent the pad 1970 from moving out of the housing 1910 in the rightward direction as a portion of a medical connector (e.g., a needleless injection site) is advanced into the housing 1920 from the left. In other or further embodiments, the pad 1970 can be adhered to the housing 1910.

With reference to FIGS. 26 and 27, the cover 1938 can be secured to the housing 1910 in any suitable manner. For example, in some embodiments, an end of the cover 1938 is adhered or otherwise sealed to a sealing surface 1956 at an end of the sidewall 1952 so as to provide a hermetic seal. A side portion of the cover 1938 thus can cover the connection interface 1942 of the cap 1904. In other or further embodiments, a lower circumferential edge of the cover 1938 can be adhered or otherwise sealed to a sealing surface 1957 at a base end of the sidewall 1952 so as to provide a hermetic seal. With reference to FIGS. 26 and 28, the cover 1934 can be adhered or otherwise sealed to a sealing surface 1916 at an end of the sidewall 1912 of the housing 1910.

Figure 30:
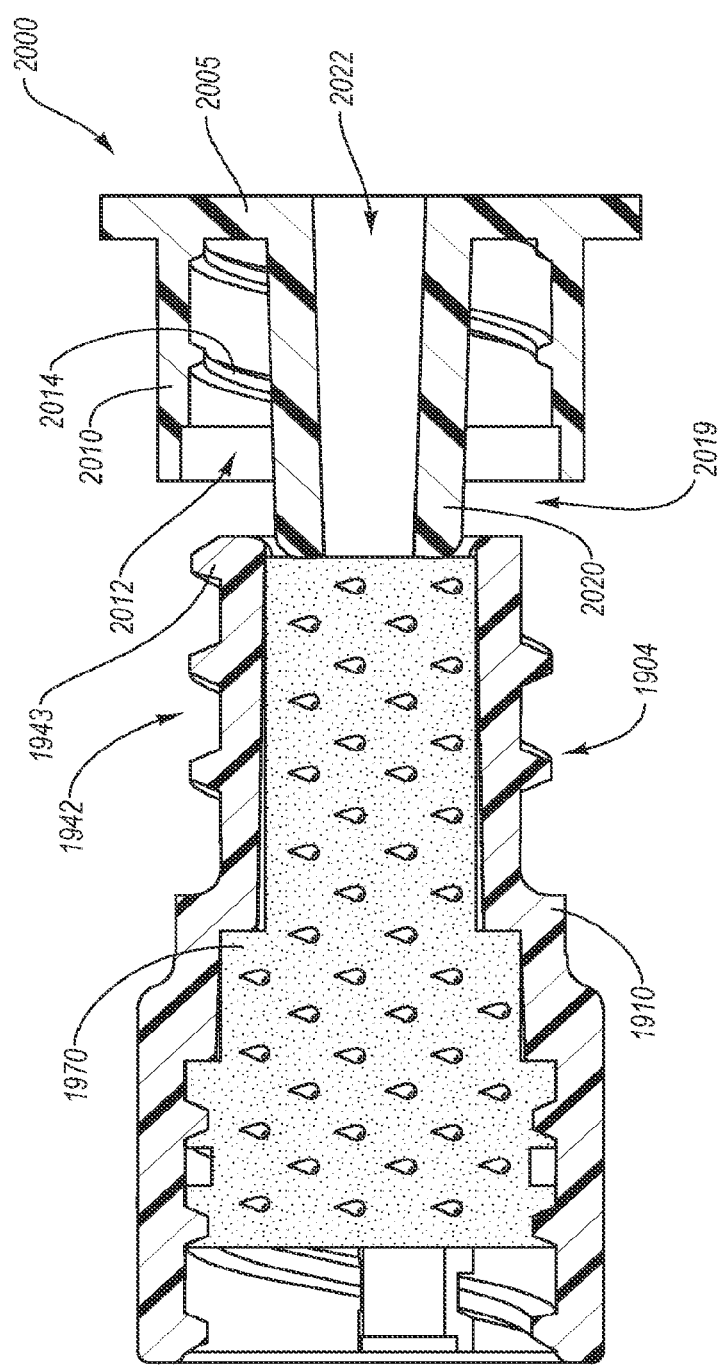
FIG. 30 is a cross-sectional view of the assembly of FIG. 25 showing an early stage of coupling a cap portion of the assembly with a medical connector that has a male protrusion.

FIG. 30 illustrates an early stage of the coupling of a medical connector 2000 with the cap 1904. The medical connector 2000 can be of any suitable variety, and may be referred to as a male medical connector. The medical connector 2000 can include a housing 2005 that complies with ISO standards (e.g., ISO 594-1:1986 and ISO 594-2:1998). The housing 2005 can include a skirt 2010 that defines a connection interface 2012, which itself can include threading 2014. The housing 2005 can also include an elongated portion, a male projection, or male protrusion 2019, which can define a fluid passageway 2022. In the illustrated embodiment, the male protrusion 2019 is a male luer 2020.

Although the illustrated embodiment of the medical connector 2000 comprises a male luer-lock connector, it is to be understood that other embodiments of the cap 1904 can be compatible with other varieties of medical connectors 2000. For example, in some embodiments, the connection interface 2012 may comprise latches, prongs, or some other suitable attachment mechanism instead of (or in addition to) the threading 2014. In other or further embodiments, the male protrusion 2019 may be something other than a male luer. For example, the male protrusion 2019 may be a substantially cylindrical extension, or may define some other suitable shape.

In the illustrated embodiment, a tip of the male luer 2020 can contact an end surface of the pad 1970 prior to engagement of the connection interfaces 1942, 2012 (e.g., the threadings 1943, 2014) with each other. Accordingly, some compression of the pad 1970 may occur without assistance from the connection interfaces 1942, 2012. In other embodiments, the connection interfaces 1942, 2012 may engage one another prior to contact being made between the tip of the male luer 2020 and the end surface of the pad 1970, such as may occur when the pad 1970 is more recessed within the housing 1910 and/or the skirt 2010 and its connection interface 2012 are longer. In either case, in some embodiments, the connection interfaces 1942, 2012 can assist in the compression of the pad 1970. The desired antiseptic concentration level of the pad 1970 is determined by the volume required to fully coat and disinfect the medical connector 2000, while taking into consideration the evaporative loss that may occur during the shelf life of cap 1904.

Figure 31:
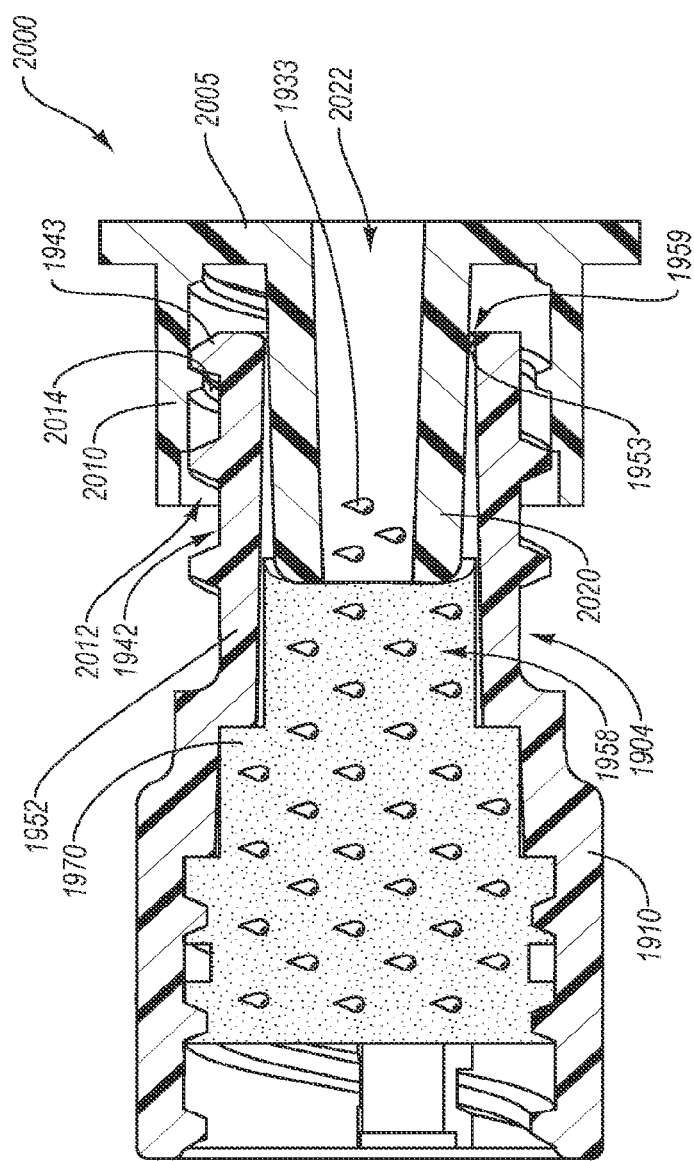
FIG. 31 is a cross-sectional view of the assembly of FIG. 25 showing a late stage of coupling the cap portion of the assembly with the medical connector that has a male protrusion.

FIG. 31 illustrates a later stage of the coupling of the medical connector 2000 with the cap 1904. As the male luer 2020 is advanced into the disinfection chamber 1958 of the cap 1904, it compresses the pad 1970 and causes antiseptic 1933 to egress therefrom. The pad 1970 can remain relatively fixed, rotationally, while the male luer 2020 is rotated and advanced further into the chamber 1958, which can effect a rubbing or scrubbing of the tip of the luer 2020, particularly as increased compression of the pad 1970 provides an increased force of the pad 1970 against the tip. The released antiseptic can fill an opening or volume of space between the sidewall 1952 of the housing 1910 and an outer surface of the male luer 2020, and can thereby disinfect the outer surface of the male luer 2020. Additionally, in the illustrated embodiment, the fluid passageway 2022 of the male luer 2020 is open such that antiseptic fluid 1933 may enter into it. In some instances, such as when the medical connector 2000 is connected to a fluid line 199 (see FIG. 5), it may be desirable to flush a portion of the fluid line after the cap 1904 has been disconnected from the medical connector 2000 so as to clear the male luer 2020 and any portion of the fluid line 199 into which antiseptic fluid 1933 has entered.

In certain embodiments, a seal can form between the lip 1953 and the male luer 2020 when the luer 2020 is advanced sufficiently far into the chamber 1958. The seal thus formed can be an interrupted seal, such that the seal is formed only at those regions where the luer 2020 and the lip 1953 are in contact with each other. Antiseptic 1933 can be permitted to exit from the chamber 1958 via the vents 1959. In some embodiments, the vents 1959 are sufficiently large to permit antiseptic 1933 to exit from the chamber 1958 freely once the antiseptic 1933 has been expelled from the pad 1970. Antiseptic 1933 that exits from the chamber 1958 through the vents 1959 can disinfect portions of the male luer 2020 that are proximal of the lip 1953.

In other embodiments, the vents 1959 are sufficiently small to prevent antiseptic 1953 from exiting from the chamber 1958 when a pressure within the chamber 1958 is the same or approximately the same as a pressure outside of the chamber 1958 (e.g., atmospheric pressure), and yet are sufficiently large to permit antiseptic 1933 to exit the chamber 1958 when the pressure within the chamber 1958 is significantly greater than the pressure outside of the chamber 1958, such as may result when the luer 2020 is being advanced deeper within the chamber 1958. The vents 1959 thus can permit selective egress of the antiseptic 1933 to aid in achieving the desired positioning of the male luer 2020, yet can maintain the antiseptic 1933 within the chamber 1958 in order to bathe a portion of the male luer 2020 once the male luer 2020 is positioned as desired. In still other embodiments, a fluid-tight seal is formed between the lip 1953 and the male luer 2020.

In certain embodiments, the pad 1970 may be recessed within the chamber 1958 to a greater degree when in the uncompressed state (e.g., when in the state shown in FIG. 30). Moreover, the threads 2014 of the connection interface 2012 and the threads 1943 of the connection interface 1942 can permit the antiseptic 1933 to pass through them, so as to provide additional venting of the chamber 1958. For example, threaded connection interfaces 2012, 1942 can permit antiseptic 1933 that has exited from the chamber 1958 to spiral about an outer surface of the second sidewall 1952 in a distal direction.

Figure 32:
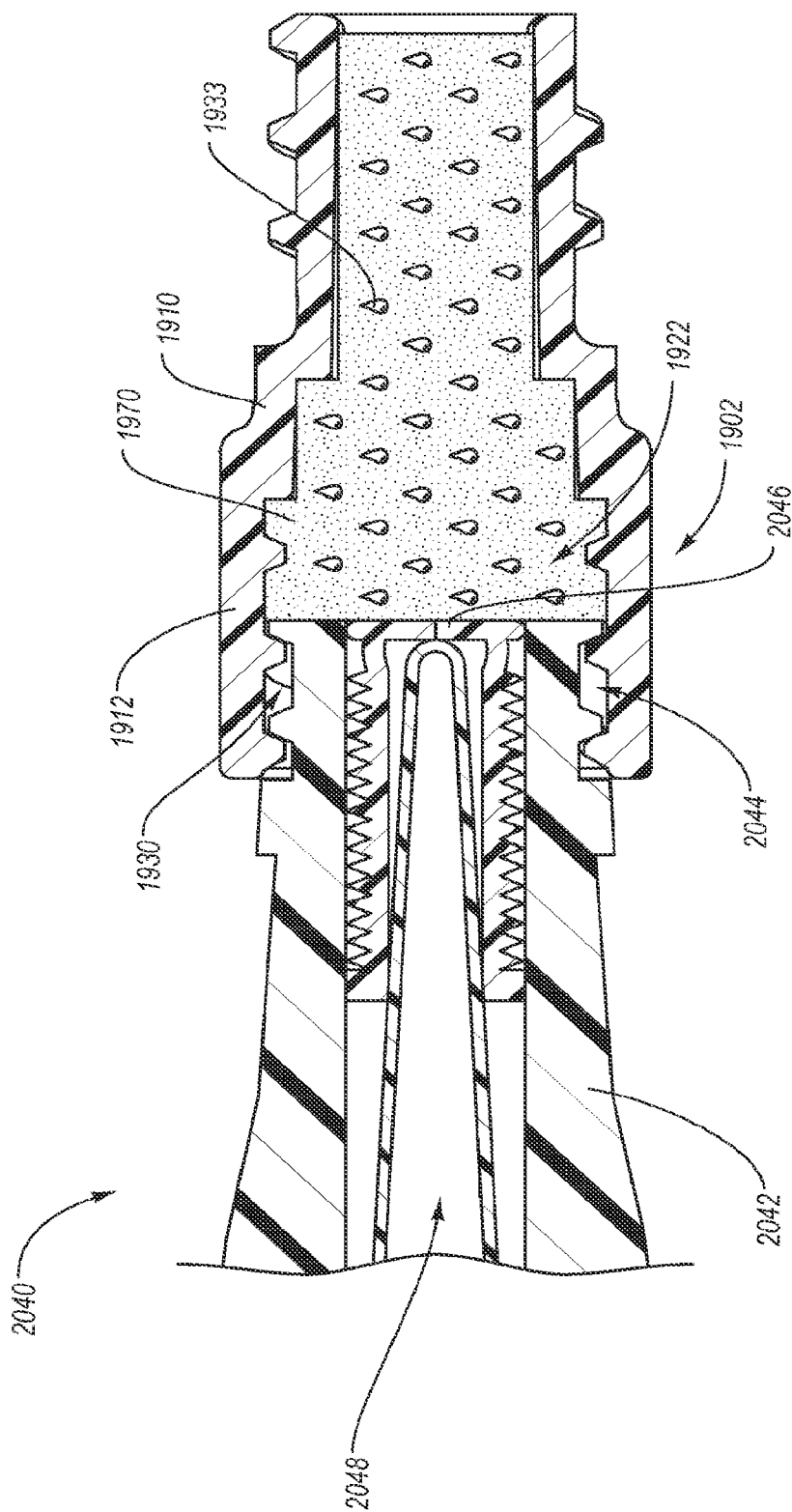
FIG. 32 is a cross-sectional view of the assembly of FIG. 25 showing a late stage of coupling the other cap portion of the assembly with a first embodiment of a needleless injection site.
Figure 33:
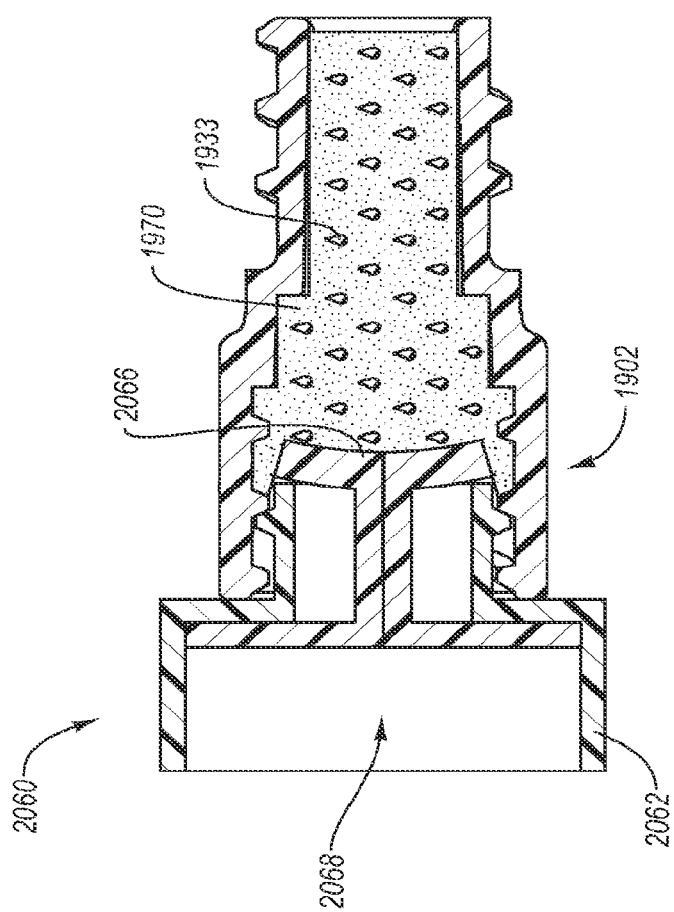
FIG. 33 is a cross-sectional view of the assembly of FIG. 25 showing a late stage of coupling the other cap portion of the assembly with a second embodiment of a needleless injection site.
Figure 34:
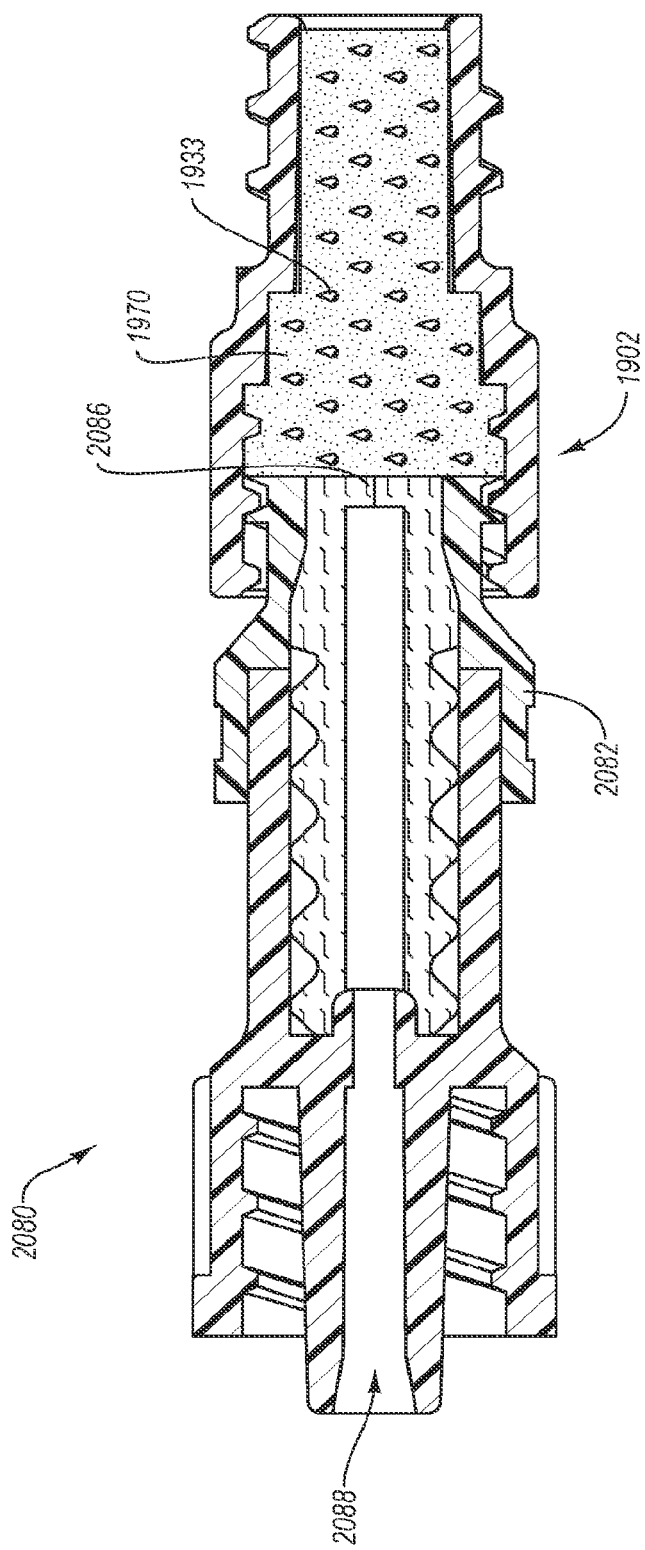
FIG. 34 is a cross-sectional view of the assembly of FIG. 25 showing a late stage of coupling the other cap portion of the assembly with a third embodiment of a needleless injection site.

Each of FIGS. 32-34 illustrates the cap 1902 coupled with a separate needleless injection site 2040, 2060, 2080. As with other caps disclosed herein, the cap 1902 can be versatile so as to couple with a variety of different types of medical connectors in a secure fashion that disinfects each type of medical connector. As can be seen in each of FIGS. 32-34, coupling of the needleless injection sites 2040, 2060, 2080 with the cap 1902 can effect compression of one end of the pad 1970 in a manner similar to that described above with respect to compression of the other end of the pad 1970. Compression of the pad 1970 and rotation of the needleless injection site 2040, 2060, 2080 can effect rubbing, swabbing, or scrubbing of the needleless injection site and disinfection thereof via the antiseptic 1933.

With reference to FIG. 32, the needleless injection site 2040 can comprise a Clave.® port available from ICU Medical, Inc. The needleless injection site 2040 can include a housing 2042 that defines a connection interface 2044. The needleless injection site 2040 can further include an elastomeric seal 2046, which is shown in a closed configuration in which fluid access is not permitted into a fluid passageway 2048. Small crevices can exist between the housing 2042 and the elastomeric seal 2046 at an end of the needleless injection site 2040 that is inserted into disinfection chamber 1922. As the connection interface 2044 cooperates with the connection interface 1930 defined by the sidewall 1912 to draw the tip of the needleless injection site 2040 into the disinfection chamber 1922, the pad 1970 can be compressed so as to generally conform to the crevices. Compression of the pad 1970 likewise can expel antiseptic 1933, which, in some instances, can fill in portions of the crevices that the pad 1970 may not be able to contact directly. As the pad 1970 is compressed, the seal 2046 can remain closed so as to prevent antiseptic 1933 from entering the fluid passageway 2048. With reference again to FIG. 29, if present, the one or more extensions 1974, due to their positioning over the threads 1031, additionally can rub or scrub the side surfaces of the needleless injection site 2040. Thus, a thorough rubbing and disinfection of the needleless injection site 2040 can be accomplished via the cap 1902, and the performance of the cap 1902 in this regard can exceed that achieved via standard swabbing protocols and can be less susceptible to human error.

With reference to FIG. 33, the needleless injection site 2060 can comprise a Q-Syte® port available from Becton, Dickinson and Company. The needleless injection site 2060 can include a housing 2062 and an elastomeric seal 2066, which is shown in a closed configuration in which fluid access is not permitted into a fluid passageway 2068. As with the needleless injection site 2040, small crevices can exist between the housing 2062 and the elastomeric seal 2066. However, the crevices can exist at a side portion of the needleless injection site 2060, rather than at its tip. Nevertheless, as the needleless injection site 2060 is advanced into the cap 1902, the pad 1970 can be compressed so as to generally conform to these differently shaped crevices. Compression of the pad 1970 likewise can expel antiseptic 1933, which, in some instances, can fill in portions of the crevices that the pad 1970 may not be able to contact directly. The seal 2066 can be maintained in the closed position during the coupling procedure, so as to prevent any of the antiseptic 1933 from entering the fluid passageway 2068.

With reference to FIG. 34, the needleless injection site 2080 can comprise a SmartSite.® port available from Cardinal Health, Inc. The needleless injection site 2080 can include a housing 2082 and an elastomeric seal 2086, which is shown in a closed configuration in which fluid access is not permitted into a fluid passageway 2088. As with the needleless injection sites 2040, 2060, small crevices can exist between the housing 2082 and the elastomeric seal 2086. However, these crevices can be in yet different positions than those of the needleless injection sites 2040, 2060. Nevertheless, as the needleless injection site 2080 is advanced into the cap 1902, the pad 1970 can be compressed so as to generally conform to these differently shaped crevices. Compression of the pad 1970 likewise can expel antiseptic 1933, which, in some instances, can fill in portions of the crevices that the pad 1970 may not be able to contact directly. The seal 2086 can be maintained in the closed position during the coupling procedure so as to prevent any of the antiseptic 1933 from entering the fluid passageway 2088. Additionally, each of the needleless injection sites 2040, 2060, 2080 may advance into the cap 1902 by different amounts. The cap 1902 thus can be adaptable and versatile. Additional, non-limiting examples of needleless injection sites with which the cap 1902 can selectively couple include the Clearlink.® Site available from Baxter and the InVision-Plus.® available from Rymed.

Features, usage, and operation of the assembly 1900 can resemble that of one or more of the assemblies described above. For example, in the illustrated embodiment, the pad 1970 is in an uncompressed or expanded state when the disinfection chambers 1922, 1958 in which it is housed are in a pre-use, sealed condition. Additionally, the caps 1902, 1904 are coaxial with each other with open ends that face in opposite directions. Likewise, the caps 1902, 1904 are connected to each other when the assembly 1900 is in a pre-use state.

However, certain differences can exist. For example, in the illustrated embodiment, the caps 1902, 1904 cannot be removed from each other. Moreover, the assembly 1900 includes a single pad 1970 that is used in both caps 1902, 1904. Although not shown in the drawings, it is understood that each cap 1902, 1904 can be coupled with a separate medical connector such that the pad 1970 is compressed from both ends when the caps 1902, 1904 are in a coupled state.

Figure 35:
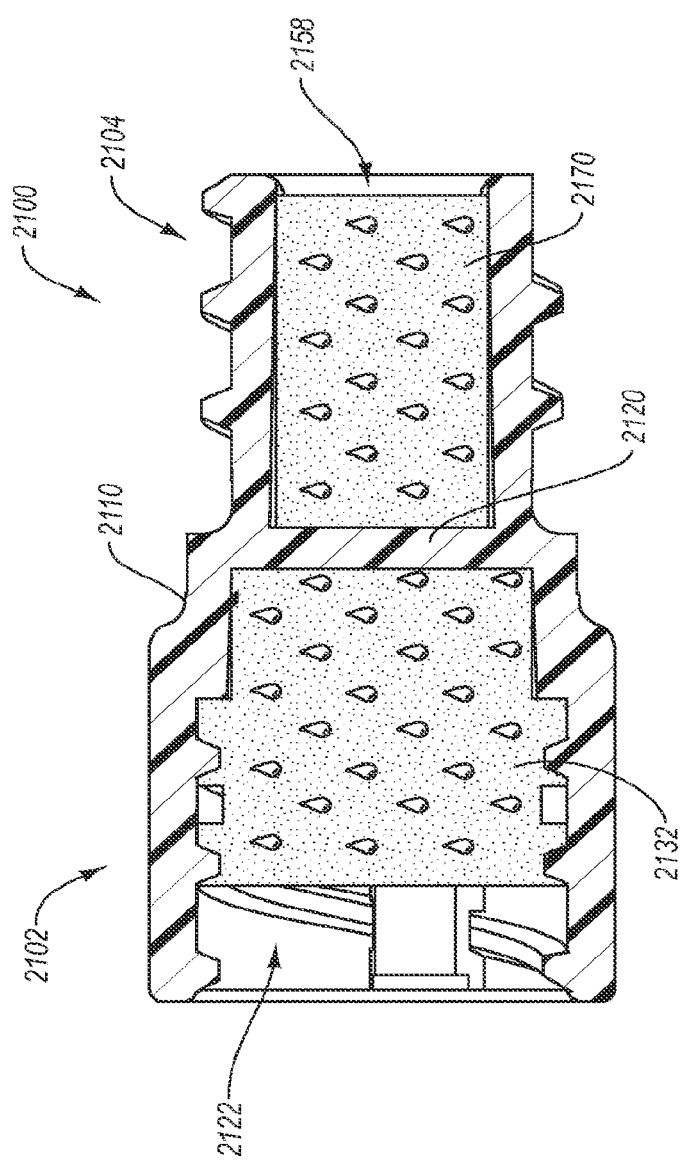
FIG. 35 is a cross-sectional view of another embodiment of an assembly that includes two cap portions integrally connected to each other, with covers removed from the assembly.

FIG. 35 illustrates another embodiment of an assembly 2100, which can resemble one or more of the assemblies described above, particularly the assembly 1900, in certain respects. Accordingly, like features are designated with like reference numerals, with the leading digits incremented to "21." The assembly 2100 can include caps 2102, 2104, such as the caps 1902, 1904, that are fixedly, permanently, or integrally connected with each other. Covers such as the covers 1934, 1938, which are not shown in FIG. 35, can be used with the caps 2102, 2104. The assembly 2100 can include a single housing 2110 that defines two disinfection chambers 2122, 2158. The housing 2110 can include a partition 2120 that separates the disinfection chambers 2122, 2158 from each other such that the chambers 2122, 2158 are fluidly separated from one another. Each chamber 2122, 2158 can include a separate pad 2132, 2170 therein.

Figure 36:
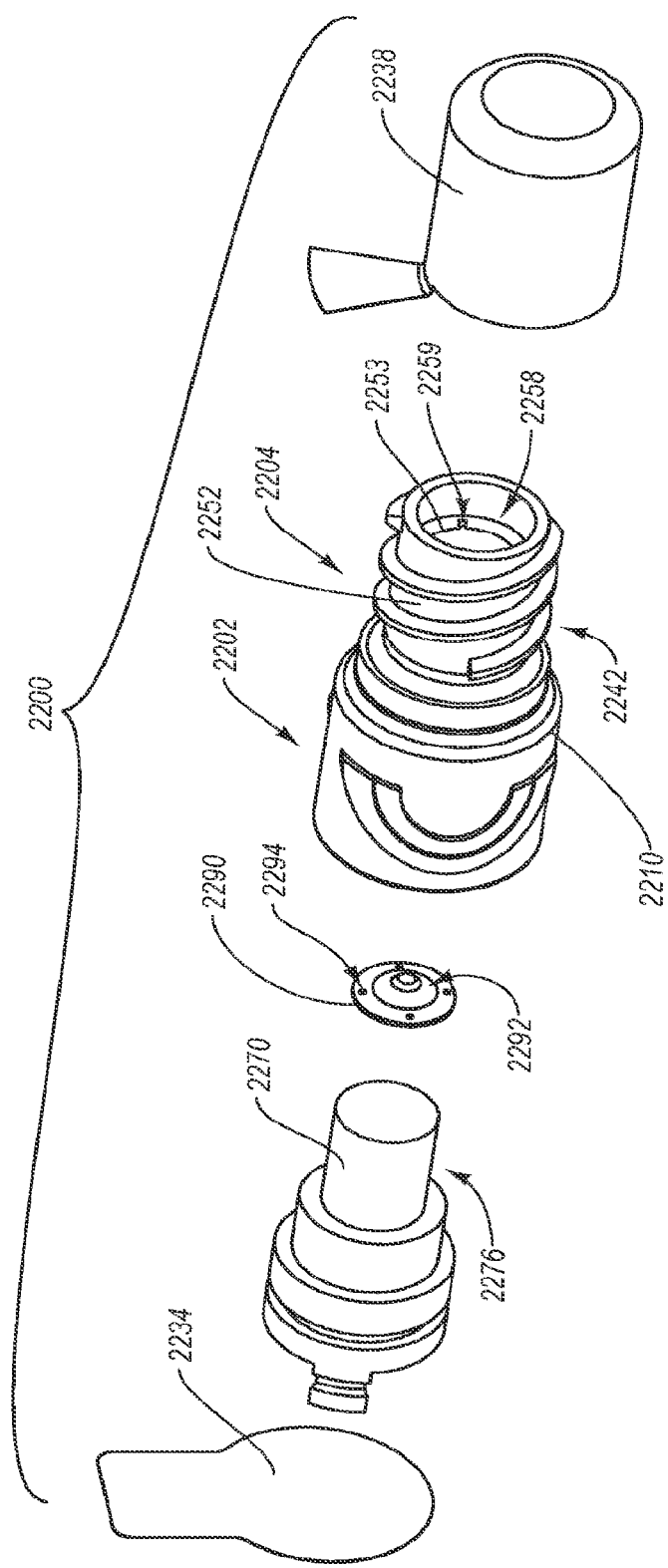
FIG. 36 is an exploded perspective view of another embodiment of an assembly that includes two cap portions integrally connected to each other.
Figure 37:
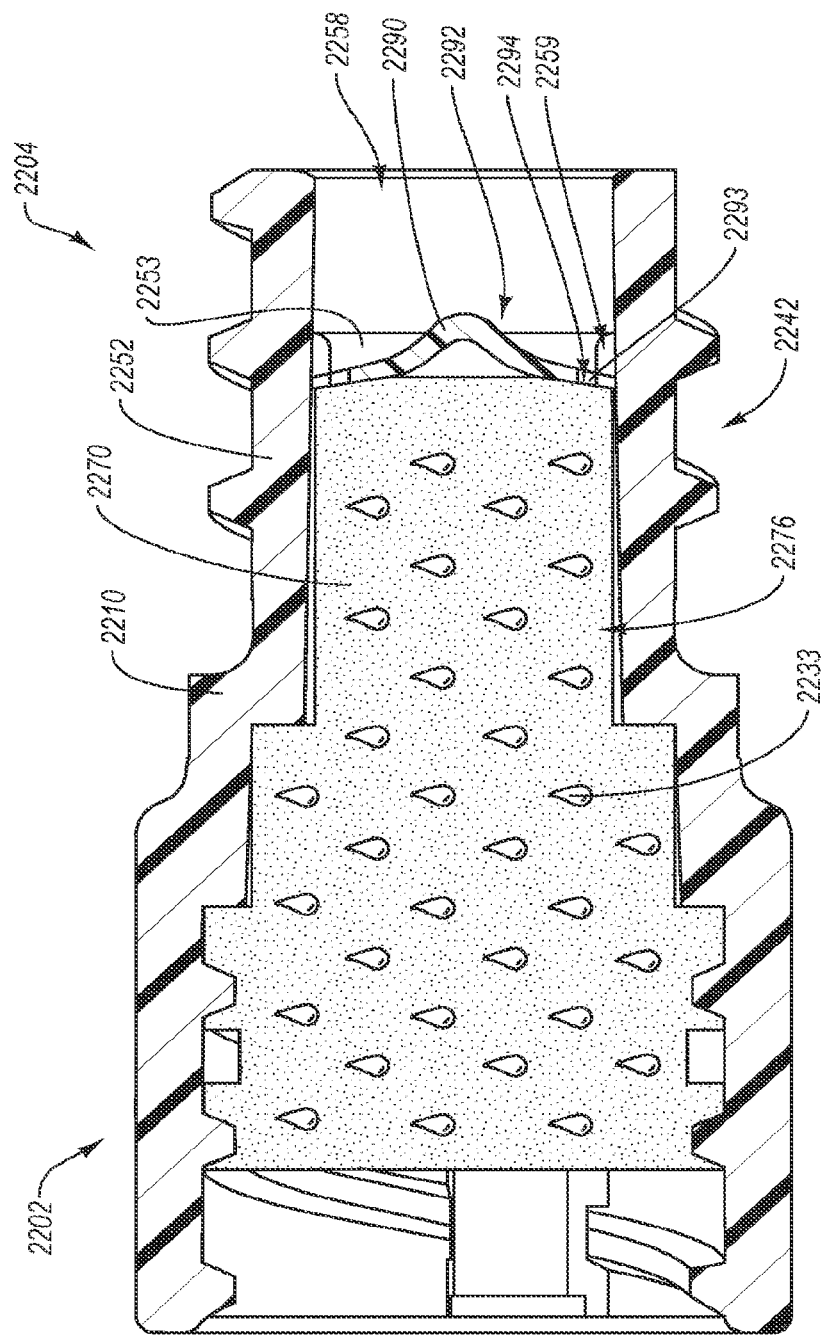
FIG. 37 is a cross-sectional view of the assembly of FIG. 36 similar to the view shown in FIG. 29.

FIGS. 36 and 37 illustrate another embodiment of an assembly 2200, which can resemble one or more of the assemblies described above, particularly the assemblies 1900 and 2100, in certain respects. Accordingly, like features are designated with like reference numerals, with the leading digits incremented to "22." The assembly 2200 can include a female cap 2202 and a male cap 2204 that are fixedly, permanently, or integrally connected with each other. The assembly can include a housing 2210, which can include a sidewall 2252 that defines a disinfection chamber 2258 and a connection interface 2242. Covers 2234, 2238, such as the covers 1934, 1938, can be used with the caps 2202, 2204.

The female cap 2202 can be substantially the same as the female cap 1902. However, the male cap 2204 can differ from the male cap 1904 in certain respects. For example, the cap 2204 can include a sealing member 2290. In the illustrated embodiment, the sealing member 2290 is shaped substantially as a conical disk. The sealing member 2290 can include a seal region 2292 which, in the illustrated embodiment, is rounded and projects toward an open end of the disinfection chamber 2258 when situated therein. In other embodiments, the sealing member 2290 can define other shapes, such as, for example, square, oval, diamond, or other non-circular shapes. Further, the sealing member 2290 and the seal region 2292 may be a separate components that are integrally connected. The sealing member 2290 can include one or more ports 2294, which can define openings or channels 2293 that extend between opposing sides or faces of the sealing member 2290. Other configurations of the ports 2294 are also contemplated, such as, for example, self-sealing slits. In other configurations, such as some instances in which the sealing member 2290 is a non-circular shape, the ports can be eliminated since the antiseptic can flow around the sides of the sealing member 2290. In some embodiments, the sealing member 2290 can be relatively rigid so as to maintain a pre-formed shape, but may be configured to readily form a fluid-tight seal with a male luer of a medical connector. The sealing member 2290 can be formed of any suitable material, such as an elastomer or any thermoplastic such as polypropylene, polycarbinate, acrylonitrile butadiene styrene (ABS), polyvinyl chloride (PVC), or rigid or semi-rigid thermoset plastic. The sealing member 2290 can be formed in any suitable fashion, such as via molding or die cutting.

The sealing member 2290 can be coupled with a biasing element 2276, which can be configured to resist or oppose movement of the sealing member 2290. Stated otherwise, the biasing element 2276 can provide a bias to the sealing member 2290 in a direction of an initial position of the sealing member 2290, such as that shown in FIG. 37, once the sealing member 2290 has been displaced from that initial position. Accordingly, in the embodiment depicted in FIG. 37, the biasing element 2276 biases the sealing member 2290 in a proximal direction when the sealing member 2290 is displaced distally. The terms "proximal" and "distal," when used herein relative to a cap, are such that a medical device is inserted into a proximal end of the cap and advanced toward a distal end of the cap. Accordingly, in the illustrated embodiment, the proximal ends of the caps 2202, 2204 are at opposite ends of the assembly 2200 and the distal ends of the caps 2202, 2204 are fixedly joined with each other.

The male cap 2204 can include a rim 2253, similar to the lip 1953, which can include one or more vents 2259. However, in the illustrated embodiment, the rim 2253 is more recessed from a proximal end of the cap 2204 (e.g., deeper within the cavity 2258). A portion of a pad 2270 that is positioned within the disinfection chamber 2258 can be shorter than a corresponding portion of the pad 1970, so as to more readily fit below the more recessed rim 2253. As shown in FIG. 37, the pad 2270 can be seated beneath the sealing member 2290, and the sealing member 2290 can be seated beneath the rim 2253 when the male cap is in the pre-use configuration. In some embodiments, the pad 2270 is in an uncompressed state (e.g., a longitudinally uncompressed state) when situated as shown in FIG. 37. The pad 2270 can include an antiseptic 2233 therein.

In the illustrated embodiment, the pad 2270 is resiliently compressible such that the biasing element 2276 comprises the pad 2270. Stated otherwise, compression of the pad 2270 gives rise to a biasing force that tends to restore the pad 2270 to its uncompressed state. The biasing force may increase with greater compression of the pad 2270. In some embodiments, the pad 2270 is fixedly secured to the sealing member 2290, such as by an adhesive or any suitable lamination technique. In other embodiments, the sealing member 2290 is not secured to the pad 2270, but movement of the sealing member 2290 within the disinfection chamber 2258 can nevertheless be constrained by a proximal end of the pad 2270 and a distal edge of the rim 2253.

The sealing member 2290 can aid in maintaining the antiseptic 2233 within the pad 2270 when the cap 2204 is in a pre-use condition. For example, in some embodiments, only a small surface area of the proximal end of the pad 2270 that is directly beneath the ports 2294 of the sealing member 2290 is directly exposed to air when the proximal end of the cap 2204 is uncovered. Accordingly, evaporative loss of the antiseptic 2233 can be slowed. Moreover, in other or further embodiments, the ports 2294 may be defined by channels that are sufficiently small to prevent liquid antiseptic 2233 from passing through them when the pressure on both sides of the sealing member 2290 is balanced. However, the ports 2294 may permit liquid antiseptic 2233 to pass through them when the pressure on one side of the sealing member 2290 is greater than the pressure on the other side of the sealing member 2290, as discussed further below. The pad 2270 itself can also be configured to retain the antiseptic 2233 until it is compressed.

In some embodiments, an outer edge of the sealing member 2290 can form a fluid-tight seal with an inner surface of the sidewall 2252 when the cap 2204 is in the pre-use state. In further embodiments, the seal can be maintained as the sealing member 2290 is moved distally within the disinfection chamber 2258 such that liquid antiseptic 2233 is only permitted to bypass the sealing member 2290 through the ports 2294. In other embodiments, an outer edge of the sealing member 2290 may not form a fluid-tight seal with the sidewall 2252, whether initially or after having been moved from the pre-use condition, such that antiseptic 2233 can bypass the sealing member 2290 around its outer edge.

Figure 38:
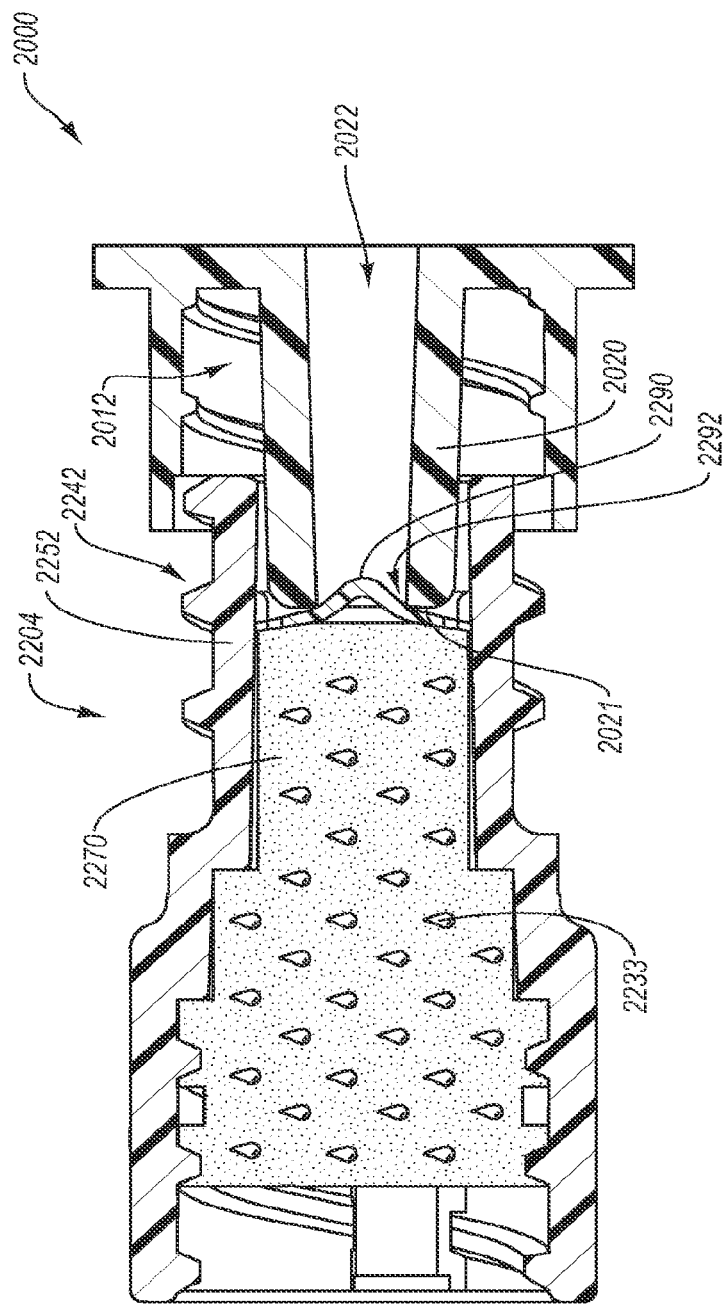
FIG. 38 is a cross-sectional view of the assembly of FIG. 36 showing an early stage of coupling a cap portion of the assembly with a medical connector that has a male protrusion.

FIG. 38 illustrates an early stage of coupling a medical connector 2000 with the cap 2204. A tip 2021 of a male luer 2020 contacts the seal region 2292 of the sealing member 2290. In the illustrated embodiment, a portion of the sealing member 2290 extends into a lumen 2022 of the connector 2000 such that the contact is primarily between an inner edge of the tip 2021 and a thin band of the sealing member 2290. Such an arrangement can assist in forming a fluid-tight seal due to a relatively higher pressure that results between the tip 2021 and the sealing member 2290 when forces (e.g., an insertion force on the tip 2021 and an oppositely directed biasing force on the sealing member 2290) are distributed over relatively smaller areas. Such an arrangement likewise can allow antiseptic to contact much or all of an external surface of the luer 2020, including a distal surface of the tip 2021.

In the illustrated embodiment, contact between the tip 2021 and the sealing member 2290 occurs just prior to engagement of a connection 2012 of the connector 2000 with the connection interface 2242. In other embodiments, the connection interfaces 2012, 2242 can engage each other prior to contact between the tip 2021 and the sealing member 2290. In either case, as the connection interfaces 2012, 2242 cooperate with each other to connect the cap 2204 to the medical connector 2000 (e.g., as the cap 2204 is threaded onto the connector 2000), a fluid-tight seal is formed or maintained between the seal region 2292 of the sealing member 2290 and the tip 2021 of the male luer 2020.

Figure 39:
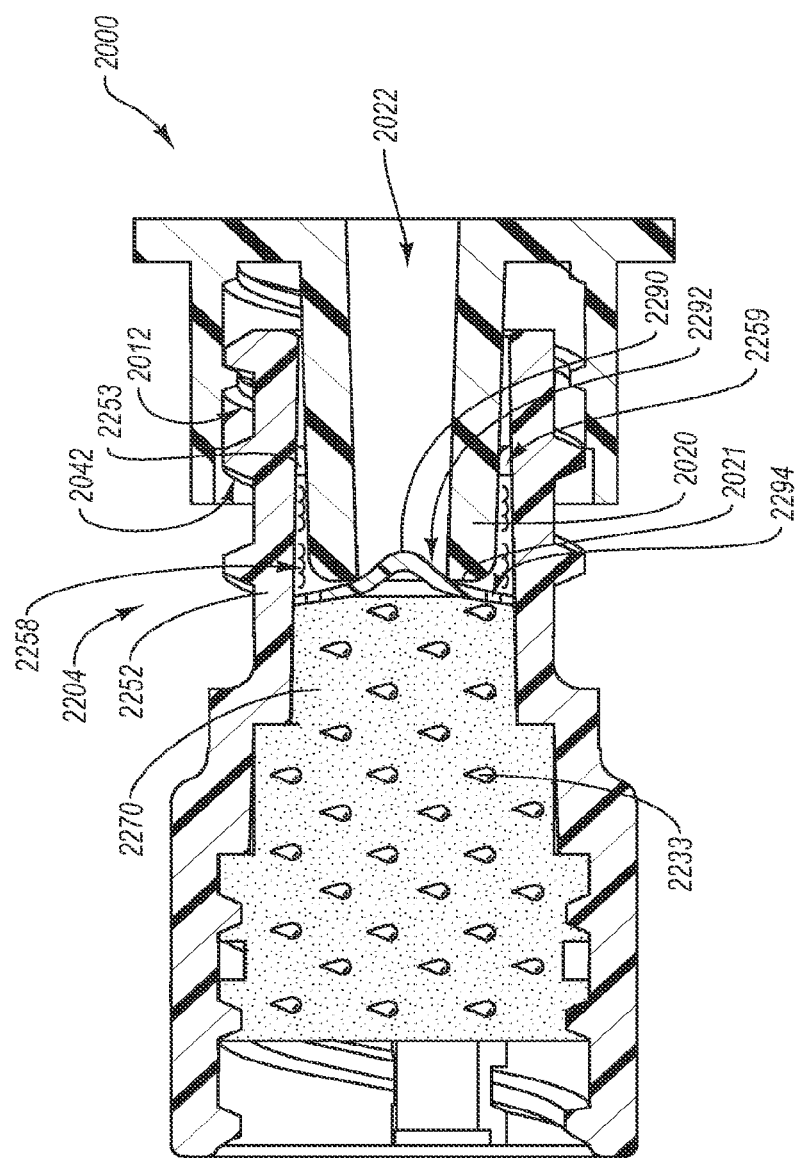
FIG. 39 is a cross-sectional view of the assembly of FIG. 36 showing a late stage of coupling a cap portion of the assembly with a medical connector that has a male protrusion.
Figure 40:
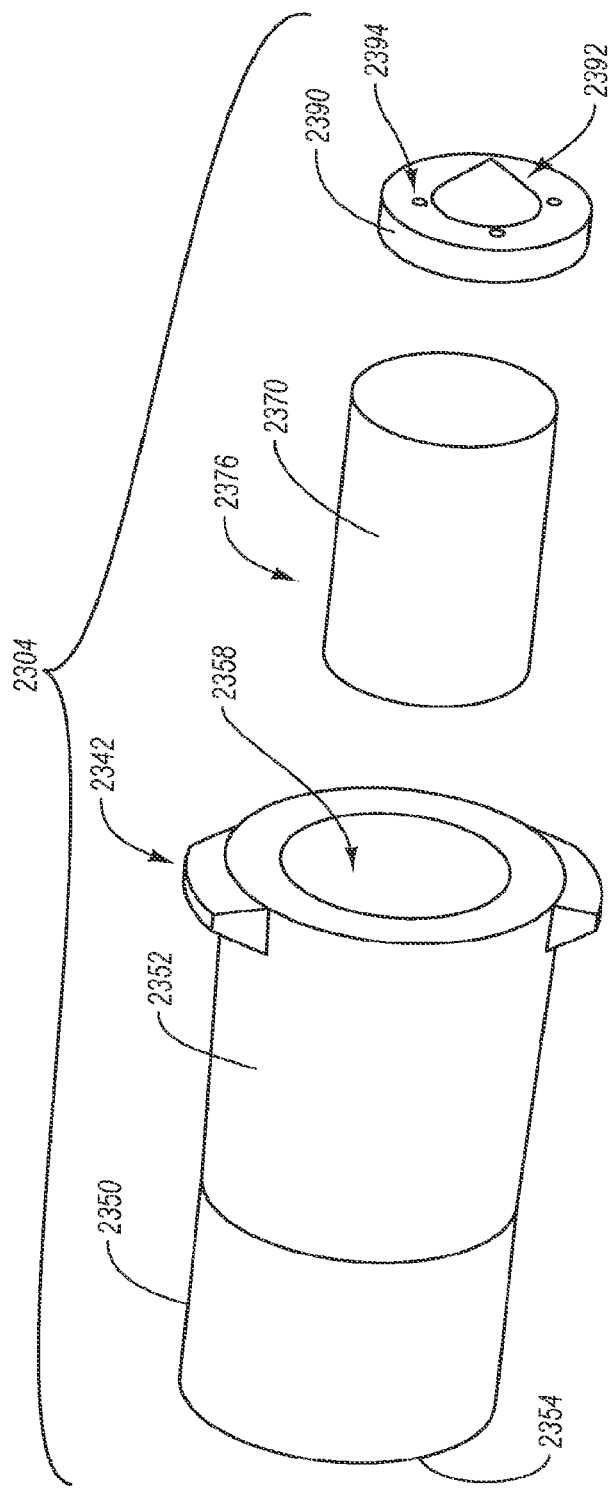
FIG. 40 is an exploded perspective view of another embodiment of a cap configured for coupling with a medical connector having a male protrusion.

FIG. 39 illustrates a late or final stage of coupling the medical connector 2000 with the cap 2204. To arrive at this stage, the cap 2204 is advanced over the male luer 2020 to a greater extent. As a result, the luer 2020 is advanced further into the disinfection chamber 2258, thereby moving the sealing member 2290 distally and compressing the pad 2270. Compression of the pad 2270 forces antiseptic 2233 out of the pad 2270. Moreover, as the pad 2270 is compressed, the volume of the portion of the disinfection chamber 2258 that is on the distal side of the sealing member 2290 is reduced, thereby increasing the pressure in that portion of the disinfection chamber 2258. As a result, the antiseptic 2233 is forced through the ports 2294 into the portion of the disinfection chamber 2258 on the proximal side of the sealing member 2290. Due to the seal between the sealing member 2290 and the luer 2020, the antiseptic 2233 is prevented from entering the lumen 2022 of the luer 2020, and thus is prevented from contacting or mixing with medical fluid that may be within the lumen 2022 when the cap 2204 is coupled with the medical connector 2000 and/or that may flow through the lumen 2022 after the cap 2204 has been removed from the connector 2000. The antiseptic 2233 can fill the open region of the disinfection chamber 2258 on the proximal side of the sealing member 2290.

As the luer 2020 is advanced distally in the disinfection chamber 2258, another seal, or partial seal, can be formed between an outer surface of the luer 2020 and an inner surface of the rim 2253. Where present, the seal can be substantially fluid-tight. However, the vents 2259 can interrupt the seal so as to permit antiseptic 2233 to exit from the chamber 2258. In further embodiments, a proximal or distal surface of the rim 2253 can be covered with a covering, such as, for example, Tyvek.® or other nonwoven material, which can filter microbes from the air entering the disinfection chamber 2258 via the vents 2259, yet can permit antiseptic 2233 to pass through it so as to exit from the disinfection chamber 2258. In other embodiments, the rim 2253 is uninterrupted (e.g., is free of vents 2259) such that an uninterrupted seal can be formed between the rim 2253 and the male luer 2020.

With continued reference to FIG. 39, when the cap 2204 is connected to the medical device 2000, antiseptic 2233 can fill the disinfection chamber 2258 between the seals formed by contact between the luer 2020 and the sealing member 2290 and between the luer 2020 and the rim 2253. An outer surface of the luer 2020 between these two sealed regions of the luer 2020 thus can be bathed in the antiseptic 2233 and disinfected thereby. As mentioned with respect to the assembly 1900, the rim 2253 can be positioned at a deeper or a more shallow position relative to the housing 2252, which can result in disinfection of a smaller or greater surface area of the luer 2020, respectively. In certain embodiments in which the proximal seal between the rim 2253 and the male luer 2020 is interrupted (e.g., where the rim 2253 includes vents 2259), antiseptic 2233 can be permitted to exit from the chamber 2258. In some embodiments, the vents 2259 are sufficiently large to permit antiseptic 2233 to exit from the chamber 2258 freely once the antiseptic 2233 has been expelled from the pad 2270. Antiseptic 2233 that exits from the chamber 2258 through the vents 2259 can disinfect portions of the male luer 2020 that are proximal of the rim 2253.

When the cap 2204 is removed from the medical device 2000, it can naturally or automatically return to the orientation shown in FIG. 37. In particular, the resiliently compressible pad 2270 can move the sealing member 2290 distally to its pre-use position. In so doing, the expanding portion of the disinfection chamber 2258 that is distal of the sealing member 2290 can have a decreased pressure such that antiseptic 2233 is forced back through the ports 2294 of the sealing member 2290 in a distal direction. The expanding pad 2270 can soak up or absorb the returned antiseptic 2233. The expanding pad 2270 can provide sufficient force to the sealing member 2290 to maintain the seal with the seal region 2292 such that antiseptic 2233 is prevented from entering into the lumen 2022 as the cap 2204 is decoupled from the medical device 2000.

In other embodiments, the caps 2202, 2204 can more closely resemble the caps 2102, 2104 described above. For example, the cap 2202 can have a separate pad, which is spaced from or separated from the pad 2270 by a partition. In still other embodiments, the caps 2202, 2204 can be readily disconnected from each other, and in further embodiments, may be configured for selective reconnection with each other in manners such as those described with respect to other caps herein.

FIGS. 40-45 illustrate another embodiment of a cap 2304, which can resemble one or more of the caps described above in certain respects. For example, the cap 2304 can replace or readily be altered to replace any of the caps 1004, 1104, 1204, 1304, 1404, 1504, 1604, 1804, 1904, 2104, 2204 in the systems 1000, 1100, 1200, 1300, 1400, 1500, 1600, 1800, 1900, 2100, 2200 described above. Accordingly, like features are designated with like reference numerals, with the leading digits incremented to "23."

The cap 2304 can include a housing 2350 having a sidewall 2352 and a base wall 2354 that define a disinfection chamber 2358. The housing 2350 can further include a coupling interface 2342. The cap 2304 can include a biasing member 2376, which can comprise a resiliently compressible pad 2370, which can in turn include an antiseptic 2333 therein. The cap 2304 can further include a sealing member 2390, which includes a sealing region 2392 and one or more ports 2394, which include channels 2393 that extend through the sealing member 2390.

The sidewall 2352 of the housing 2350 can be different from that of the illustrated embodiment of the cap 2204. In particular, at least a portion of an inner surface of the sidewall 2352 (e.g., a proximal region thereof) can be tapered so as to form a fluid-tight seal with a male luer. For example, at least a portion of the inner surface of the sidewall 2352 can comply with ISO standards (e.g., ISO 594-1:1986 and ISO 594-2: 1998) for forming a seal with a male luer. In the illustrated embodiment, the sidewall 2352 is devoid of any inwardly projecting rims that could interrupt complementarities between the sidewall 2352 and a male luer.

Figure 41:
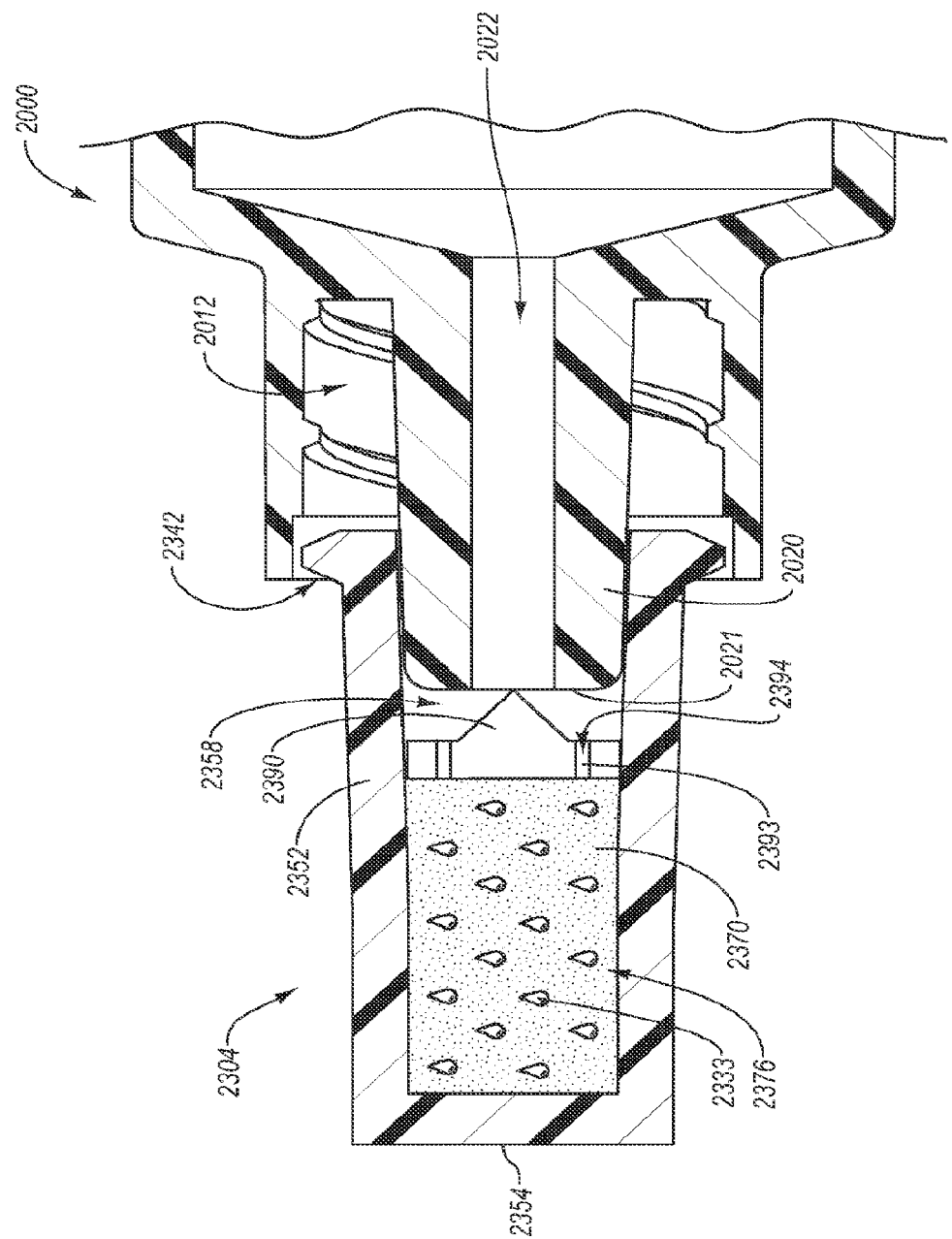
FIG. 41 is a cross-sectional view of the assembled cap of FIG. 40 showing an early stage of coupling the cap with a medical connector that has a male protrusion in which the male protrusion has not yet contacted a sealing member of the cap.

FIGS. 41-45 illustrate consecutive stages of the cap 2304 being coupled with a medical device 2000. As shown in FIG. 41, a tip 2021 of a male luer 2020 can be received within the disinfection chamber 2358 prior to contacting the sealing member 2390. Stated otherwise, the sealing member 2390 can be recessed relative to a proximal end of the sidewall 2352 by a distance that is sufficiently great to permit at least a portion of the male luer 2020 to be received within the sidewall 2352 before the male luer contacts the sealing member 2390.

Figure 42:
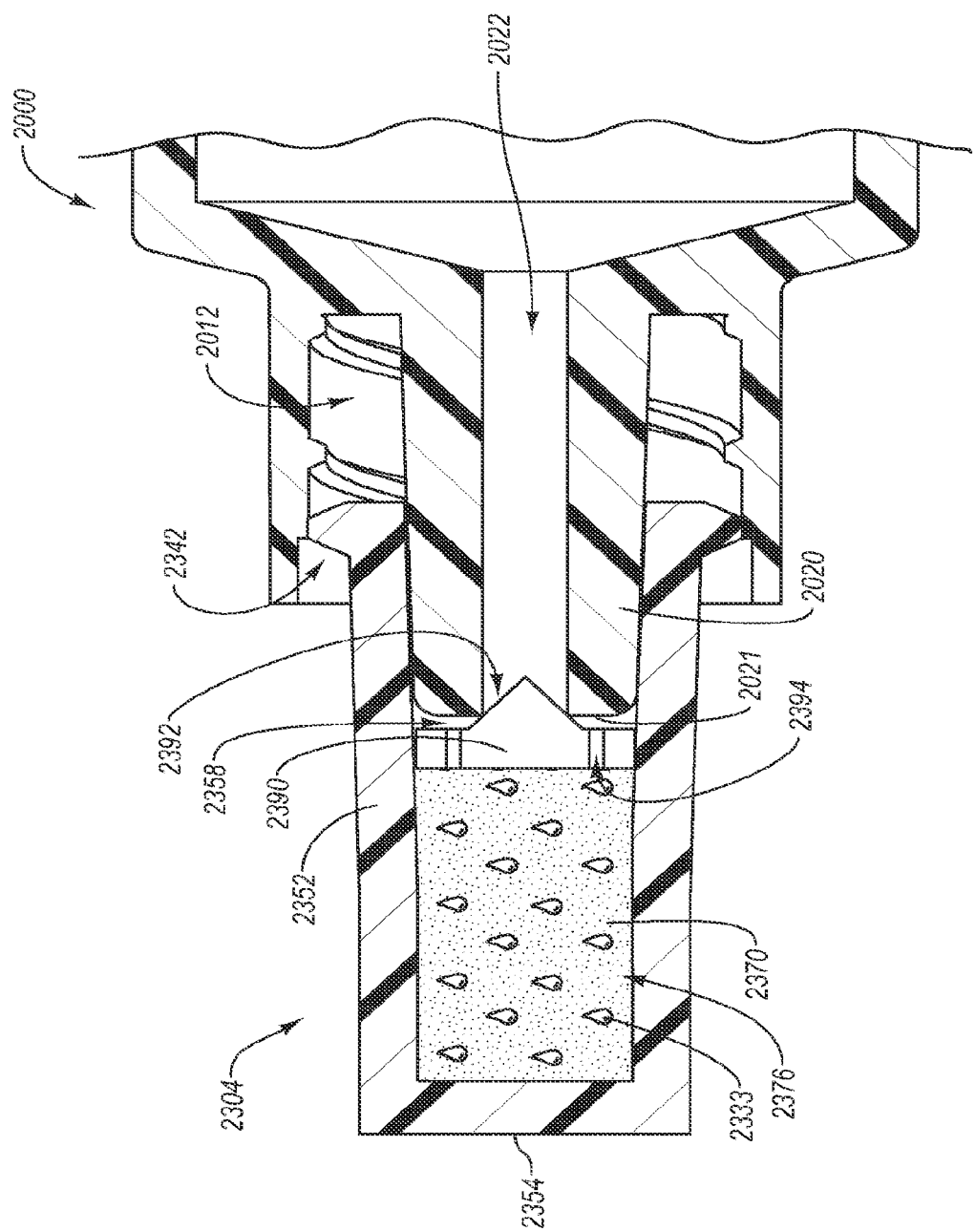
FIG. 42 is a cross-sectional view such as that of FIG. 41 showing a later stage of coupling the cap with the medical connector in which the male protrusion forms a fluid-tight seal with the sealing member of the cap.

In FIG. 42, the luer 2020 has been advanced further within the disinfection chamber 2358 so as to contact the seal region 2392 of the sealing member 2390. In the illustrated embodiment, the connection interface 2342 of the cap 2304 engages a connection interface 2012 of the medical connector 2000 just prior to contact being made between the tip 2021 of the luer 2020 and the seal region 2392. The connection interfaces 2342, 2012 thus can assist in the creation of a fluid-tight seal between the luer 2020 and the sealing member 2390.

The sealing member 2390 can remain in the initial or pre-use position that is shown in both FIGS. 41 and 42 until the seal has been formed between the luer 2020 and the sealing member 2390. Further advancement of the luer 2020 into the disinfection chamber 2358 can strengthen the seal due to the spring force that arises as the pad 2370 is compressed. When the sealing member 2390 is in the initial orientation, the ports 2394 can prevent antiseptic 2333 from passing through them. Also, the composition of the pad 2370 or the affinity of the pad 2370 to absorb antiseptic 2333 will determine the retention of the antiseptic 2333 in the pad 2370.

Figure 43:
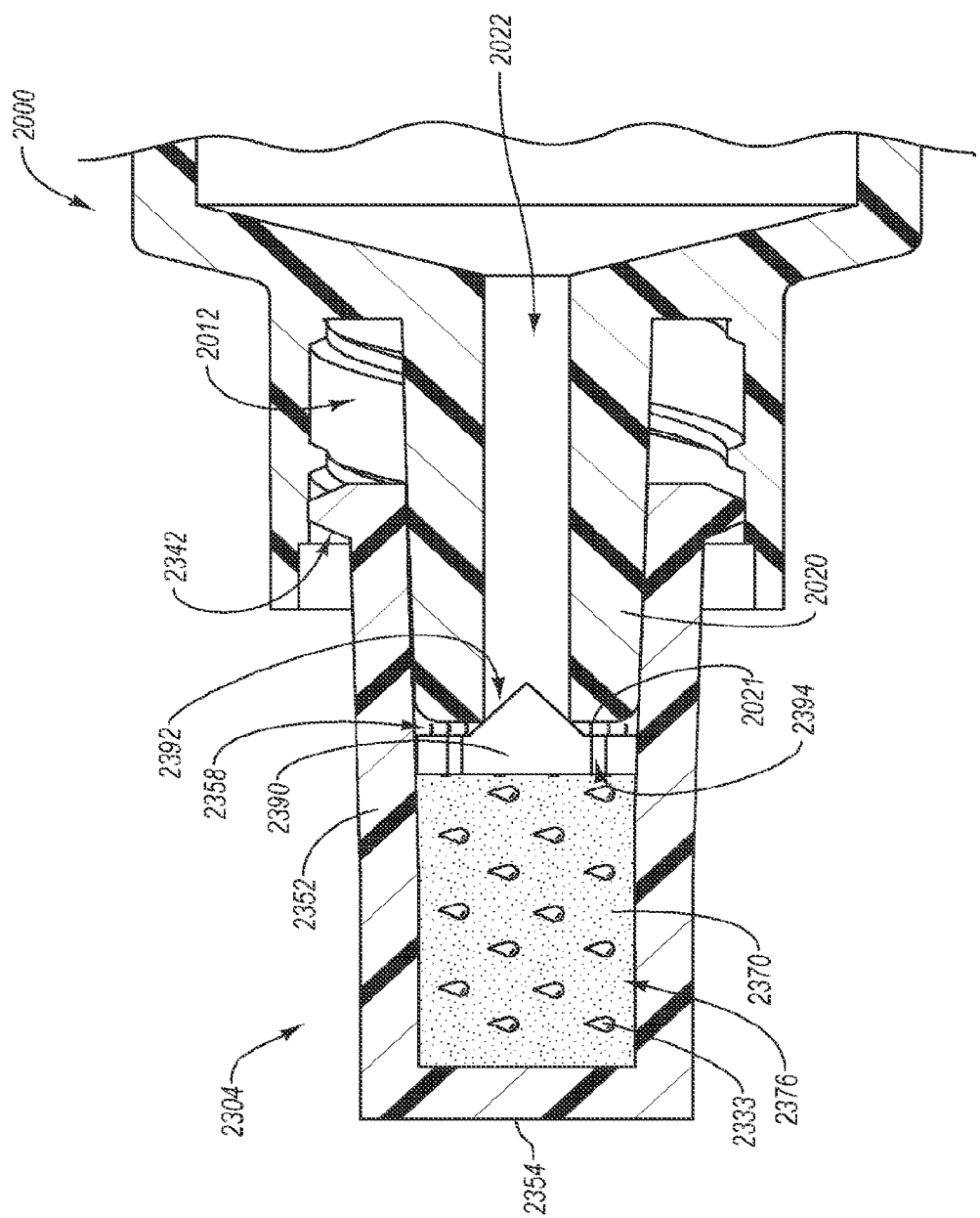
FIG. 43 is a cross-sectional view such as that of FIG. 41 showing a yet later stage of coupling the cap with the medical connector in which a pad is compressed so as to expel antiseptic therefrom through the sealing member and in which the male protrusion has not yet formed a fluid-tight seal with a sidewall of the medical connector.

In FIG. 43, the luer 2020 has been advanced slightly further into the disinfection chamber 2358, thereby compressing the pad 2370 somewhat and forcing antiseptic 2333 through the ports 2394. As schematically shown by wavy lines, the antiseptic 2333 begins to fill the space between the sealing member 2390 and the tip 2021 of the luer 2020. The antiseptic 2333 does not, however, enter into a lumen of the luer 2020 due to the seal between the luer 2020 and the sealing member 2390.

Figure 44:
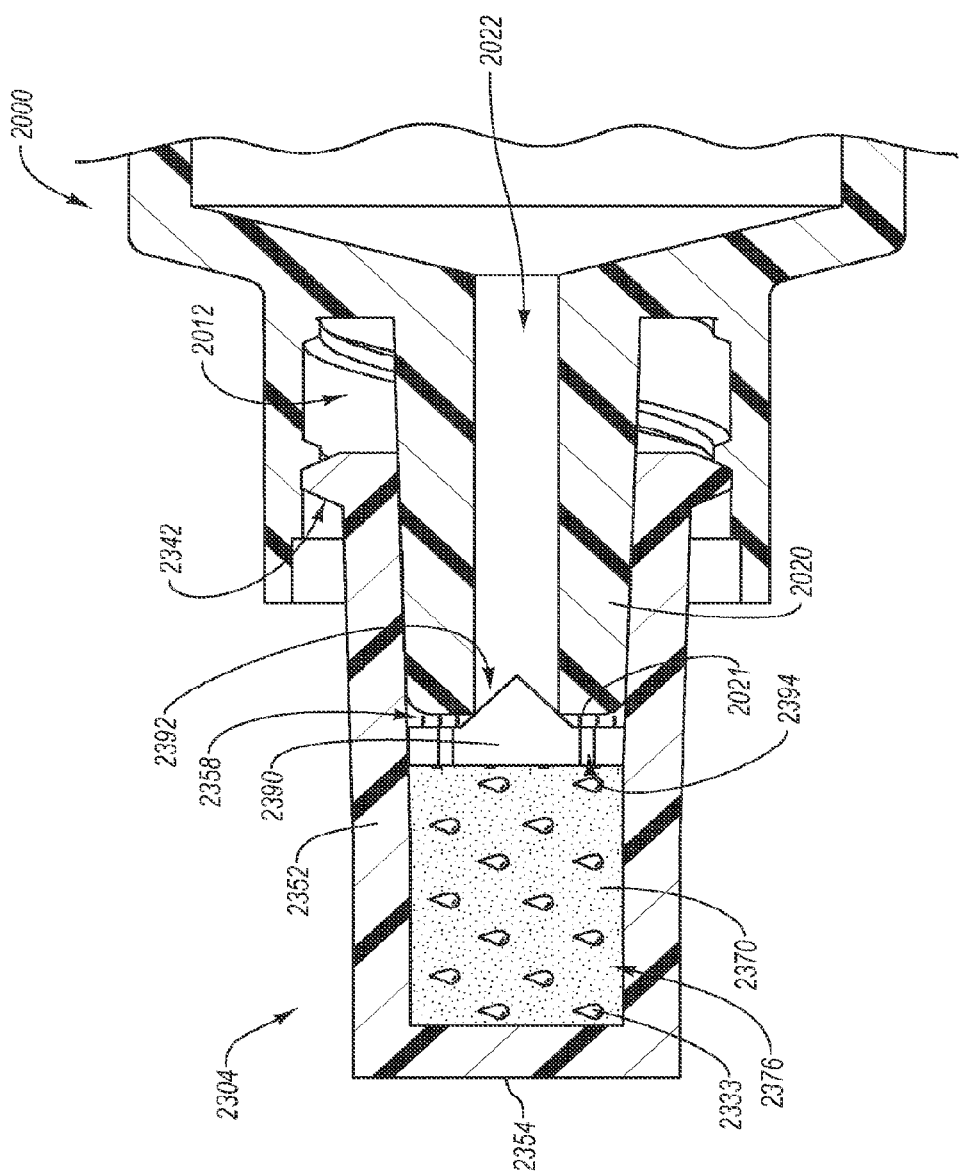
FIG. 44 is a cross-sectional view such as that of FIG. 41 showing a yet later stage of coupling the cap with the medical connector in which the pad is compressed further so as to expel additional antiseptic therefrom through the sealing member and in which the male protrusion has not yet formed a fluid-tight seal with a sidewall of the medical connector.

In FIG. 44, the luer 2020 has been advanced even further into the disinfection chamber 2358, thereby compressing the pad 2370 to a greater extent and forcing additional antiseptic 2333 through the ports 2394. Although the outer surface of the luer 2020 appears to be nearly parallel to and in contact with an inner surface of the tapered portion of the sidewall 2352, a seal has not yet been formed in this area. Accordingly, the antiseptic 2333 can fill not only the space between the sealing member 2390 and the tip 2021 of the luer 2020, but also the small amount of space between the luer 2020 and the sidewall 2352. The luer 2020 thus can be covered in antiseptic 2333 and disinfected thereby. In some embodiments, the antiseptic 2333 remains within portions of the space between the luer 2020 and the sidewall 2352 only temporarily, as additional advancement of the luer 2020 can close this space to form a seal.

Figure 45:
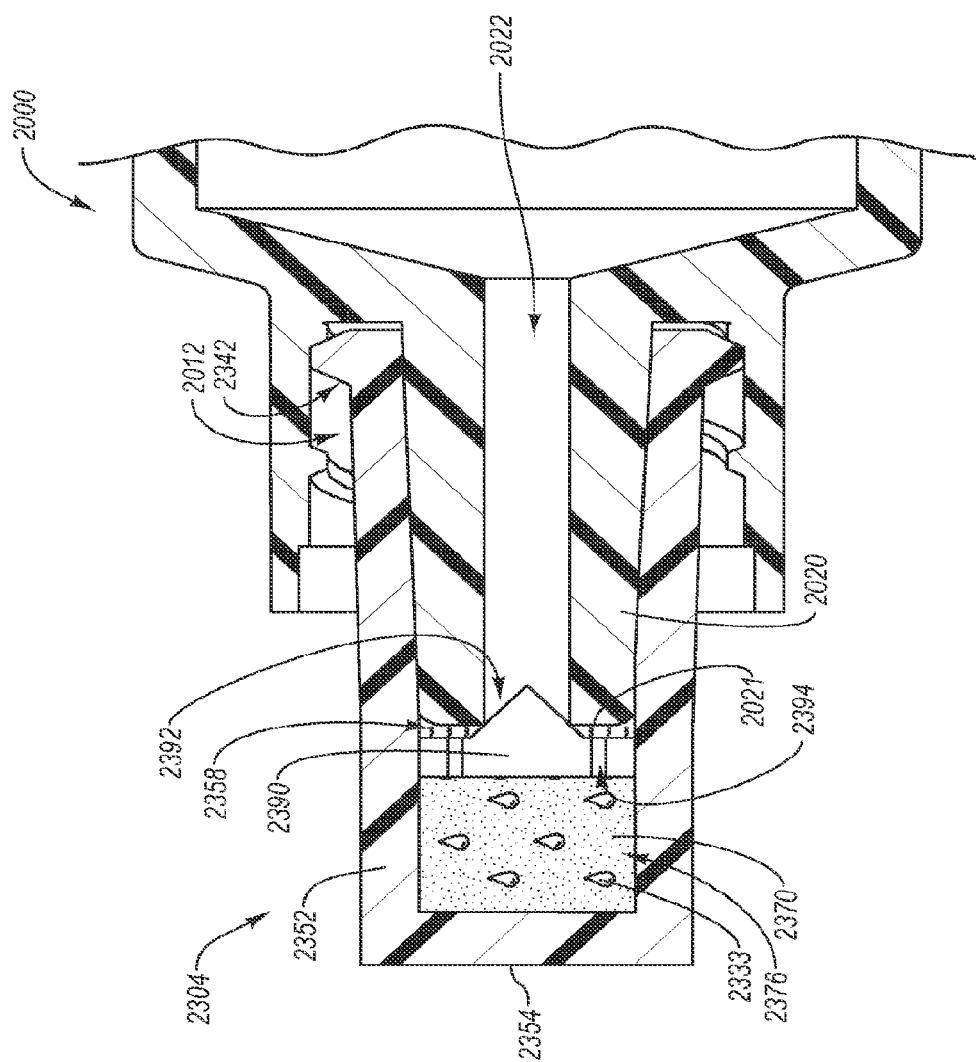
FIG. 45 is a cross-sectional view such as that of FIG. 41 showing a yet later stage of coupling the cap with the medical connector in which that pad is compressed even further so as to expel additional antiseptic therefrom through the sealing member and in which the male protrusion forms a fluid-tight seal with a sidewall of the medical connector.

FIG. 45 illustrates a final or fully coupled stage, or an end-of-stroke orientation, in which the luer 2020 has been advanced even further into the disinfection chamber 2358 such that the luer 2020 forms a seal with the sidewall 2352. Antiseptic 2333 can be retained in all open portions of the disinfection chamber 2358 that are between the seal formed by the luer 2020 and the sealing member 2390 and the seal formed by the luer 2020 and the sidewall 2352. In the illustrated embodiment, only a small portion of the luer 2020, which includes the tip 2021, is in continual contact with the portion of the antiseptic 2333 thus retained. This portion of the luer 2020 can be bathed by the antiseptic 2333 and disinfected thereby. In other embodiments, larger portions of the luer 2020 can be bathed.

In some embodiments, the seal formed by the luer 2020 and the sealing member 2390, and/or the seal formed by the luer 2020 and the sidewall 2352, can be accomplished by appropriate sizing of the individual components. In certain embodiments, the sizing is subject to and based upon the standardized ISO luer taper specification, such as discussed elsewhere herein.

In certain instances, the distance to which a particular luer 2020 is inserted into the chamber 2358 can vary from the distance to which a different luer 2020 may be inserted prior to sealing with the sidewall 2352. Similarly, in certain manufacturing processes, the dimensions of the sidewall 2352 may vary slightly from one cap 2304 to another, within a tolerance range, such that a given luer 2020 may extend into the chamber 2358 of one cap 2304 to a greater or lesser extent than it may extend into the chamber 2358 of another cap 2304.

For example, all manufactured components, such as the luer 2020 and the sidewall 2352 of the cap 2034, can vary within tolerance limits that range between a maximum material condition and a minimum material condition. The maximum and minimum material conditions can correspond to large and small components, respectively. All combinations of maximum and minimum material conditions for interoperable components can be considered to determine a maximum mating depth and a minimum mating depth for components that are within their respective tolerance ranges. Such maximum and minimum mating depths can represent the upper and lower values of an axial range of engagement.

For example, where both interoperable components (e.g., the luer 2020 and the sidewall 2352) exhibit their respective minimum material conditions, the maximum mating depth may be achieved. This maximum mating depth may also be referred to as a maximum stroke. In other words, the minimum material condition corresponds to the loosest fit. Conversely, the maximum material condition corresponds to the tightest fit of the taper.

In some embodiments, the axial range of engagement for the sidewall 2352 of the cap 2304 with a luer 2020 that is within standard tolerances is about 2 millimeters. In certain of such embodiments, a minimum dispense stroke of about 1 millimeter indicates that the components have been dimensioned such that for the tightest fitting luer 2020 (i.e., maximum material condition), a minimum of about 1 millimeter dispense stroke will exist. Hence, in this example, for any luer 2020 within an acceptable tolerance range, a minimum of about 1 millimeter of movement of the seal member 2390 can exist prior to engagement between the luer 2020 and the sidewall 2352. Other axial ranges of engagement, and other maximum and minimum dispense strokes, are also possible. For example, in various embodiments, an axial range of engagement for the cap 2304 can be no more than about 1, 2, 3, or 4 millimeters or no less than about 1, 2, 3, or 4 millimeters. In other or further embodiments, a minimum dispense stroke is no greater than about 0.5, 1.0, 1.5, or 2.0 millimeters.

Figure 46:
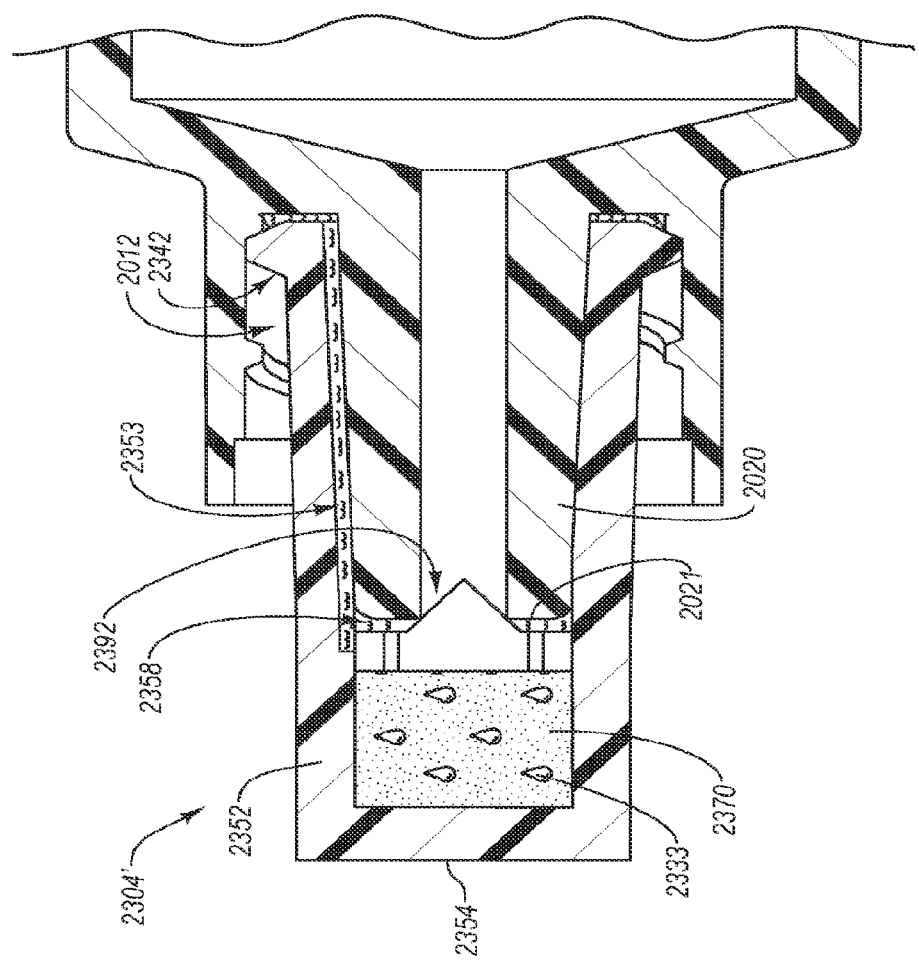
FIG. 46 is a cross-sectional view such as that of FIG. 41 showing another embodiment of cap coupled with a medical connector having a male protrusion.

FIG. 46 illustrates another embodiment of a cap 2304' in an end-of-stroke orientation. The cap 2304' is substantially the same as the cap 2304 just discussed. For example, a substantial portion of an interior surface of the sidewall 2352 is tapered so as to be complementary to the male luer 2020. However, the sidewall 2352 includes one or more venting channels or vents 2353 therein that prevent the sidewall 2352 from fully sealing with the male luer 2020. The illustrated vent 2353 extends from a proximal end of the sidewall 2352 in a longitudinal direction to a position just beyond (or distal of) an end-of-stroke position of the tip 2021 of the male luer 2020. Accordingly, after liquid-impervious contact is established between the male luer 2020 and those portions of the sidewall 2352 having a taper complementary to the male luer 2020, antiseptic 2333 can still exit the chamber 2358 via the vent 2353. In certain embodiments, the coupled connection interfaces 2012, 2342 can permit the antiseptic 2333 to pass through them so as to provide additional venting of the chamber 2358. For example, threaded connection interfaces 2012, 2342 can permit antiseptic 2333 that has exited from the chamber 2358 to spiral about an outer surface of the sidewall 2352 and/or otherwise seep in a distal direction.

In various embodiments, the cap 2304' comprises one or more, two or more, three or more, or four or more vents 2353. One or more of the vents 2353 can be substantially linear in a longitudinal direction (as shown) and/or can define alternate orientations. For example in some embodiments, one or more vents 2353 can be angled relative to a longitudinal axis of the cap 2304' (e.g., can be helical), or can include a portion that is so angled. One or more of the vents 2353 can extend any suitable distance between the proximal end of the sidewall 2352 and the base wall 2354. For example, in various embodiments, the vents 2353 extend no less than about ¼, no less than about ⅓, no less than about ½, no less than about ⅔, or no less than about ¾ the distance between the proximal end of the sidewall 2352 and the base wall 2354. Where suitable, one or more vents 2353 can be incorporated into embodiments of the caps described above, as well as those described hereafter.

Figure 47:
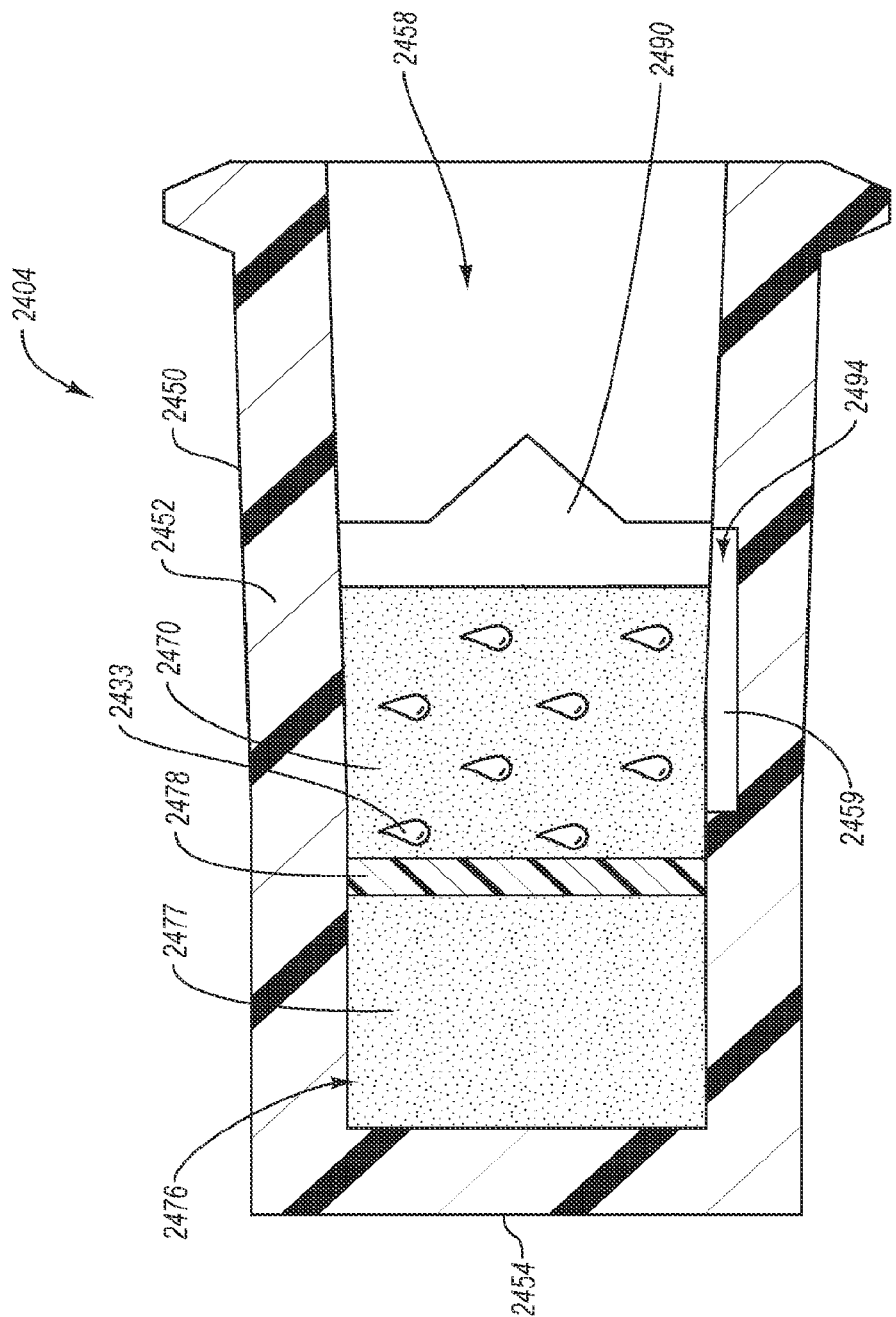
FIG. 47 is a cross-sectional view of another embodiment of a cap configured for coupling with a medical connector having a male protrusion.

FIG. 47 illustrates another embodiment of a cap 2404, which can resemble one or more of the caps described above, particularly the caps 2304, 2304', in certain respects. Accordingly, like features are designated with like reference numerals, with the leading digits incremented to "24." The cap can include a housing 2450, a biasing member 2476, and a sealing member 2490. The housing 2450 can have a sidewall 2452 and a base wall 2454 that define a disinfection chamber 2458. The housing 2450 can further define one or more ports 2494. In the illustrated embodiment, the port 2494 comprises a longitudinal channel or groove 2459 extending a distance along the sidewall 2452. The longitudinal distance which the groove 2459 extends can be varied as desired. In some embodiments, the longitudinal distance is greater than or equal to a stroke length through which the sealing member 2490 is displaced when the cap 2404 is connected to a medical connector for reasons discussed hereafter, although such is not required.

The sealing member 2490 can be devoid of channels, and may act in a plunger-like fashion. The sealing member 2490 can form a liquid-impermeable seal with the sidewall 2452 when in the pre-use configuration shown in FIG. 47. However, distal displacement of the sealing member 2490 can move a proximal end of the sealing member 2490 past a proximal end of the port 2494, thereby opening the port 2494. This can permit an antiseptic 2433 to be forced from a pad 2470 by the displaced sealing member 2490 and moved through the port 2494, thereby entering the portion of the disinfection chamber 2458 which is proximal to the sealing member 2490. In embodiments where the longitudinal length of a groove 2459 is greater than or equal to a stroke length through which the sealing member 2490 is displaced, antiseptic 2433 can be permitted to pass through the groove 2459 during all stages of the displacement. As can be appreciated from the foregoing, the port 2494 can comprise an opening, spacing, or gap that exists between a periphery or outermost perimeter of the sealing member 2490 and the sidewall 2452. The groove 2459 thus can also be described as a gap.

In the illustrated embodiment, the biasing member 2476 includes a resiliently compressible pad 2477, although additional or other components are possible (e.g., a compressible spring). The pad 2477 is separated from the pad 2470 by a barrier 2478, which can comprise any suitable material capable of preventing passage of the antiseptic 2433. For example, in some embodiments, the barrier 2478 comprises a plastic film or disk. The barrier 2478 thus can restrain the antiseptic 2433 to a predetermined portion of the disinfection chamber 2458 that is closest to the sealing member 2490. Such an arrangement can permit the usage of less antiseptic 2433, as a greater portion of the antiseptic 2433 can be expelled from the pad 2470.

In some embodiments, both of the pads 2470, 2477 comprise the same material, while in other embodiments different materials may be selected for desired properties. For example, the pad 2470 may comprise a more absorbent foam while the pad 2477 may comprise a springier foam. In some embodiments, both pads 2470, 2477 can provide a bias to the sealing member 2490 when they are compressed such that the biasing member 2476 can be said to include both pads 2470, 2477. In still other or further embodiments, the biasing member 2476 can comprise a spring or other at least somewhat resiliently deformable element in place of the pad 2477.

Although in the illustrated embodiment, the sealing member 2490 is devoid of ports, other embodiments can include ports in addition to or instead of the channels 2494 in the sidewall 2452. Likewise, it is understood that channels 2494 could be included in other embodiments of caps described herein in addition to or in place of ports through sealing members. Similar substitutions and rearrangements are possible with respect to other features of the cap 2404, such as the two-part biasing member 2476 and the barrier 2478.

Figure 48:
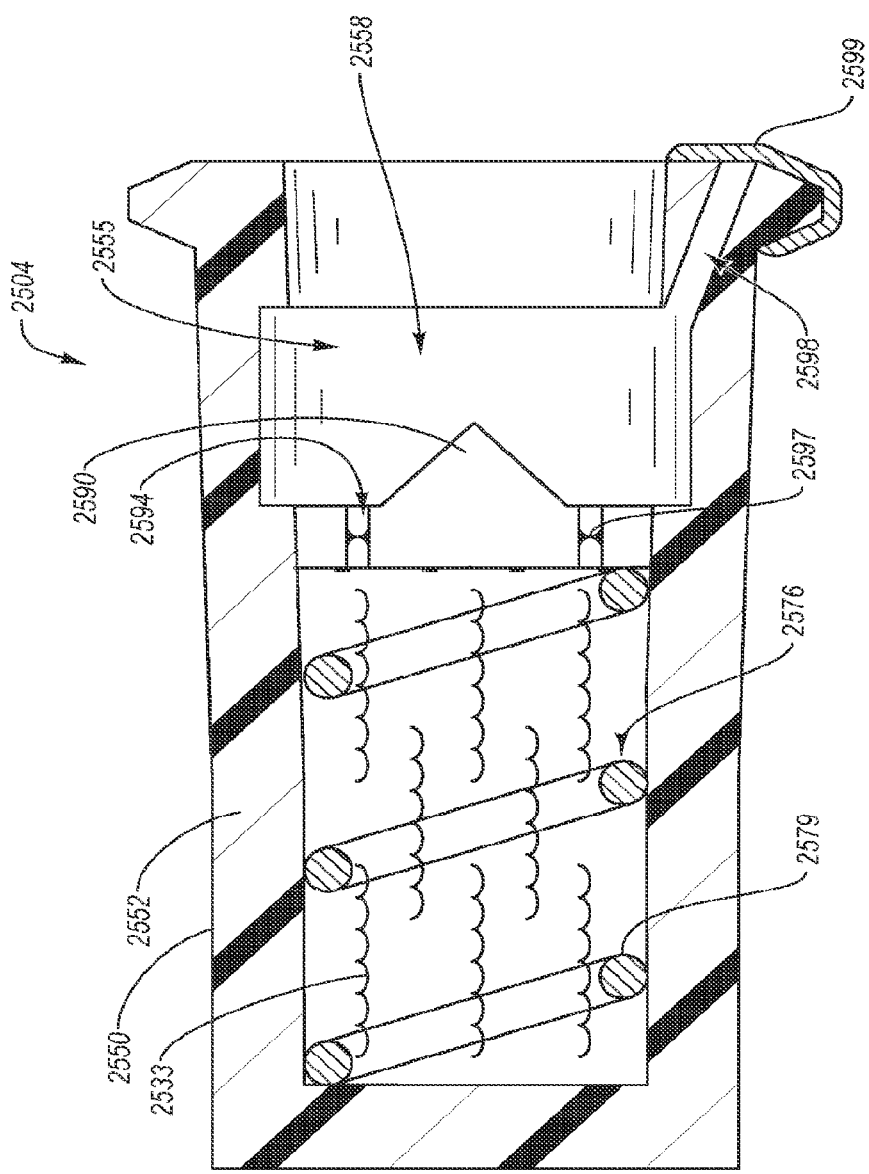
FIG. 48 is a cross-sectional view of yet another embodiment of a cap configured for coupling with a medical connector having a male protrusion.
Figure 49:
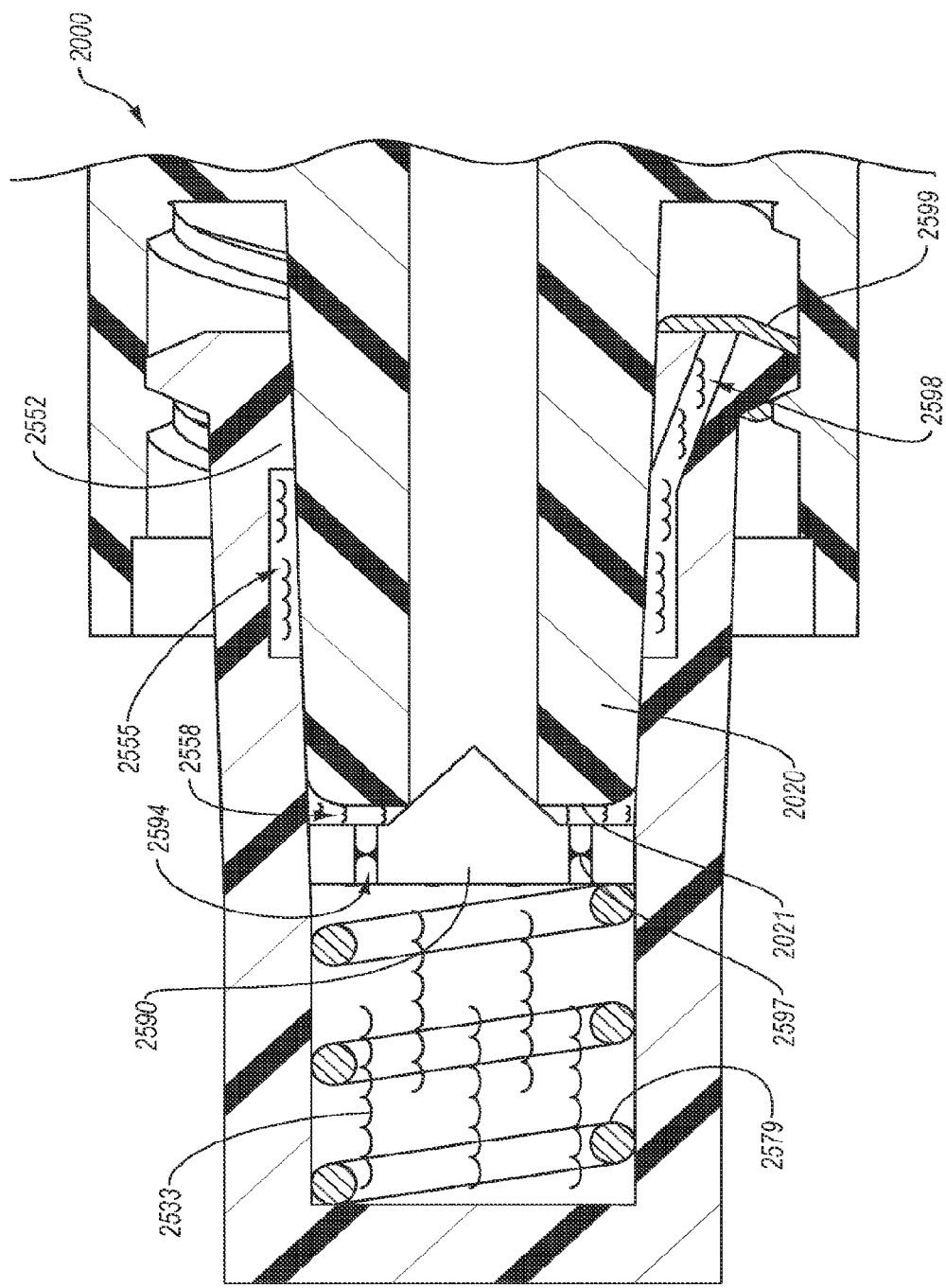
FIG. 49 is a cross-sectional view of the cap of FIG. 48 coupled with a medical connector having a male protrusion.

FIGS. 48 and 49 illustrate another embodiment of a cap 2504, which can resemble one or more of the caps described above, particularly the caps 2304, 2304', 2404, in certain respects. Accordingly, like features are designated with like reference numerals, with the leading digits incremented to "25." The cap can include a housing 2550, a biasing member 2576, and a sealing member 2590. The housing 2550 can have a sidewall 2552 that defines a disinfection chamber 2558. The housing 2550 can further define a bathing recess 2555 within the disinfection chamber 2558, which can be included in a tapered region at a proximal end of the sidewall 2552. As shown in FIG. 49, antiseptic 2533 can be retained within the bathing recess 2555 and maintained in contact with an outer surface of a male luer 2020. Accordingly, a greater portion of the luer 2020 than just a tip 2021 thereof can be maintained in contact with the antiseptic 2533 when the luer 2020 is in an end-of-stroke position.

The housing 2550 can further define a vent 2598 having a cover 2599. The vent 2598 can be defined by a channel that extends from an interior of the sidewall 2552 to an exterior thereof. A distal end of the vent 2598 can open into the bathing recess 2555, and a proximal end of the vent 2598 can be at a proximal end of the sidewall 2552. The vent 2598 can function in manners such as those described above with respect to other vents.

In some embodiments, the cover 2599 can comprise a material, such as, for example, Tyvek® or other nonwoven material, which can filter microbes from the air entering the disinfection chamber 2558 via the vent 2598 and can permit antiseptic 2533 to exit from the disinfection chamber 2558.

With continued reference to FIGS. 48 and 49, the antiseptic 2533 can be held within the disinfection chamber 2533 without pads. A biasing member 2576 can include a compression spring 2579. A sealing member 2590 can form a fluid-tight seal with the sidewall 2552 to retain the antiseptic 2533 within a reservoir portion of the chamber 2533. While the sealing member 2590 can resemble any of the sealing members discussed above, the illustrated embodiment includes ports 2594 that have two-way valves 2597 therein. In various embodiments, the two-way valves 2597 are formed of self-sealing slits and/or the two-way valves 2597 can be disposed within channels through the sealing member 2590.

Figure 50:
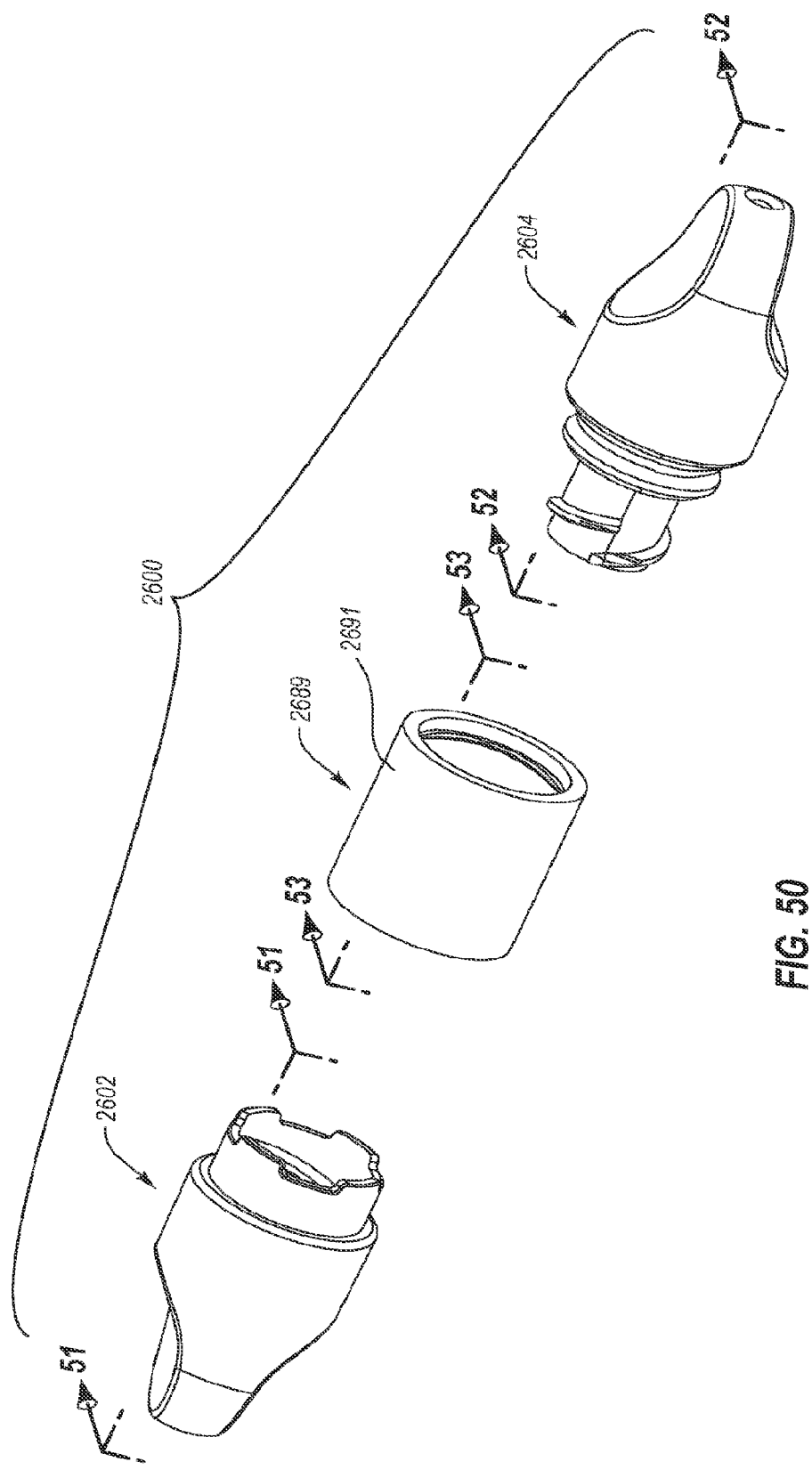
FIG. 50 is an exploded perspective view of another embodiment of an assembly that includes a female cap and a male cap, which can be connected in a pre-use configuration via a sleeve.

FIG. 50 illustrates another embodiment of an assembly 2600, which can resemble one or more of the assemblies described above, particularly the assembly 1800, in certain respects. Accordingly, like features are designated with like reference numerals, with the leading digits incremented to "26." The assembly 2600 can include a cap 2602 and cap 2604 that are coupled with each other when in a pre-use state and that can be removed from each other. In particular, the caps 2602, 2604 can be coupled with each other via a sealing mechanism 2689. In the illustrated embodiment, the caps 2602, 2604 are coupled with each other via a sealing sleeve 2691.

With reference to FIG. 51, the cap 2602 can include a housing 2610, which can include a sidewall 2612 and a base wall 2613. The housing 2610 can include a substantially cylindrical region toward a proximal end thereof, which can be flattened and taper toward the narrower base wall 2613. Such a shape can provide a convenient handle at a distal end of the cap 2602. A cavity 2623 can be formed at an interior of the sidewall 2612 and the base wall 2613, which can reduce material costs for the cap 2602.

The sidewall 2612 can define a disinfection chamber 2622, which can include a connection interface 2630 that includes threads 2631. The connection interface 2630 can be configured to attach the cap 2602 to a medical connector in a secure yet selectively removable manner. The disinfection chamber 2622 can further include a pad 2632.

A proximal surface 2624 of the sidewall 2612 can define a seal inhibitor 2625 that is configured to prevent the cap 2602 from forming a fluid-tight seal with a medical connector, such as a needleless injection site, when it is coupled therewith. For example, in the illustrated embodiment, the proximal surface 2624 of the sidewall 2612 is substantially castellated such that it defines a series of offset contact regions 2626 and venting regions 2627. In the illustrated embodiment, each of the contact regions 2626 and venting regions 2627 includes a planar surface that is substantially perpendicular to a longitudinal axis of the cap 2602. The contact regions 2626 are at a more proximal position than are the venting regions 2627. Accordingly, when the cap 2602 is coupled with certain embodiments of needleless injection sites, the contact regions 2626 can come into contact with surfaces of the needleless injection sites that project radially outwardly, whereas the venting regions 2627 can avoid making any such contact.

For example, in arrangements such as those depicted in FIGS. 32 and 33, the cap 2602 can be advanced onto a needleless injection site 2040, 2060 sufficiently to bring the planar surfaces of the contact regions 2626 into contact with radially outwardly projecting planar surfaces of the needleless injection site 2040, 2060. However, in such a configuration, the venting regions 2627 would be spaced from the outwardly projecting planar surface of the needleless injection site 2040, 2060 so as not to form a seal therewith. The cap 2602 thus would be permitted to vent via the venting regions 2627. As further discussed below, other configurations of the seal inhibitor 2625 are also possible. Moreover, in some embodiments, the cap 2625 is devoid of a seal inhibitor 2625.

With reference to FIGS. 51 and 53, an exterior surface of the sidewall 2612 can define another connection interface 2640 that is configured to couple the cap 2602 with a connection interface 2695 of the sleeve 2691. In the illustrated embodiment, the connection interfaces 2640, 2695 couple with each other via a friction-fit engagement. The friction fit can be sufficiently strong to provide a fluid-tight seal between the cap 2602 and the sleeve 2691, yet can allow the cap 2602 to be removed from the sleeve 2691 via mere manipulation by a medical practitioner (e.g., without the use of ancillary tools). The fluid-tight seal can prevent evaporative loss of antiseptic from the pad 2632 and/or can maintain the sterility of the disinfection chamber 2622. In other or further embodiments, the connection interfaces 2640, 2695 can include threads or other suitable attachment features.

The cap 2602 can include a flange 2615 having an outer diameter larger than an inner diameter of the end of the sleeve 2691 that connects with the cap 2602. The flange 2615 can prevent the cap 2602 from being inserted into the sleeve 2691 too deeply. In other or further embodiments, the flange 2615 can cooperate with an end surface of the sleeve 2691 to create a fluid-tight seal (see FIG. 54). For example, in some embodiments, a sealing member, such as an O-ring, is included between the flange 2615 and the end of the sleeve 2691 to provide the fluid-tight seal.

With reference to FIG. 52, the cap 2604 can include a housing 2650 that includes a sidewall 2652 and a base wall 2654, which can cooperate to define a cavity 2659 similar to the cavity 2623 described above. Likewise, the housing 2650 can define a substantially cylindrical shape at a proximal end of the cap 2604, which flattens and tapers toward the base wall 2654.

The sidewall 2652 can define a disinfection chamber 2658, which can include a sealing member 2690 and a biasing member 2676. The sealing member 2690 and the biasing member 2676 can resemble any suitable combination of these components, and features thereof, described above. In the illustrated embodiment, the biasing member 2676 comprises a pad 2670.

A portion of the sidewall 2652 can define a connection interface 2642, which includes one or more threads 2643 in the illustrated embodiment. The connection interface 2642 can be configured to attach the cap 2604 to a medical connector in a secure yet selectively removable manner.

With reference to FIGS. 52 and 53, the sidewall 2652 can define an additional connection interface 2680, which can cooperate with a connection interface 2692 defined by the sleeve 2691 to couple the cap 2604 with the cap 2602. The connection interface 2680 of the cap 2604 can include a groove 2683, which may be substantially annular and extend about a periphery of the cap 2604. The connection interface 2692 of the sleeve 2691 can include a complementary inward projection 2693, which likewise can be substantially annular. The interfaces 2680, 2692, when coupled with each other, can provide a fluid-tight seal between the cap 2604 and the sleeve 2691. In other embodiments, the connection interfaces 2680, 2692 can instead define a friction-fit seal, such as that provided by the illustrated embodiment of the connection interfaces 2640, 2695 described above. In still other or further embodiments, a flange 2661 defined by the housing 2650 can cooperate with an end surface of the sleeve 2691 to create a fluid-tight seal (see FIG. 54), which can prevent evaporative loss of antiseptic from the pad 2670 and/or maintain the sterility of the disinfection chamber 2658. For example, in some embodiments, a sealing member, such as an O-ring, is included between the flange 2659 and the end of the sleeve 2691 to provide the fluid-tight seal.

Figure 54:
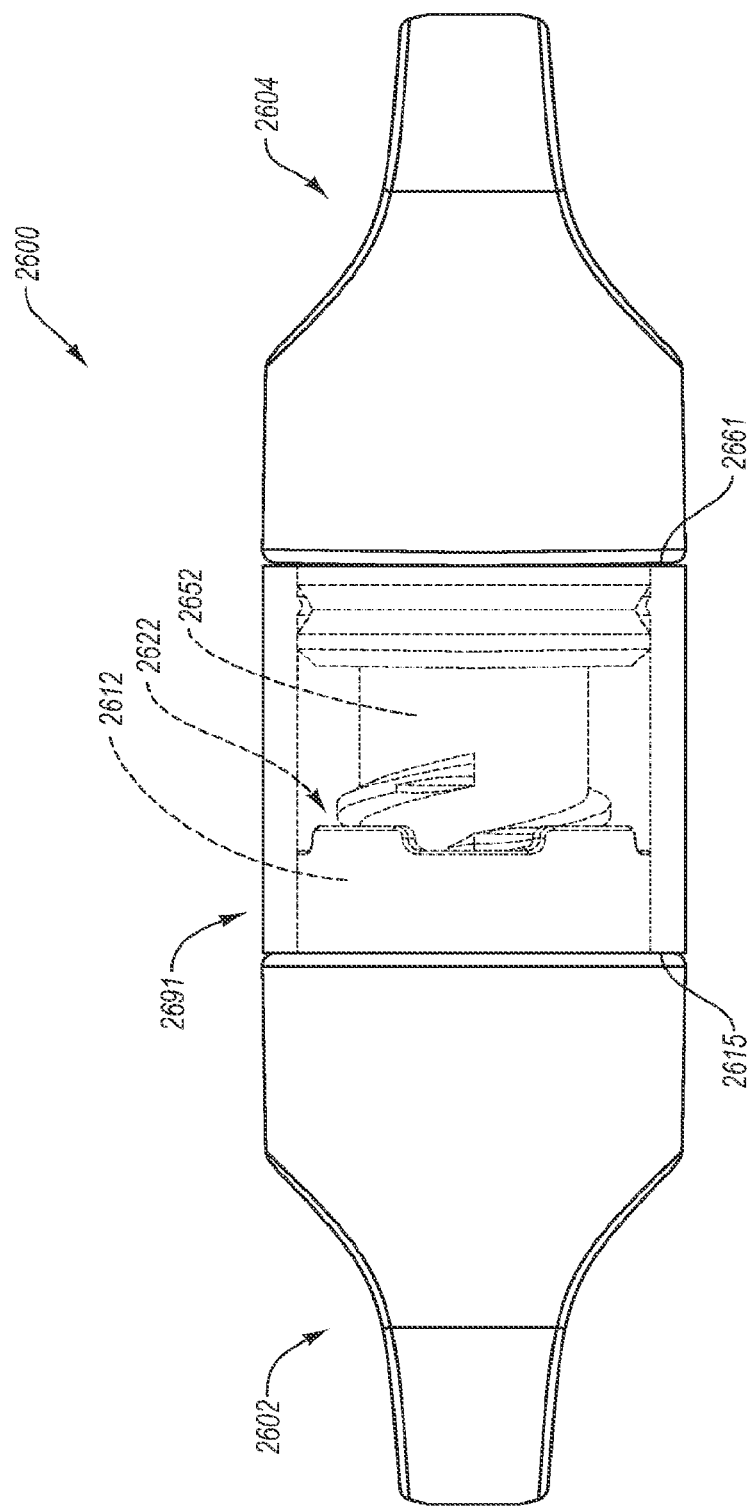
FIG. 54 is an elevation view of the assembly of FIG. 50 shown in a pre-use configuration.

With reference to FIG. 54, when the assembly 2600 is in a fully coupled or pre-use state, a proximal end of the sidewall 2652 of the cap 2604 is received within the cavity 2622 defined by the sidewall 2612 of the cap 2602. In some embodiments, the sidewall 2652 of the cap 2604 does not contact any portion of the sidewall 2612 of the cap 2602 in this pre-use configuration, nor does the sidewall 2652 contact the pad 2632 that is within the cap 2602. Such a configuration can result in a relatively compact assembly 2600 in which each cap 2602, 2604 can be quickly prepared for use. In other embodiments, the sidewalls 2652, 2612 may contact or couple with each other (e.g., via the connection interfaces 2642, 2630) and/or the sidewall 2652 may contact the pad 2632 in the pre-use configuration. In still other embodiments, the sidewalls 2652, 2612 may be spaced from each other such that the sidewall 2652 is not received within the cavity 2622.

Figure 55:
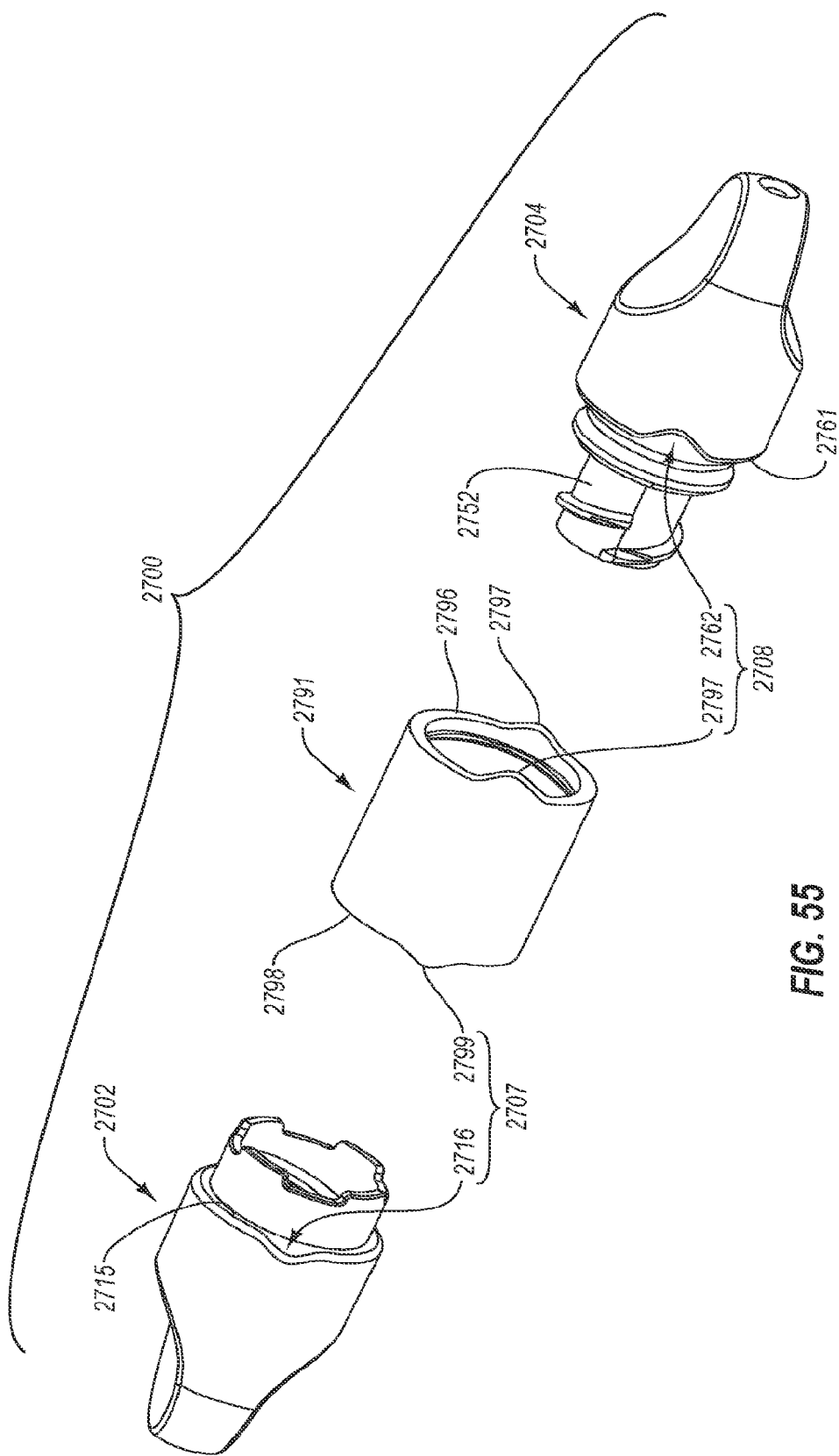
FIG. 55 is an exploded perspective view of another embodiment of an assembly that includes a female cap and a male cap, which can be connected in a pre-use configuration via a sleeve and that includes separation assists.

FIG. 55 illustrates another embodiment of an assembly 2700, which can resemble one or more of the assemblies described above, particularly the assemblies 1800, 2600, in certain respects. Accordingly, like features are designated with like reference numerals, with the leading digits incremented to "27." The assembly 2700 can include a cap 2702 and cap 2704 that are coupled with each other when in a pre-use state via a sealing sleeve 2791.

The assembly 2700 can include one or more separation assists 2707, 2708, which can aid in removal of the cap 2702 and/or the cap 2704 from the sleeve 2791. In the illustrated embodiment, the separation assists 2707, 2708 each includes a complementary recess/protrusion pair. In particular, a flange 2715 of the cap 2702 defines a recess 2716 that is sized and dimensioned to receive therein a protrusion 2799 that is defined by an edge 2798 of the sleeve 2791. The recess 2716 and the protrusion 2799 cooperate with each other as a separation assist 2707. Similarly, a flange 2761 of the cap 2704 defines a recess 2762 that is sized and dimensioned to receive therein a protrusion 2797 that is defined by an edge 2796 of the sleeve 2791. The recess 2762 and the protrusion 2797 cooperate with each other as a separation assist 2708.

Focusing now on the separation assist 2707, the recess 2716 can include two substantially planar surfaces that meet at a rounded base. The planar surfaces can be at an angle relative to a plane that is perpendicular to a longitudinal axis (or central axis) of the cap 2702 (e.g., a plane defined by portion of the flange 2715 that does not include the recess 2716, in the illustrated embodiment). For example, in the illustrated embodiment, each of the planar surfaces of the recess 2716 defines an angle of about 20 degrees relative to the perpendicular plane. Similarly, the protrusion 2799 can include two substantially planar surfaces that meet at a rounded apex. The planar surfaces can be at the same angle relative to the perpendicular plane as are the planar surfaces of the recess 2716. For example, in the illustrated embodiment, each of the planar surfaces of the protrusion 2799 defines an angle of about 20 degrees relative to a plane defined by the portion of the edge 2798 of the sleeve 2791 that does not include the protrusion 2799.

When the cap 2702 is joined with the sleeve 2791 in a pre-use configuration (similar to that shown in FIG. 54), the planar portions of the recess 2716 and of the protrusion 2799 can be in close proximity to each other or can contact each other. In order to separate the cap 2702 from the sleeve 2791, the cap 2702 can be rotated relative the sleeve 2791, which can cause opposing planar surfaces of the recess 2716 and the protrusion 2799 to contact each other and slide past each other. This interaction can convert the rotational movement of the cap 2702 about a common axis of the cap 2702 and the sleeve 2791 into translational movement of the cap 2702 away from the sleeve 2791 along the common axis. Due to the symmetry of the planar surfaces of each of the recess 2716 and the protrusion 2799 of the illustrated embodiment, the cap 2702 can be rotated in either direction to achieve the same lifting action via the separation assist 2707 that tends to move the cap 2702 away from the sleeve 2791.

In other embodiments, the separation assist 2707 can be configured to aid in separating the cap 2702 from the sleeve 2791 only when the cap 2702 is rotated in one predetermined direction (e.g., either clockwise or counterclockwise). For example, one planar surface may be at about 20 degrees relative to the perpendicular plane, whereas the other planar surface may be at a about 90 degrees relative to the perpendicular plane (i.e., approximately parallel to or extending through a central axis of the cap 2702). In other embodiments, one or more of the planar surfaces of the recess 2716 and/or the protrusion 2799 may be at larger or smaller angles relative to the perpendicular plane. For example, in various embodiments, a set of complementary planes may be at an angle of no more than about 15 degrees, no more than about 20 degrees, no more than about 30 degrees, no more than about 45 degrees, no more than about 60 degrees, or no more than about 75 degrees. Other configurations of the separation assist 2707 are also possible. For example, in some embodiments, the complementary surfaces of the recess 2716 and the protrusion 2799 can define angles as just described, but the surfaces may be rounded or otherwise non-planar.

The foregoing discussion regarding the separation assist 2707 applies equally to the separation assist 2708. In the illustrated embodiment, the separation assist 2707 and the separation assist 2708 are substantially identical, such that the recess 2762 and the protrusion 2797 likewise include complementary planar surfaces that are at an angle of about 20 degrees relative to a plane oriented perpendicularly through a central axis of the cap 2704 and the sleeve 2791. In other embodiments, the arrangements of the separation assists 2707, 2708 may be different from each other. For example, the planar surfaces of the separation assist 2707 may be at a larger or smaller angle than those of the separation assist 2708 so as to provide a different amount of separation force. Moreover, in some embodiments, the assembly 2700 includes a number of separation assists 2707 equal to the number of separation assists 2708, whereas in other embodiments, the assembly 2700 may include more or fewer separation assists 2707 as compared with the number of separation assists 2708. For example, in the illustrated embodiment, the assembly 2700 includes one separation assist 2707 and two separation assists 2708.

In the illustrated embodiment, the two separation assists 2708 are at diametrically opposite positions. Such an orientation can aid in maintaining the cap 2704 and the sleeve 2791 in a substantially coaxial orientation as the cap 2704 is being removed, which can prevent an elongated sidewall 2752 from contacting an inner surface of the sleeve 2791 and thereby potentially complicating removal of the cap 2704. In other arrangements, additional separation assists 2708 may be used, and the separation assists 2708 may be equally spaced from each other about a perimeter of the sleeve 2791.

Other arrangements of the separation assists 2707, 2708 are contemplated. For example, in some embodiments, the caps 2702, 2704 include one or more of the protrusions 2799, 2797, respectively, whereas the sleeve 2791 includes one or more of the recesses 2716, 2762.

Figure 56:
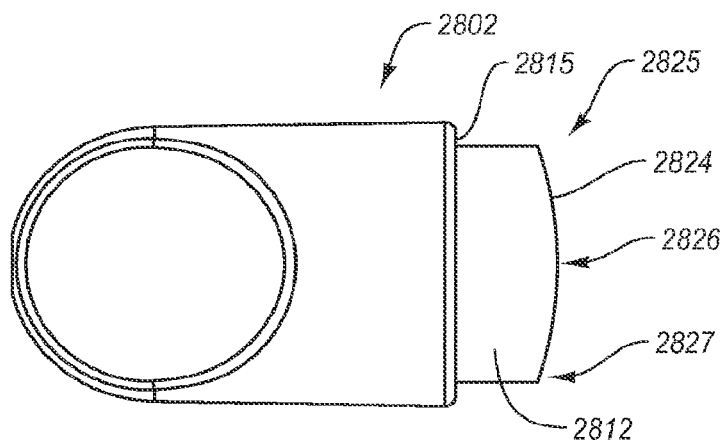
FIG. 56 is an elevation view of an embodiment of a cap that includes a seal inhibitor.
Figure 57:
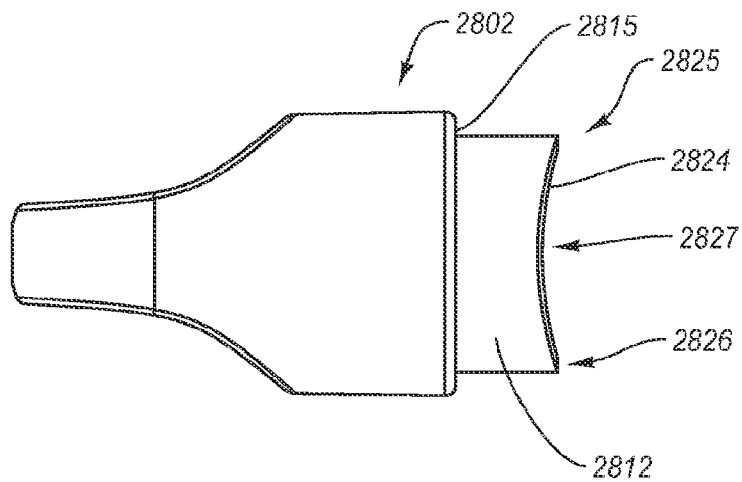
FIG. 57 is another elevation view of the cap of FIG. 56 showing a different face thereof.

FIGS. 56 and 57 illustrate another embodiment of a cap 2802, which in some embodiments can be used in place of the cap 2602 in the assembly 2600. In other embodiments, the cap 2802 can be modified so as to be used in place of the cap 2702 in the assembly 2700, such as by altering a flange 2815 of the cap 2802 to include a recess.

The cap 2802 can include a seal inhibitor 2825 having a different arrangement from that shown with respect to the caps 2602, 2702. In the illustrated embodiment, the seal inhibitor 2825 is defined by a proximal surface 2824 of a sidewall 2812 of the cap 2802, which defines a rounded, sinusoidal contour. In particular, the proximal surface 2824 can define two contact regions 2826 and two venting regions 2827. In the illustrated embodiment, the contact regions 2826 are at diametrically opposite positions and the venting regions 2827 likewise are at diametrically opposite positions. The contact regions 2626 are at a more proximal position than are the venting regions 2627. As discussed above with respect to the cap 2602, the venting regions 2827 can prevent the cap 2802 from forming a seal with a medical connector, and can permit venting of the cap 2802 when it is coupled with the medical connector.

Figure 58:
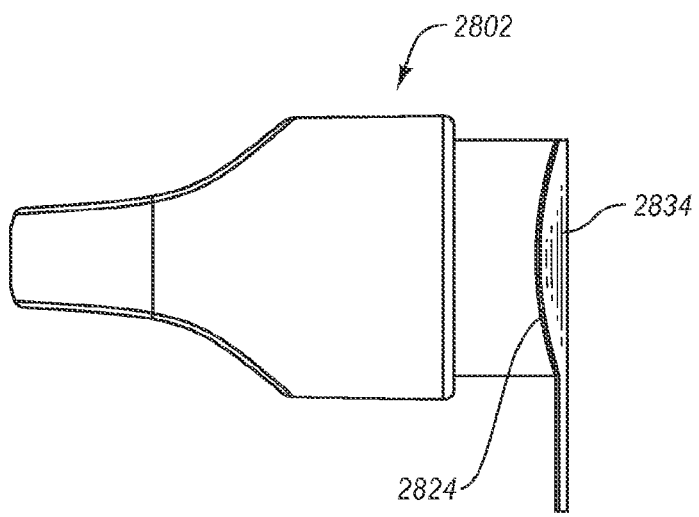
FIG. 58 is an elevation view of the cap of FIG. 56 coupled with a removable cover.

As shown in FIG. 58, the proximal surface 2824 of the cap 2802 can be well-suited for coupling with a removable cover 2834 such as the removable covers discussed above. Accordingly, various embodiments of the cap 2802 either can be readily fitted with a cover 2834 and distributed for individual use, or can be incorporated into an assembly, such as the assemblies 2600, 2700 described above, and distributed for use in a dual-cap system. Such versatility can reduce manufacturing costs, such as by eliminating tooling costs.

FIGS. 59-63 illustrate another embodiment of an assembly 3000, which can resemble one or more of the assemblies described above, particularly the assemblies 2600 and 2700, in certain respects. Accordingly, like features are designated with like reference numerals, with the leading digits incremented to "30," and/or with identical or similar names.

Figure 59:
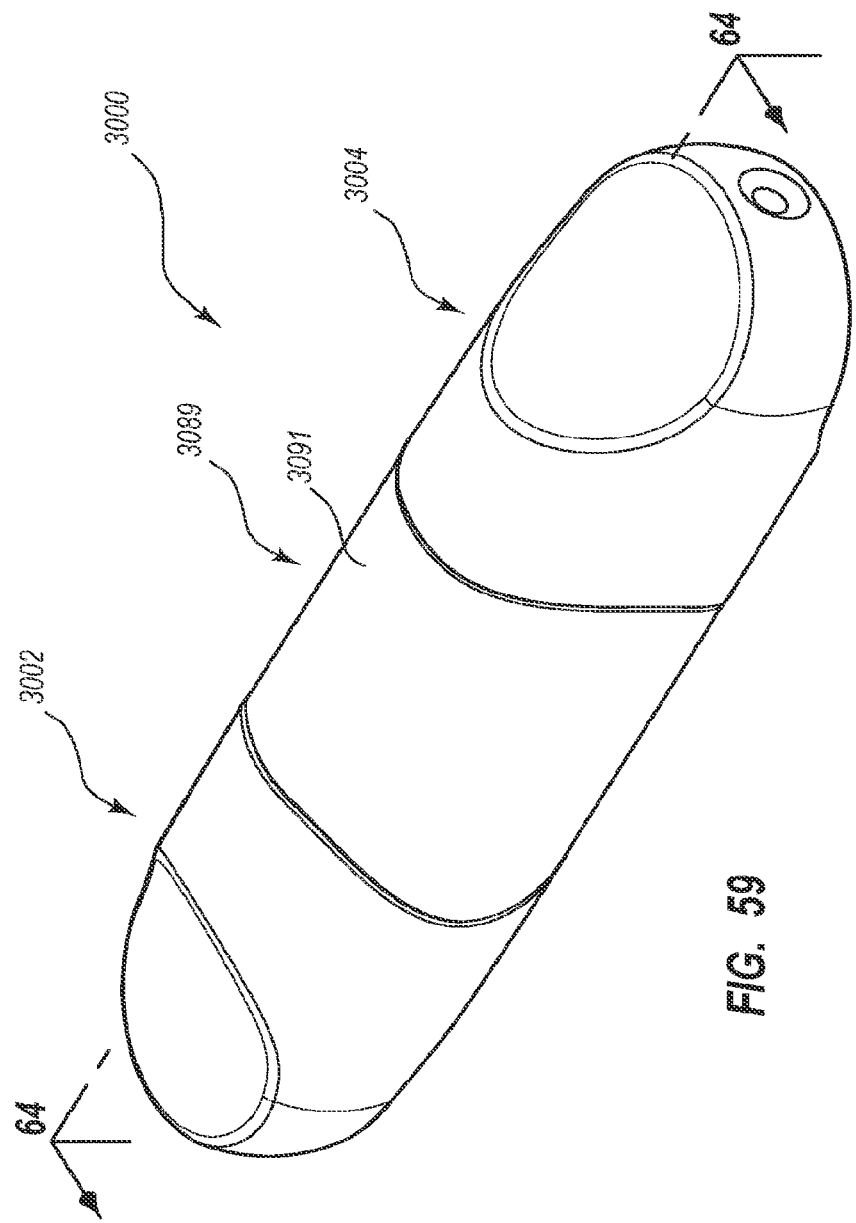
FIG. 59 is a perspective view of another embodiment of an assembly that includes a female cap and a male cap, which can be connected in a pre-use configuration via a sleeve.

As shown in FIG. 59, the assembly 3000 can include a female cap 3002 and a male cap 3004 that are coupled with each other when in a pre-use state and that can be removed from each other. In particular, the female and male caps 3002, 3004 can be coupled with each other via a sealing mechanism 3089. In the illustrated embodiment, the sealing mechanism 3089 comprises a sealing sleeve 3091. The terms "coupled" and variants thereof are used in their ordinary sense and include arrangements such as that illustrated in FIG. 1, in which the connecting geometries, connection interfaces, or threads 122, 114 of the caps 102, 104 directly engage one another when the assembly 100 is in the assembled or pre-use state. The terms also include arrangements such as that illustrated in FIG. 59 where the caps 3002, 3004 do not directly contact one another when the assembly 3000 is in the assembled or pre-use state, yet are securely held in a fixed relationship relative to one another. Stated otherwise, each of the caps 3002, 3004 is separately secured to the sealing sleeve 3091, and thus, although the caps 3002, 3004 are spaced from one another, they nevertheless are indirectly secured to each other.

Figure 60:
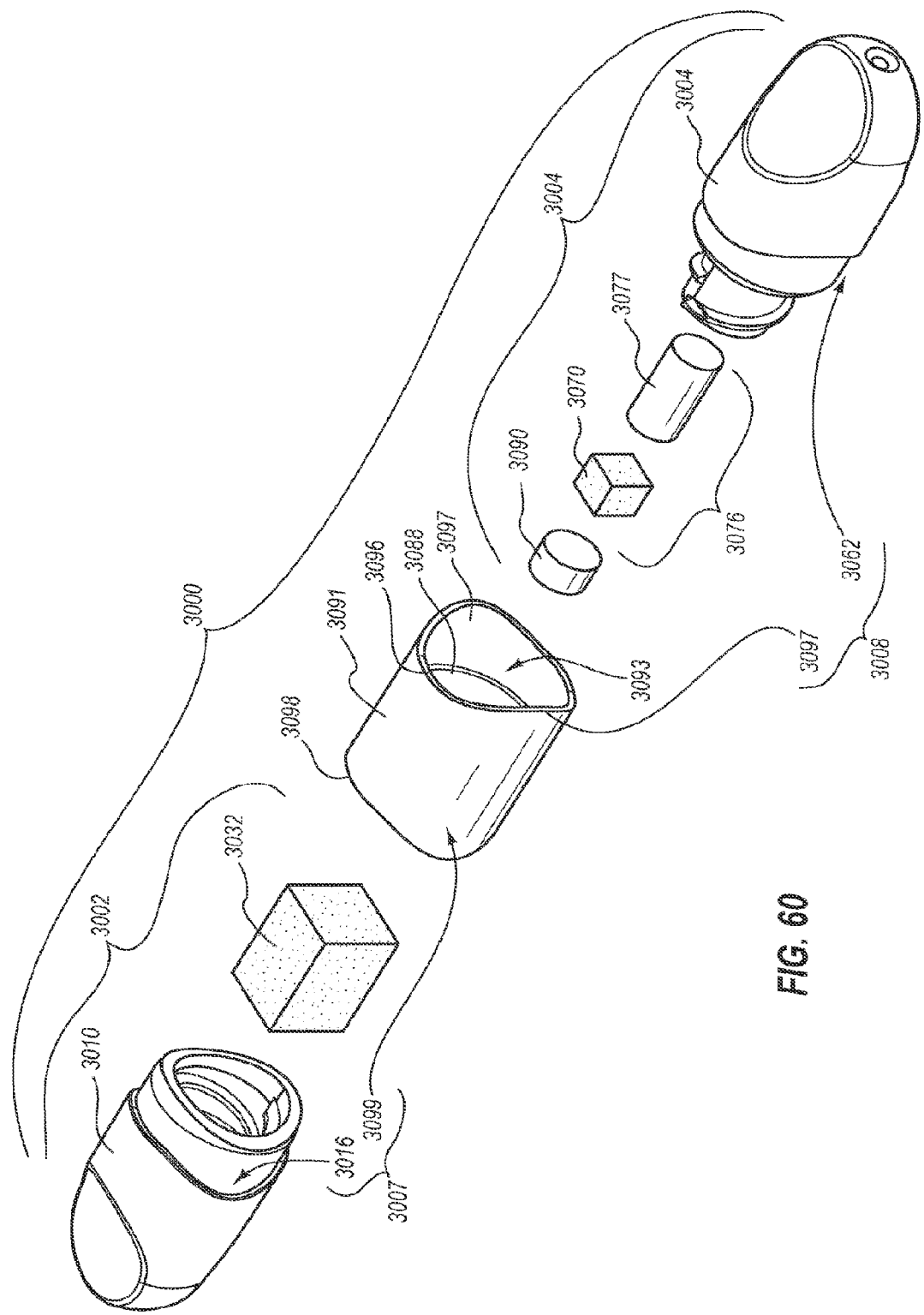
FIG. 60 is an exploded perspective view of the assembly of FIG. 59.

FIG. 60 is an exploded view of the assembly 3000. The female cap 3002 can include a housing 3010 into which an antiseptic reservoir or pad 3032 is received. The male cap 3004 can include a housing 3050 into which a resilient support 3077, an antiseptic reservoir or pad 3070, and a sealing member 3090 are received. As further discussed below, the resilient support 3077 and the pad 3070 may be considered as a multi-part biasing member 3076 that is configured to urge the sealing member 3090 toward a proximal end of the male cap 3004. As previously mentioned, the terms "proximal" and "distal," when used herein relative to a cap, are used relative to the coupling of the cap with a medical device, such that the medical device is inserted into a proximal end of the cap and advanced toward a distal end of the cap. Accordingly, in the illustrated embodiment, the proximal ends of the caps 3002, 3004 are directed toward each other and the distal ends of the caps 3002, 3004 are directed away from each other when the assembly 3000 is in the pre-use configuration. The female cap 3002 can define one or more recesses 3016 and the male cap 3004 can define one or more recesses 3062 at positions that are between the proximal and distal ends of the caps 3002, 3004, respectively.

The sleeve 3091 can include end surfaces or edges 3096, 3098 that are configured to interact with the male and female caps 3004, 3002, respectively. The sleeve 3091 can define one or more protrusions 3099 that are configured to be received in the one or more recesses 3016 of the female cap 3002. Each protrusion 3099/recess 3016 pair can cooperate as a decoupling feature, release mechanism, or separation assist 3007. Similarly, the sleeve 3091 can define one or more protrusions 3097 that are configured to be received in the one or more recesses 3062 of the male cap 3004. Each protrusion 3097/recess 3062 pair can cooperate as a separation assist 3008. The protrusions 3097, 3099 and recesses 3016, 3062 can have rounded edges (e.g., rounded or radiused valleys and apexes), which can facilitate their rotational movement relative to one another.

As shown in FIG. 61, each protrusion 3099 can include a portion of the edge 3098 of the sleeve 3091. Moreover, each protrusion 3099 can define a pair of faces 3099a, 3099b that are angled in opposite directions. Here, the term "angled" refers to any suitable non-zero, non-180-degree angle relative to a transverse cross-sectional plane (not shown) that passes perpendicularly through a central axis of the sleeve 3091. For a path that is traced along the edge 3098 in a clockwise direction (when looking toward the edge 3098), the path moves away from the longitudinal center of the sleeve 3091 along the faces 3099a, and the path moves toward the longitudinal center of the sleeve 3091 along the faces 3099b.

Similarly, each protrusion 3097 can include a portion of the edge 3096 of the sleeve 3091, and each protrusion 3097 can define a pair of oppositely angled faces 3097a, 3097b. For a path that is traced along the edge 3096 in a clockwise direction (when looking toward the edge 3096), the path moves away from the longitudinal center of the sleeve 3091 along the faces 3097a, and the path moves toward the longitudinal center of the sleeve along the faces 3097b.

The protrusions 3097, 3099 can be relatively flexible, as they extend a greater distance from the longitudinal center of the sleeve 3091, and thus define longer moment arms relative thereto. In some embodiments, the sleeve 3091 includes a central band or reinforcing rib 3088 that can provide structural integrity to the sleeve 3091 and can prevent or inhibit large deformations of the sleeve 3091 during use and/or crushing of the sleeve 3091 after removal of one or more of the caps 3002, 3004 therefrom. The illustrated reinforcing rib 3088 projects radially inwardly at a central region of the sleeve 3091. In other embodiments, the reinforcing rib 3088 may extend outwardly or may be omitted. For example, in some embodiments, the sleeve 3091 may define a uniform thickness along its full length.

The sleeve 3091 defines an external surface 3082 and an internal surface 3083, each of which extends away from the edges 3096, 3098. The internal surface 3083 can define a cavity, opening, or lumen 3084 into which proximal ends of the male and female caps 3004, 3002 can be received. The terms "external surface" and "internal surface" are used relative to the assembly 3000 when it is in the pre-use state (e.g., the configuration shown in FIG. 59). Accordingly, when the assembly 3000 is in an assembled state, the internal surface 3083 is at an interior of the assembly 3000, so as not to be exposed to an environment that surrounds the assembly 3000, and the external surface 3083 is at an exterior of the assembly, such that it is exposed to the environment and may be grasped or otherwise contacted by a user. It is noted that in the foregoing portion of the present specification, the terms "interior" and "exterior" may at times be used with respect to inwardly directed surfaces and outwardly directed surfaces of certain caps, without regard to whether any portion of these surfaces is in fact internal to an assembly that includes these caps when the assembly is in the pre-use state. The internal surface 3083 of the sleeve 3091 also can define a connection interface 3093 (FIG. 61) and a connection interface 3095 by which the caps 3004, 3002, respectively, can be coupled to the sleeve 3091, as discussed further below.

With reference to FIGS. 62A-62C and 64, the housing 3010 of the female cap 3002 can extend between a closed distal end and an open proximal end. The closed distal end does not permit any fluid flow therethrough and serves as a barrier between an interior of the housing 3010 and an exterior environment. The open proximal end of the housing 3010 is configured to receive at least a portion of a medical connector therein, such as any of the medical connectors described above with respect to female caps. The housing 3010 can include a sidewall 3012, which defines the open proximal end, and a base wall 3013, which defines at least a portion of the closed distal end.

The housing 3010 can include a body region 3036 near a proximal end thereof, which is substantially cylindrically shaped in the illustrated embodiment. A handle 3037 can extend from the body region 3036 so as to be positioned at the distal end of the cap 3002. The handle 3037 can comprise any suitable gripping features 3003, such as any of the gripping features 103 discussed above. In the illustrated embodiment, the gripping features 3003 comprise opposing gripping regions or grasping platforms 3038 that are configured to provide a convenient surface against which a user can press so as to hold and/or twist the cap 3002.

As shown in FIG. 62B, the illustrated grasping platforms 3038 are mirrored about a longitudinal plane LP that extends along a central longitudinal axis A (shown in FIG. 62A) of the housing 3010. Each grasping platform 3038 angles radially inwardly from the body region 3036 toward the longitudinal plane LP, in a proximal-to-distal direction. The grasping platforms 3038 are more steeply angled at their proximal ends than they are at their distal ends. The angled platforms 3038, and particularly the steeply angled portions thereof, provide convenient surfaces to which forces may be applied in a distal-to-proximal direction. In the illustrated embodiment, the platforms 3038 define two substantially planar regions that are smoothly joined to each other at a rounded transition. The platforms 3038 can define a contour that is substantially complementary to fingertips that are pointed in the proximal direction.

As shown in FIG. 62A, the illustrated grasping platforms 3038 also taper inwardly toward the central longitudinal axis A of the housing 3010 in a proximal-to-distal direction. In the elevation view that is shown, the platforms 3038 are substantially ovoid. The platforms 3038 are sized and shaped to be held between the fingertips of a thumb and another finger (e.g., the index finger) of a user, although other grasping configurations may also be efficiently employed with the illustrated arrangement. The platforms 3038 provide convenient surfaces to which torque may be applied so as to rotate the cap 3002 about the longitudinal axis A.

With reference to FIGS. 62A-62C, the cap 3002 can include a lip, rim, or flange 3015 that extends radially inwardly at a proximal end of the body region 3036. The flange 3015 can contact the edge 3098 of the sleeve 3091 to prevent the cap 3002 from being inserted into the sleeve 3091 too deeply. The flange 3015 can define the one or more recesses 3016 mentioned above.

With reference again to FIG. 62B, each recess 3016 can be at least partially defined by a pair of faces 3016a, 3016b of the flange 3015 that are angled in opposite directions. The angles can be any suitable non-zero, non-180-degree angles relative to a transverse cross-sectional plane TP that passes perpendicularly through the a central axis A of the housing 3010. In particular, the faces 3016a can define an angle .alpha. relative to the transverse plane TP, and the faces 3016b can define an angle .beta. relative to the transverse plane TP. In the illustrated embodiment, the angles .alpha., .beta. are the same, although other arrangements are possible (as discussed further below). For a path is traced along the flange 3015 in a clockwise direction (when looking toward the flange 3015), the path moves proximally along the faces 3016a and the path moves distally along the faces 3016b. The faces 3016a, 3016b can be substantially planar over at least a portion thereof, and can be configured to complementarily contact the faces 3099a, 3099b, respectively, of the sleeve 3091. Additional discussion of the faces 3016a, 3016b is provided below with respect to FIGS. 65A-65B.

The housing 3010 defines an external surface 3018 and an internal surface 3019, each of which extends away from the flange 3015. The internal surface 3019 of the cap 3002 can include an outwardly directed surface of the sidewall 3012, a proximal end 3024 of the sidewall 3012, and an inwardly directed surface of the sidewall 3012 (see FIGS. 62C and 64). The outwardly directed portion of the internal surface 3019 can define a connection interface 3040 that is configured to interact with or engage the connection interface 3095 of the sleeve 3091 so as to connect the cap 3002 to the sleeve 3091. In the illustrated embodiment, the connection interfaces 3040, 3095 couple with each other via a friction-fit engagement. For example, an inner diameter of the connection interface 3095 of the sleeve 3091 can be slightly smaller than an outer diameter of the connection interface 3040 of the cap 3002. The friction fit can be sufficiently strong to provide a fluid-tight seal between the cap 3002 and the sleeve 3091, yet can allow the cap 3002 to be removed from the sleeve 3091 via manipulation by a user (e.g., without the use of ancillary tools). The fluid-tight seal can prevent evaporative loss of antiseptic from an interior of the assembly 3000 when it is in the pre-use configuration and/or can maintain the sterility of the internal portions of the assembly 3000. In other or further embodiments, the connection interfaces 3040, 3095 can include threads and/or any other suitable attachment features. In the illustrated embodiment, a proximal portion of the connection interface 3095 includes a chamfer 3020, which can assist in centering the cap 3002 relative to the sleeve 3091 when connecting the cap 3002 to the sleeve 3091.

The proximal end 3024 of the housing 3010 (which is also a proximal end of the internal surface 3019, or more generally, of the sidewall 3012), can define a seal inhibitor 3025, such as the seal inhibitor 2825 discussed above. In particular, the seal inhibitor 3025 can include one or more contact regions 3026 and one or more venting regions 3027, such as the contact regions 2826 and the venting regions 2827 discussed above. In the illustrated embodiment, the seal inhibitor 3025 includes two contact regions 3026 that are diametrically opposite from each other, and also includes two venting regions 2827 that are diametrically opposite from each other and are angularly spaced from the contact regions. Other configurations of the seal inhibitor 3025 are also possible, such as, for example, the seal inhibitor 2625 discussed above.

Figure 64:
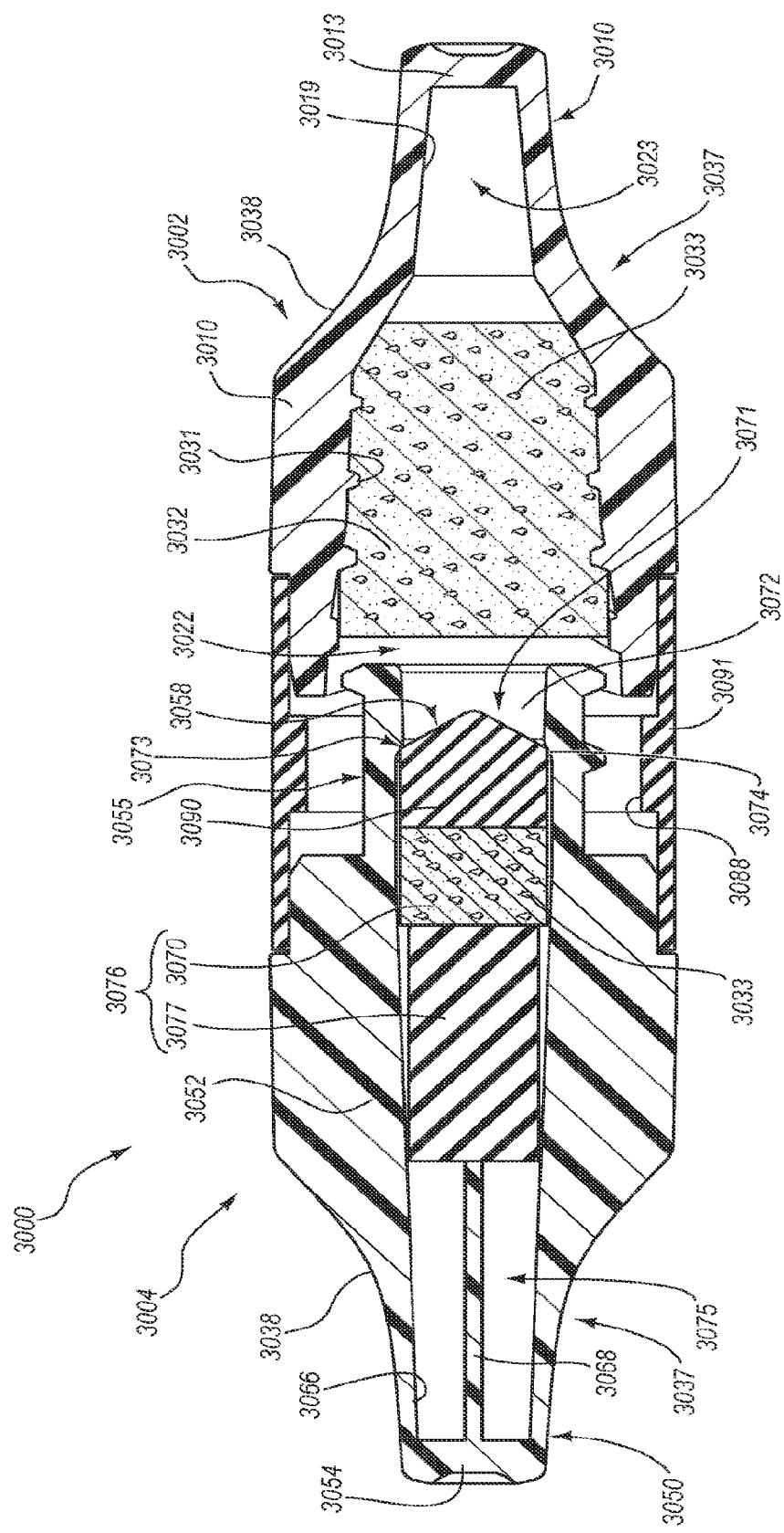
FIG. 64 is a cross-sectional view of the assembly of FIG. 59 taken along the view line 64-64 in FIG. 59.

With reference to FIGS. 62C and 64, the inwardly directed portion of the internal surface 3019 of the sidewall 3012 can define a disinfection chamber 3022, which can include a connection interface 3030. As discussed above, any suitable connection system may be used for the connection interface 3030. In the illustrated embodiment, the connection interface includes threads 3031. The connection interface 3030 can be configured to attach the cap 3002 to a medical connector in a secure yet selectively removable manner. For example, the cap 3002 can be connected in any suitable manner with any suitable medical connector, including those described above with respect to other embodiments of female caps. In other embodiments, the connection interface 3030 may include latches or prongs that are configured to snap over an outwardly extending rib of a connector, or may include one or more outwardly extending ribs over which one or more latches or prongs of the medical connector may snap.

A proximal portion of the disinfection chamber 3022 can be larger than a distal extension 3023 of the chamber. In the illustrated embodiment, the disinfection chamber 3022 defines three substantially frustoconical regions. The proximal region has a slightly tapered outer boundary that decreases in cross-sectional area in the distal direction; the intermediate region has a more pronounced tapered outer boundary that more rapidly decreases in cross-sectional area in the distal direction; and the distal region or distal extension 3023 has a slightly tapered outer boundary that decreases in cross-sectional area in the distal direction at about the same rate as the proximal region. The intermediate and distal regions correspond with the proximal and distal regions, respectively, of the grasping platforms.

The constricted intermediate region of the disinfection chamber 3022 can provide a reactive force to a distal end of the pad 3032 when the cap 3002 is secured to a medical connector. The reactive force can be sufficient to prevent the pad 3032 from being forced into the distal extension 3023. In the illustrated embodiment, the threads 3031 also provide resistive forces. Axial compression of the pad 3032 as the cap 3002 is coupled to a medical connector can swab the connector and deliver antiseptic 3033 from the pad 3032 into contact with the medical connector in manners such as described above. In some embodiments, the pad 3032 may be resiliently deformable so as to regain a pre-use shape after a medical connector is decoupled from the cap 3002. In other embodiments, the pad 3032 may instead be plastically deformable.

In the illustrated embodiment, the pad 3032 is substantially square in cross-section along its full longitudinal length when the pad 3032 is in a relaxed orientation (see FIG. 60). Such an arrangement can facilitate and/or reduce material costs associated with the manufacture of the pad 3032. At least a portion of the pad 3032 (e.g., the corners thereof) may be compressed radially when the pad 3032 is positioned within the housing 3012. Other rectangular cross-sections are also possible for the pad 3032, and in other or further embodiments, the pad 3032 may define a rectangular cross-section along only a portion of the longitudinal length thereof. In other embodiments, at least a portion of the pad 3032 may define a round cross-section, such as a circular, elliptical, or other ovoid shape. For example, the pad 3032 can be cylindrical so as to have a circular cross-section. The pad 3032 may define any other suitable shape, and may or may not be radially compressed when the assembly 3000 is in the pre-use state.

With reference to FIGS. 63A-63C, the housing 3050 of the male cap 3004 can extend between a closed distal end and an open proximal end. The closed distal end does not permit any fluid flow therethrough and serves as a barrier between an interior of the housing 3050 and an exterior environment. The open proximal end of the housing 3050 is configured to receive at least a portion of a medical connector therein. In particular, the open proximal end of the housing 3050 is sized and shaped to receive at least a portion of a male protrusion of a medical connector. For example, the open proximal end of the housing 3050 can be configured to receive at least a portion of a male luer, such as the male luer 2020 described above. The housing 3050 can include a sidewall 3052, which defines the open proximal end, and a base wall 3054, which defines at least a portion of the closed distal end.

As viewed from the exterior (e.g., in FIGS. 63A and 63B), a shape and/or configuration of the distal end of the housing 3050 can be similar or identical to the distal end of the housing 3010 of the female cap 3002, which is discussed above. For example, in the illustrated embodiment, the housing 3050 includes a body region 3036 and a handle 3037 with grasping platforms 3038, which when viewed exteriorly, are identical to the identically numbered features of the cap 3002. Accordingly, as can be seen in FIGS. 59 and 64, when the assembly 3000 is in the pre-use state, an exterior thereof can be symmetrical about three mutually perpendicular planes. Other arrangements are also possible.

With continued reference to FIGS. 63A-63C, the housing 3050 can include a lip, rim, or flange 3061 that extends radially inwardly at a proximal end of the body region 3036. The flange 3061 can contact the edge 3096 of the sleeve 3091 to prevent the cap 3004 from being inserted into the sleeve 3091 too deeply. The flange 3061 can define the one or more recesses 3062 mentioned above.

With reference to FIG. 63B, each recess 3062 can be at least partially defined by a pair of faces 3062a, 3062b of the flange 3061 that are angled in opposite directions. The angles can be any suitable non-zero, non-180-degree angles relative to a transverse cross-sectional plane TP that passes perpendicularly through the a central axis of the cap 3004. In particular, the faces 3062a can define an angle .alpha.' relative to the transverse plane TP, and the faces 3062b can define an angle .beta.' relative to the transverse plane TP. In the illustrated embodiment, the angles .alpha.', .beta.' are the same, although other arrangements are possible (as discussed further below). Moreover, in the illustrated embodiment, the angles .alpha.', .beta.' are identical to the angles .alpha., .beta. defined by the faces 3016a, 3016b of the cap 3002. For a path is traced along the flange 3061 in a clockwise direction (when looking toward the flange 3061), the path moves proximally along the faces 3016a and the path moves distally along the faces 3016b. The faces 3016a, 3016b can be substantially planar over at least a portion thereof, and can be configured to complementarily contact the faces 3097a, 3097b, respectively, of the sleeve 3091.

The male cap 3004 defines an external surface 3065 and an internal surface 3066, each of which extends away from the flange 3061. The internal surface 3066 of the cap 3004 can include an outwardly directed surface of the sidewall 3052, a proximal end of the sidewall 3052, and an inwardly directed surface of the sidewall 3052 (see FIGS. 63C and 64). The outwardly directed portion of the internal surface 3066 can define a connection interface 3080 that is configured to interact with or engage the connection interface 3093 of the sleeve 3091 so as to connect the cap 3004 to the sleeve 3091. The connection interfaces 3080, 3093 can resemble the connection interfaces 3040, 3095 discussed above. In addition, a portion of the sidewall 3052 that is at a proximal end of the connection interface 3080 can include a chamfer 3067, which can assist in centering the cap 3004 relative to the sleeve 3091 during connection of these components.

The sidewall 3052 of the cap 3004 can define an extension, elongated portion, or projection 3055 that extends proximally from the connection interface 3080. The projection 3055 can be configured to couple with a medical connector that includes a male protrusion. The projection 3055 includes a connection interface 3042 that is configured to effect the coupling. In the illustrated embodiment, the projection 3055 is substantially cylindrical, and the connection interface 3042 comprises one or more threads 3043 that are positioned at an outwardly facing surface of the cylinder. Any other suitable connection interface 3042, such as any of those described above, is possible. As shown in FIG. 64, when the assembly 3000 is in the pre-use state, a proximal end of the projection 3055 can extend into a proximal end of the disinfection chamber 3022 of the female cap 3022 in a manner such as described above with respect to the assembly 2600. In the illustrated embodiment, the reinforcement rib 3088 of the sleeve 3091 can be at a longitudinal center of the assembly 3000, and the projection 3055 can extend through the reinforcement rib 3088.

With reference to FIGS. 63C and 64, an inwardly directed portion of the internal surface 3066 of the sidewall 3052 can define a disinfection chamber 3058, which can extend from the proximal end of the projection 3055 (i.e., the open proximal end of the cap 3004) to the base wall 3054. A proximal portion of the disinfection chamber 3058 can include a proximal seal region 3071, which can be configured to form a fluid-tight seal with the male protrusion portion of a medical connector. For example, the seal region 3071 may be shaped complementarily to an outer surface of a male protrusion of a medical connector with which the male cap 3004 is configured to be used. In the illustrated embodiment, the proximal seal region 3071 comprises a substantially frustoconical surface 3072 that complies with ISO luer standards, as discussed above, such that a portion of a male luer can form a seal with the seal region 3071. The frustoconical surface 3072 can be tapered so as to decrease in diameter in a distal direction. In other embodiments, the proximal portion of the disinfection chamber 3058 may not be configured to form a fluid-tight seal with a male protrusion of a medical connector.

The disinfection chamber 3058 can further include an intermediate seal region 3073. In the illustrated embodiment, the intermediate seal region is formed by a rim, ridge, lip, or shelf 3074, which is defined by a short, substantially frustoconical portion of the sidewall 1052 that increases in diameter in the distal direction. An outer edge of a proximal surface of the sealing member 3090 can define a greater outer diameter than a minimum inner diameter of the shelf 3074 such that the shelf 3074 can maintain the sealing member 3090 within the chamber 3058. The shelf 3074 also can cooperate with the sealing member 3090 to seal the chamber 3058 when the assembly 3000 is in the pre-use state, as further discussed below.

In the illustrated embodiment, a long distal extension 3075 of the disinfection chamber 3022 can extend distally from the shelf 3074. The distal extension 3023 has a slightly tapered outer boundary that gradually decreases in cross-sectional area in the distal direction. The disinfection chamber 3022 can include a support post 3068 within a distal region thereof. The support post 3068 can be integrally formed with both the base wall 3054 and the sidewall 3052, and can provide a rigid surface against which the resilient support 3077 can rest. The support post 3068 can act as a stop that prevents the resilient support 3077 from moving distally within the chamber 3022 past a proximal end of the support post 3068. In some instances, however, a distal portion of the resilient support 3077 may deform so as to extend distally slightly past the proximal end of the support post 3068 when a medical connector is coupled with the cap 3004. The support post 3068 can reduce the amount of material that might otherwise be used to form the handle 3037 portion of the cap 3004.

The resilient support 3077, which may also be referred to as a post or a base element, can be configured to provide a base against which the antiseptic reservoir or pad 3070 can be compressed so as to force antiseptic 3033 therefrom. Accordingly, the resilient support 3077 can be harder, stiffer, or less compliant than the pad 3070, and can be configured to compress, under a given force, to a smaller extent than the pad 3070 does under the same force. For example, in various embodiments, the resilient support 3077 can be no less than about 2, 3, or 4 times harder than the pad 3070.

The resilient support 3077 can be elastically deformable such that compression of the support 3077 from a relaxed orientation gives rise to a restorative force. The resilient support 3077 can naturally return to the relaxed orientation upon removal of the compressive force. The resilient support 3077 can comprise any suitable elastically deformable material. In some embodiments, the resilient support 3077 comprises an elastomeric material, such as silicone. In certain embodiments, the resilient support 3077 comprises a closed configuration (e.g., closed cell foam) or is otherwise nonabsorbent such that little or no antiseptic 3033 that is expelled from the pad 3070 is received into the resilient support 3077. In other or further embodiments, the resilient support 3077 may comprise a spring (e.g., a compression coil spring).

In the illustrated embodiment, a distal end of the resilient support 3077 seats snugly against the inner surface 3066 of the sidewall 3052. The resilient support 3077 may form a fluid-tight seal with the sidewall 3052, which may prevent antiseptic 3033 that is expelled from the pad 3070 from migrating into the distal regions of the disinfecting chamber 3058. Rather, the antiseptic 3033 can be restrained to the proximal regions of the disinfecting chamber 3058 where it can be urged into contact with a male protrusion of a medical connector.

The pad 3070 can comprise any suitable material, such as those described above with respect to other pads (including plastically deformable materials, in some instances), and may be elastically or resiliently deformable. In some embodiments, the pad 3070 is attached to the resilient support 3077 via any suitable adhesive or other attachment mechanism, although in other embodiments, no such attachment mechanisms are used. For example, the pad 3070 and the resilient support 3077 may be maintained in contact with each other due to a slight longitudinal compression of one or more of these components once the cap 3004 is assembled (e.g., once the support 3077, the pad 3070, and the sealing member 3090 are positioned between the support post 3068 and the shelf 3074). Similarly, the pad 3070 may be attached to the sealing member 3090, or it may maintain a substantially fixed orientation relative to the sealing member 3090 without such attachment due to the resilience of the pad 3070 and/or the support 3077, which are in a slightly compressed state.

In the illustrated embodiment, the pad 3070 is substantially square in cross-section along its full longitudinal length when the pad 3070 is in a relaxed orientation (see FIG. 60). Such an arrangement can facilitate and/or reduce material costs associated with the manufacture of the pad 3070. At least a portion of the pad 3070 (e.g., the corners thereof) may be compressed radially when the pad 3070 is positioned within the housing 3052. Other rectangular cross-sections are also possible for the pad 3070, and in other or further embodiments, the pad 3070 may define a rectangular cross-section along only a portion of the longitudinal length thereof. In other embodiments, at least a portion of the pad 3070 may define a round cross-section, such as a circular, elliptical, or other ovoid shape. For example, the pad 3070 can be cylindrical so as to have a circular cross-section. The pad 3070 may define any other suitable shape, and may or may not be radially compressed when the assembly 3000 is in the pre-use state.

As previously mentioned, the pad 3070 and the support 3077 can, in some embodiments, cooperate as a two-part biasing member 3076. It is to be understood that any other suitable biasing member 3076 may be used, such as those described above. The biasing member 3076 can urge the sealing member 3090 in the proximal direction into sealing contact with the shelf 3074. The seal thus formed may be fluid-tight, and may prevent antiseptic 3033, whether in liquid or vapor form, from exiting the disinfecting chamber 3058 through the proximal end of the cap 3004 prior to coupling of the cap 3004 to a medical connector. This proximal seal may be in place when the assembly 3000 is in the pre-use configuration, as well as after the separation of the male and female caps 3004, 3002 when the assembly 3000 is opened.

Figure 66A:
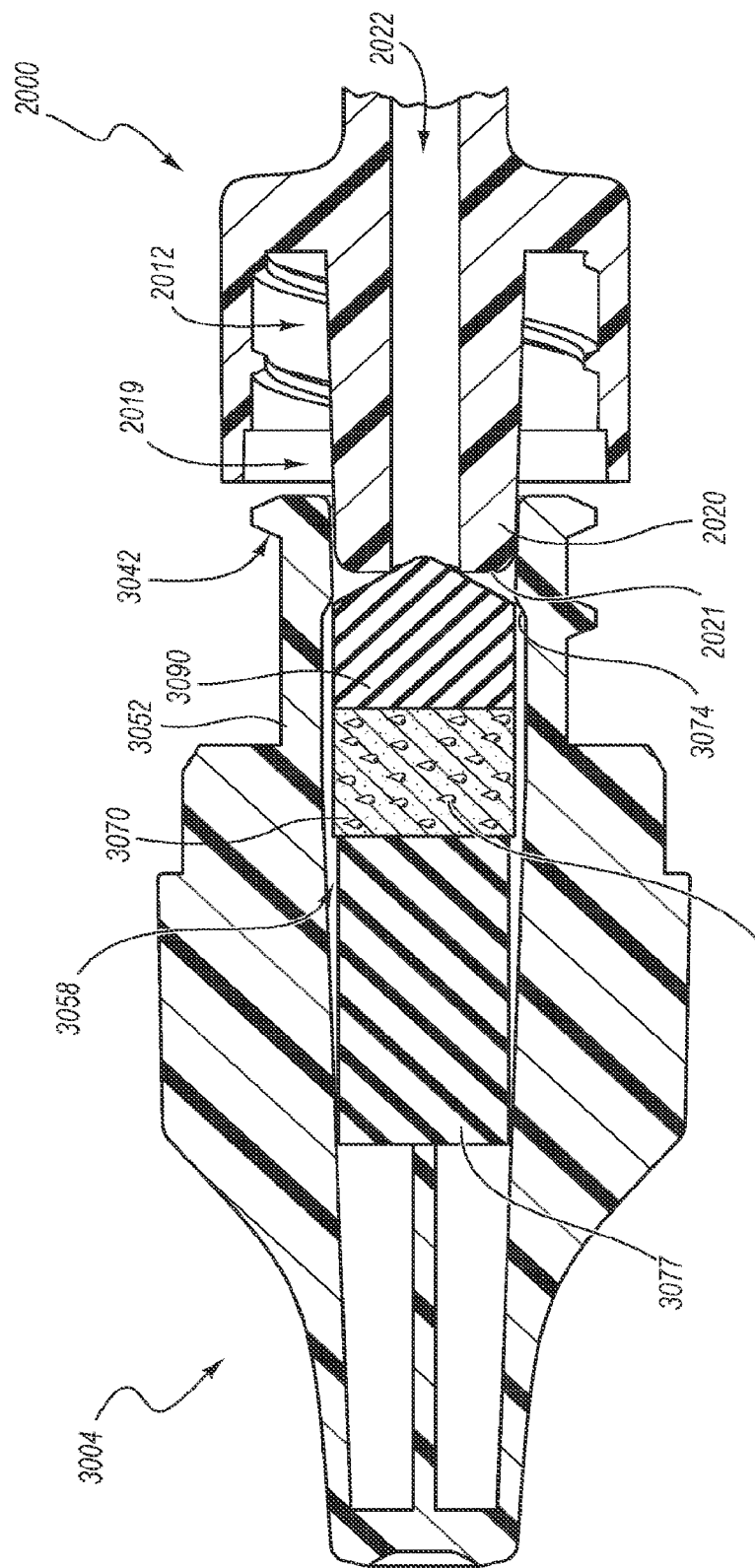
FIGS. 66A-66D depict various stages of an illustrative method for coupling a medical connector with the male cap of FIG. 65B.

The illustrated sealing member 3090 comprises unitary piece of material that includes a cylindrical region and a conical region. The conical region can be well-suited to form a seal with a tip of the projection of a male medical connector in manners such as described above. In some instances, an apex of the conical region can be received within a lumen 2022 of a luer 2020 when a medical connector is coupled with the cap 3004 (see, e.g., FIG. 66A). The sealing member 3090 can be formed of any suitable material, such as, for example, silicone and/or any of the materials discussed above with respect to other seals. In some embodiments, the sealing member 3090 can be harder, more rigid, and/or less compliant than the pad 3070.

FIGS. 65A and 65B illustrate stages in a method of removing the male cap 3004 from the assembly 3000. In some embodiments, it can be particularly advantageous to use the separation assists 3008 in the removal process. For example, in some instances, the fluid-tight seal between the cap 3004 and the sleeve 3091 can be relatively tight and/or a slight vacuum may be present within the assembly 3000 (and/or may arise as the cap 3004 is removed from the assembly 3000), such that the separation assists 3008 can facilitate removal of the cap 3004.

FIG. 65A illustrates the assembly 3000 in the pre-use state, with the faces 3062a, 3097a and 3062b, 3097b of the surfaces 3061, 3096 in contact with each other. Each paired set of surfaces constitutes a separation assist 3008. In the illustrated embodiment the assembly 3000 includes four separation assists 3008 rotationally spaced from each other at intervals of approximately 90 degrees. Focusing now on the upper separation assist 3008 that includes the faces 3062b, 3097b, the face 3062b can define an angle .beta.' (see FIG. 63B) of about 20 degrees. The face 3097b of the sleeve 3091 is at the same angle, although oppositely directed.

In order to separate the cap 3004 from the sleeve 3091, the cap 3004 can be rotated relative the sleeve 3091. In the illustrated embodiment, the cap 3004 is rotated counterclockwise, which can cause the faces 3062b, 3097b to interact with each other and slide past each other. The cap 3004 thus cams relative to the sleeve 3091 as the rotational motion is converted into translational movement of the cap 3004 away from the sleeve 3091, as shown by the arrow in FIG. 65B.

Where the angles .alpha.', .beta.' (see FIG. 63B) of the surfaces 3062a, 3062b are identical, the same mechanical advantage may be present whether the cap 3004 is rotated in the clockwise or counterclockwise directions. In other embodiments, the separation assists 3008 can be configured to aid in separating the cap 3004 from the sleeve 3091 only when the cap 3004 is rotated in one predetermined direction (e.g., either clockwise or counterclockwise). For example, the pair of faces 3062a or the pair of faces 3062b may define an angle .alpha.' or .beta.', respectively, of 20 degrees so as to allow separation as shown in FIG. 63B, whereas the other pair of faces 3062a, 3062b may be at an angle of about 90 degrees (i.e., approximately parallel to or extending through a central axis of the cap 3004) so as to prevent rotation and separation of the cap 3004. In other embodiments, one or more of the faces 3062a, 3062b may be at larger or smaller angles .alpha.', .beta.'. For example, one or more of the angles .alpha.', .beta.' may be no more than about 15, 20, 30, 45, 60, or 75 degrees or no less than about 15, 20, 30, 45, 60, or 75 degrees. Other configurations of the separation assists 3008 are also possible. For example, in some embodiments, the complementary surfaces of the recess 3062 and the protrusion 3099 can define angles as just described, but the surfaces may be rounded or otherwise non-planar.

The foregoing discussion regarding the separation assists 3008 applies equally to the separation assists 3007. In the illustrated embodiment, the separation assists 3007, 3008 are substantially identical. The sleeve 3091 may be reversible, as either end thereof may connect with either cap 3002, 3004. In other embodiments, the arrangements of the separation assists 3007, 3008 may be different from each other. For example, the planar surfaces of the separation assist 3007 may be at a larger or smaller angle than those of the separation assist 3008 so as to provide a different amount of separation force. Moreover, in some embodiments, the assembly 3000 includes a number of separation assists 3007 equal to the number of separation assists 3008, whereas in other embodiments, the assembly 3000 may include more or fewer separation assists 3007 as compared with the number of separation assists 3008. Other arrangements of the separation assists 3007, 3008 are contemplated, including those discussed above with respect to the assembly 2700. Other embodiments may be devoid of the separation assists 3007, 3008. Moreover, in some instances, a user may remove one or more of the caps 3002, 3004 from the assembly 3000 in a substantially longitudinal direction only (e.g., without rotating the caps 3002, 3004 relative to each other).

FIGS. 66A-66D illustrate consecutive stages of the cap 3004 being coupled with a medical device 2000 that includes a male protrusion 2019, which in the illustrated embodiment is a male luer 2020. As mentioned above, other arrangements of the male protrusion 2019 are also contemplated. A tip 2021 of the protrusion 2019, can be received within the disinfection chamber 3058 prior to contacting the sealing member 3090. Stated otherwise, the sealing member 3090 can be recessed relative to a proximal end of the sidewall 3052 by a distance that is sufficiently great to permit at least a portion of the male luer 2020 to be received within the sidewall 3052 before the male luer contacts the sealing member 3090.

In the illustrated stage of the procedure, the luer 2020 has been advanced sufficiently far into the disinfection chamber 3058 to contact the sealing member 3090 and to form a seal therewith. The connection interface 3042 of the cap 3004 has not yet engaged a connection interface 2012 of the medical connector 2000 at this stage, and the sealing member 3090 is just beginning to move distally within the disinfection chamber 3058 so as to break the proximal seal between the sealing member 3090 and the shelf 3074.

Figure 66B:
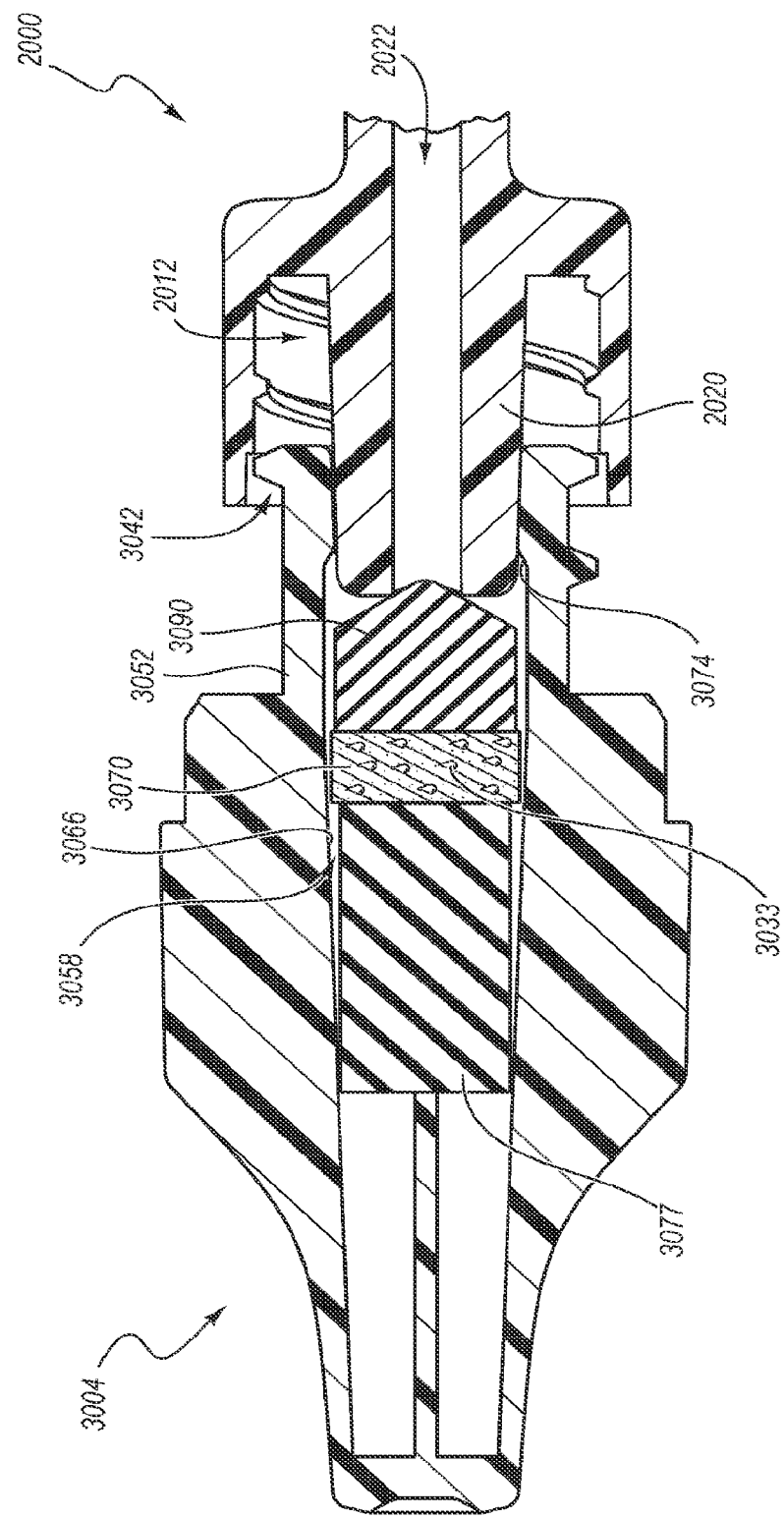

In FIG. 66B, the luer 2020 has been advanced slightly further into the disinfection chamber 3058, thereby compressing the pad 3070 somewhat and forcing antiseptic 3033 out of the pad 3070. The sealing member 3090 can define an outer diameter than is smaller than an inner diameter of this portion of the disinfection chamber 3058 such that a fluid path is present about an exterior of the sealing member 3090. Stated otherwise, the sealing member 3090 has been urged distally to a position where a periphery or outermost perimeter of the sealing member 3090 is spaced from the sidewall 3052 such that an opening, spacing, or gap that exists between the sealing member 2490 and the sidewall 2452. This opening may function as a fluid port.

Antiseptic 3033 thus can flow about the sealing member 3090 and/or any other portion of an open region that exists between the inner surface 3066 of the sidewall 3052 and the outer surfaces of the resilient support 3077, the pad 3070, the sealing member 3090, and the luer 2020. Further advancement of the luer 2020 into the disinfection chamber 3058 can cause the antiseptic 3033 to fill this open region. However, the antiseptic 3033 does not enter into the lumen 2022 of the luer 2020 due to the seal between the luer 2020 and the sealing member 3090. Further advancement of the luer 2020 into the disinfection chamber 3058 also can strengthen the seal between the luer 2020 and the sealing member 3090 due to the increasing restorative forces that arise as the pad 3070 is compressed.

As the pad 3070 is softer or more compliant than the resilient support 3077, the pad 3070 has been compressed to a much greater extent than the resilient support 3077 at this stage. Indeed, in some embodiments, the resilient support 3077 may compress only slightly or not at all at this stage.

In the illustrated embodiment, the interfaces 3042, 2012 have not yet coupled with each other at this stage. However, in other embodiments, the interfaces 3042, 2010 may already cooperate with each other at this or at a previous stage so as to draw the luer 2020 into the disinfection chamber 3058.

Figure 66C:
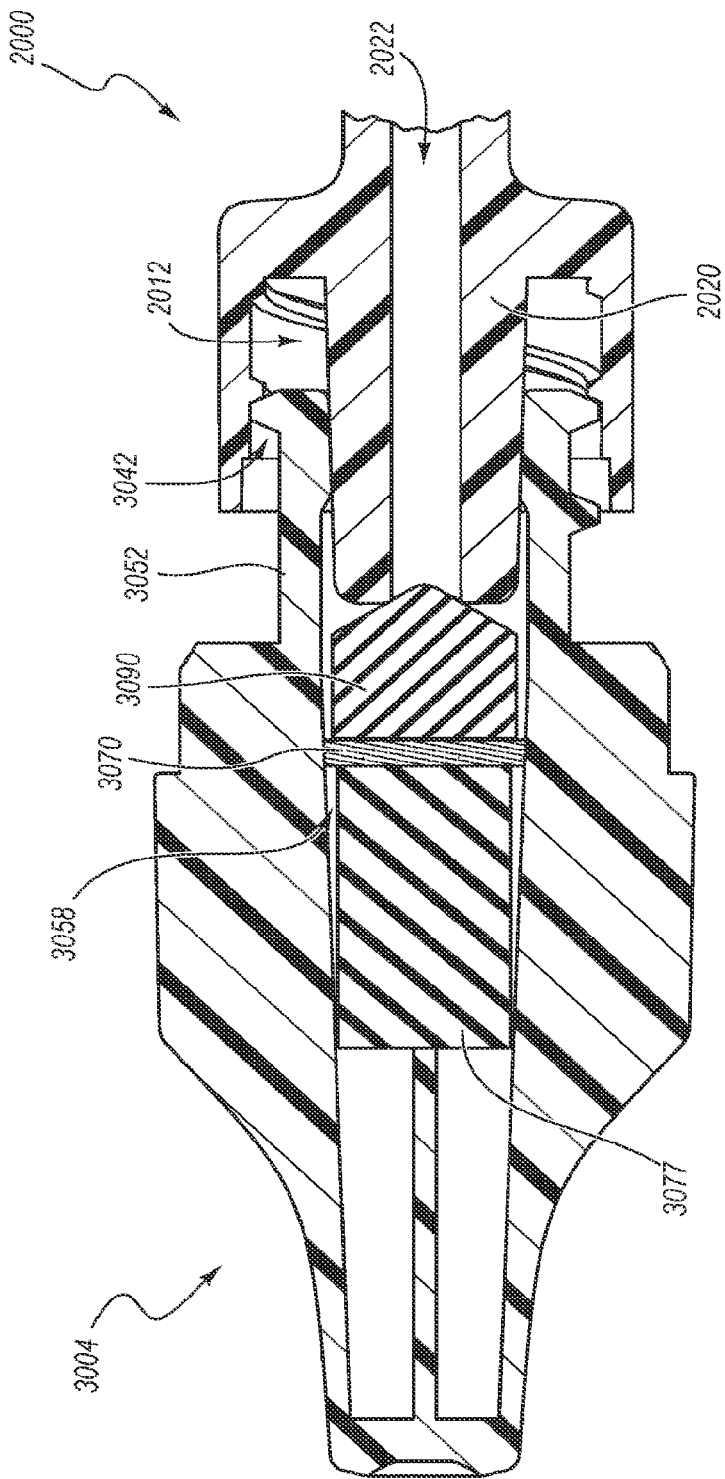

In FIG. 66C, the luer 2020 has been advanced even further into the disinfection chamber 3058, thereby compressing the pad 3070 to a greater extent and forcing additional antiseptic 3033 into the interior regions of the disinfection chamber 3058. In the illustrated embodiment, the resilient support 3077 is shown as having been slightly compressed relative to its configuration in the stage shown in FIG. 66C, whereas the pad 3070 has been nearly completely compressed, such that all or nearly all of the antiseptic 3033 has been forced therefrom. Cooperation between the connection interfaces 3042, 2012 can facilitate compression of the pad 3070 and/or the resilient support 3077.

Although the outer surface of the luer 2020 appears to be nearly parallel to and in contact with the luer-tapered surface 3072 of the sidewall 3052, a fluid-tight seal may not have formed yet in this area. Accordingly, the antiseptic 3033 may be permitted to cover the portion of the luer 2020 that is within the chamber 3058, while in some embodiments, a small portion of antiseptic 3033 may also be permitted to exit from the disinfection chamber 3058. The portion of the luer 2020 that is within the disinfection chamber 3058 thus may contact the antiseptic 3033 so as to be disinfected thereby.

Figure 66D:
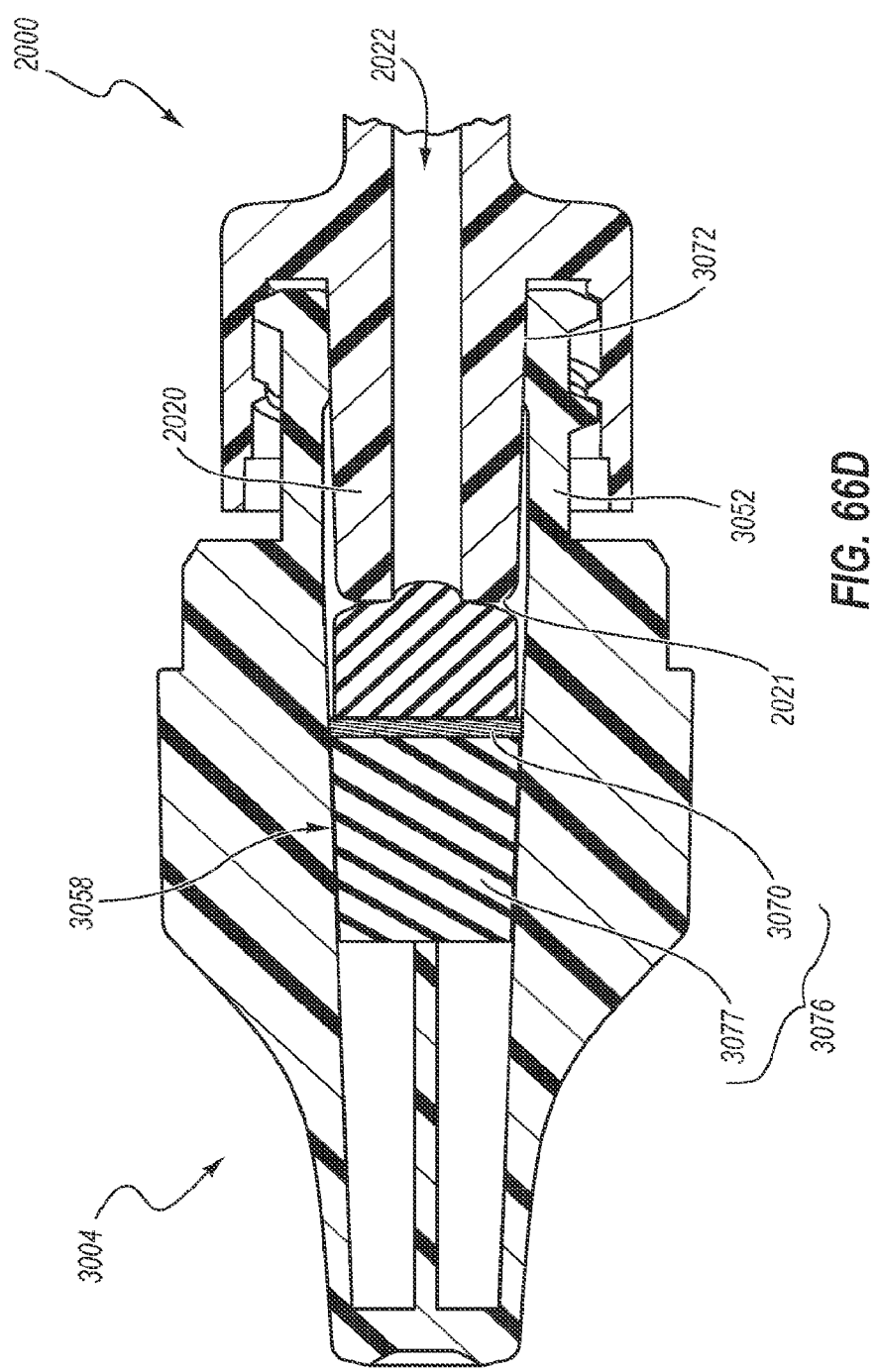

FIG. 66D illustrates a final or fully coupled stage, or an end-of-stroke orientation, in which the luer 2020 has been advanced even further into the disinfection chamber 3058 such that the luer 2020 forms a seal with the luer-tapered surface 3072 of the sidewall 3052. Antiseptic 3033 can be retained in all open portions of the disinfection chamber 3058 that are between the seal formed by the luer 2020 and the sealing member 3090 and the seal formed by the luer 2020 and the sidewall 3052. In the illustrated embodiment, a relatively large portion of the luer 2020, which includes all or most of the tip 2021, is in continual contact with the portion of the antiseptic 3033 thus retained. This portion of the luer 2020 can be bathed by the antiseptic 3033 and disinfected thereby. In other embodiments, larger portions of the luer 2020 can be bathed.

The deformable nature of the resilient support 3077 can allow for distal movement of the pad 3070, even after the pad 3070 has been fully compressed. Such an arrangement can allow for a range of acceptable lengths for the luer 2020. For example, shorter luers 2020 than that illustrated in the drawings may still be able to fully compress the pad 3070 so as to expel all antiseptic therefrom.

In other embodiments, the medical connector 2000 may include a male protrusion other than a luer 2020, such as discussed above. In some embodiments, the surface 3072 may be shaped complementarily to the outer surface of such protrusions so as to for a seal therewith. In still other embodiments, the sidewall 3052 may not form a seal with the protrusion.

When the luer 2020 is removed from the chamber 3058, the restoration forces of the pad 3070 and/or the resilient support 3077 (i.e., the biasing member 3076) can maintain the seal between the luer 2020 and the sealing member 3090, which can prevent antiseptic from entering into the lumen 2022 of the luer 2020.

Figure 67:
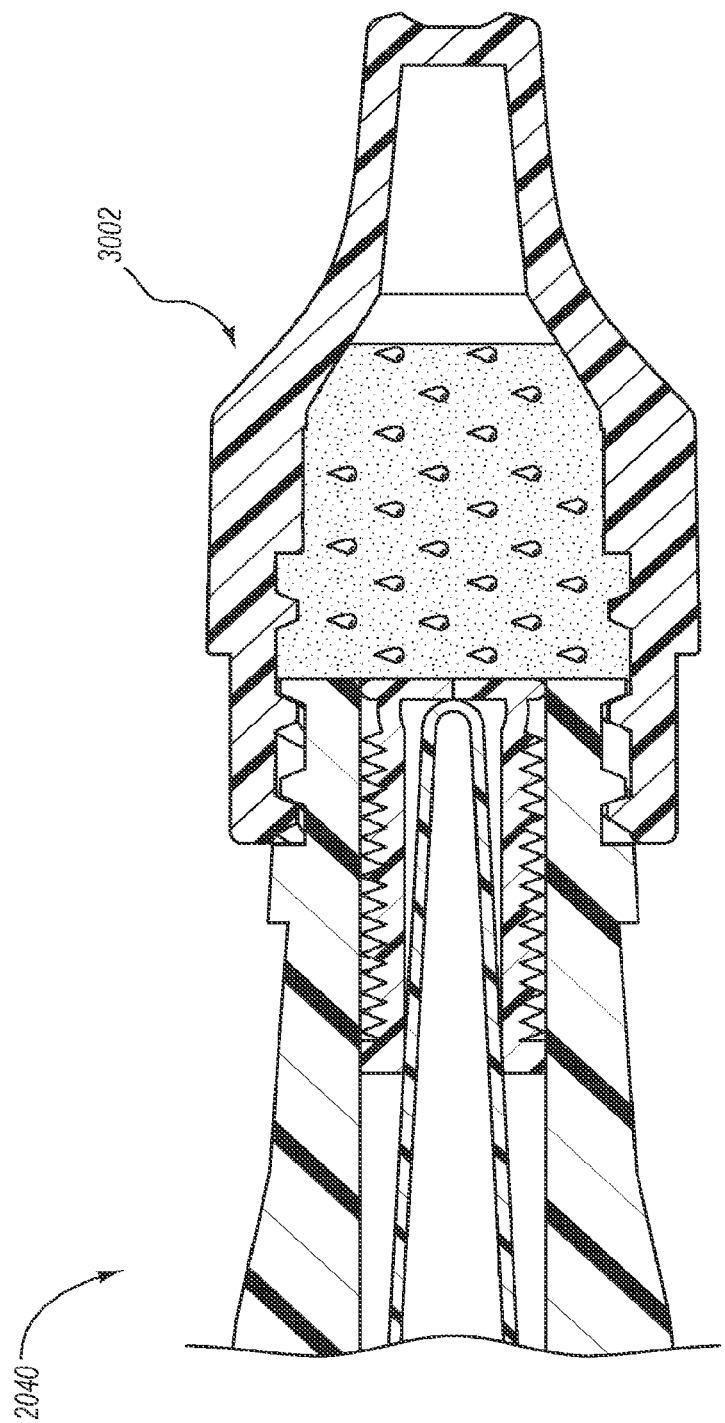
FIG. 67 is a cross-sectional view of the female cap of FIG. 64 coupled with an embodiment of a needleless injection site.
Figure 68:
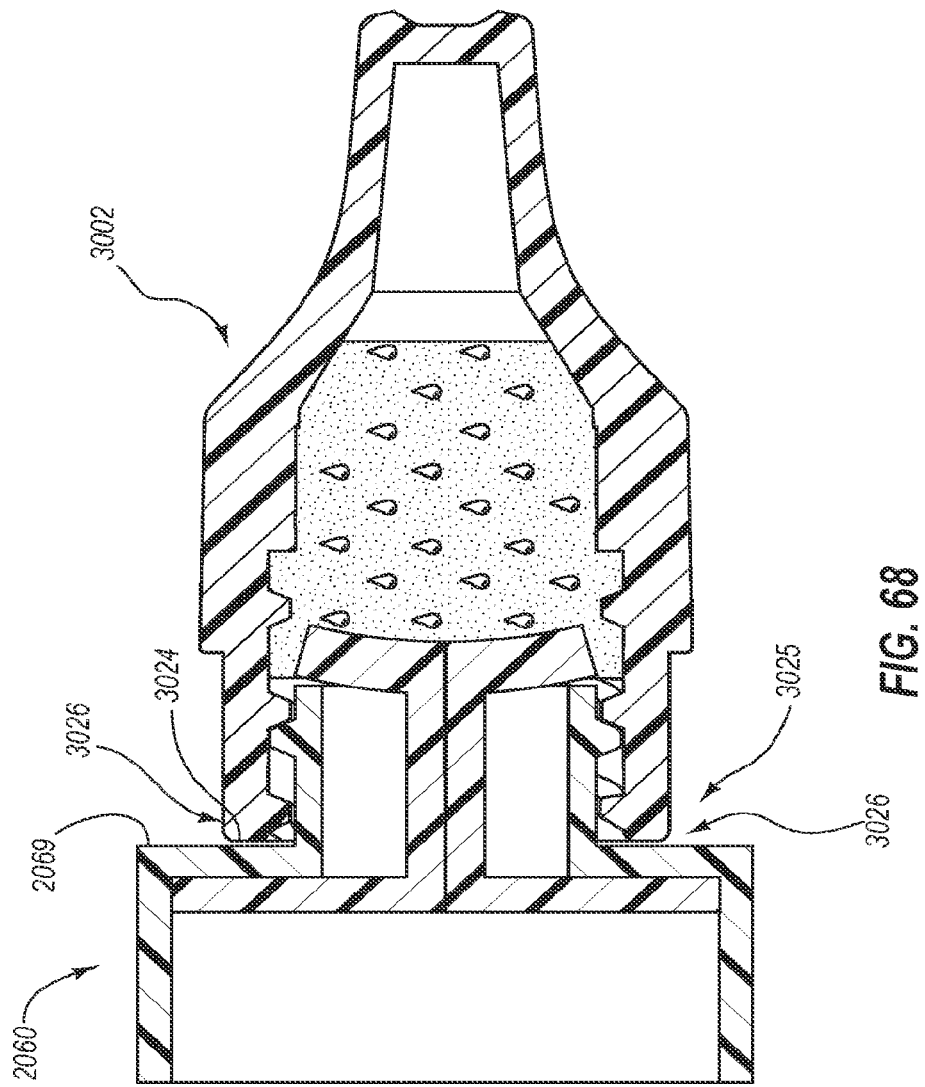
FIG. 68 is a cross-sectional view of the female cap of FIG. 64 coupled with another embodiment of a needleless injection site.
Figure 69:
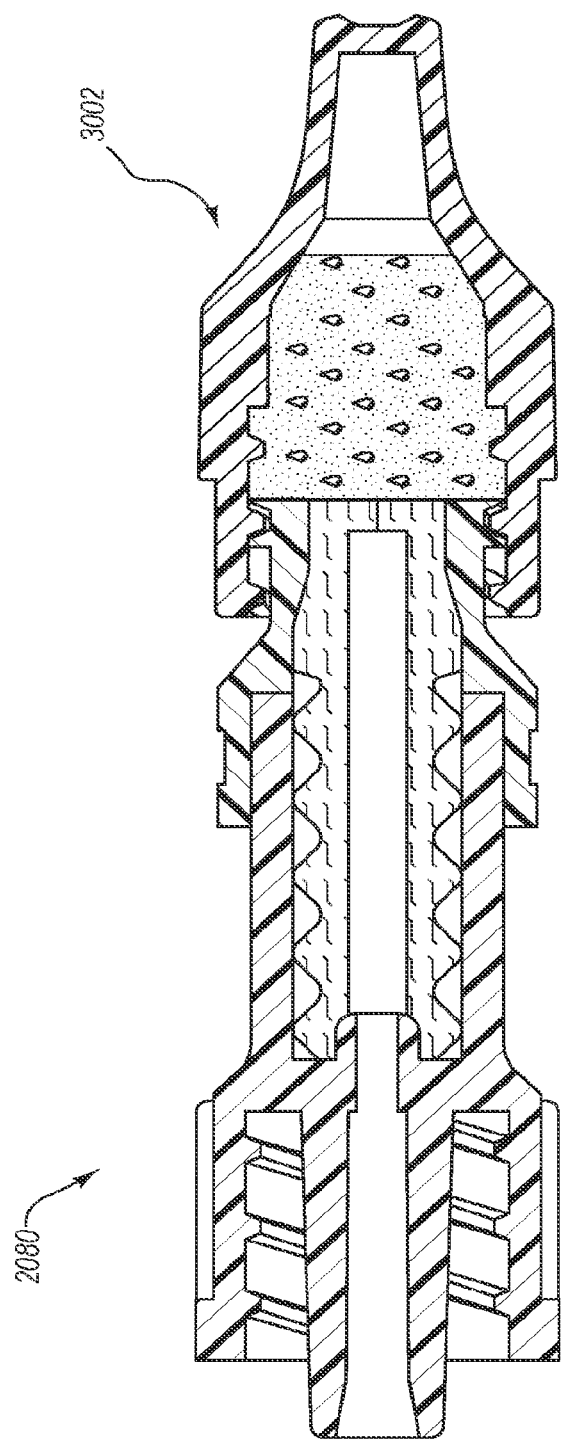
FIG. 69 is a cross-sectional view of the female cap of FIG. 64 coupled with another embodiment of a needleless injection site.

Each of FIGS. 67-69 illustrates the female cap 3002 coupled with a different needleless injection site 2040, 2060, 2080 in manners such as that described above with respect to the cap 1902 in FIGS. 32-34. More generally, the female cap 3002 can be coupled with any of a variety of different types of medical connectors in a secure fashion that disinfects each type of medical connector, such as in manners discussed above with respect to other female caps.

As shown in FIG. 68, in some arrangements, a portion of the seal inhibitor 3025 can contact an outwardly projecting surface 2069 of a needleless injection site 2060. In particular, the proximal end 3024 of the cap 3002 can contact the surface 2069 at two separate contact regions 3026 when the cap 3002 is fully coupled with the needleless injection site 2060. In the venting regions 3027 (not shown in FIG. 68, see FIGS. 62A and 62B), the proximal end 3024 of the cap 3002 can be spaced from the surface 2069.

The caps described herein, and components thereof, can be formed of, or coated with various colored materials or coatings. In some embodiments, the caps each include the same color. In other embodiments, the caps include different colors. Coloring the caps can, in some instances, provide advantages, such as ready identification of the type of cap, ready matching of a particularly colored cap with a particular type of medical connector, and the like.

The foregoing disclosure recites various embodiments that include systems configured for use with a pair of separated medical connectors. Examples of first means for coupling a male cap with a first medical connector include the connection interfaces 1042, 1142, 1342, 1542, 1842, 1942, 2242, 2342, 2642, and 3042 of the caps 1004, 1104, 1304, 1504, 1804, 1904, 2204, 2304, 2304', 2604, and 3004. Examples of first means for disinfecting a male luer of a first medical connector include the pads 1070, 1170, 1370, 1570, 1870, 2170, 2270, 2370, 2470, 2670, and 3070. Examples of second means for coupling the female cap with a second medical connector include the connection interfaces 1030, 1130, 1530, 1830, 1930, 2230, 2630, and 3030 of the caps 1002, 1102, 1502, 1802, 1902, 2202, 2602, and 3002. Examples of second means for disinfecting at least a portion of a second medical connector include the pads 1032, 1132, 1332, 1532, 1832, 2132, 2632, 3032. Examples of means for coupling the male and female caps in a pre-use configuration include the connection interfaces 1040 and 1042; 1140 and 1180; 1240 and 1280; 1340 and 1380; 1440 and 1480; 1540 and 1580; 1840 and 1891, 1842 and 1892; 2640 and 2695, 2680 and 2692; and 3040 and 3095, 3080 and 3092. Examples of means for sealing a lumen of a male luer include the sealing members 2290, 2390, 2490, 2590, 2690, and 3090. Examples of means for biasing a means for sealing a lumen of a male luer include the biasing members 2276, 2376, 2476, 2576, 2676, and 3076.

It will be understood by those having skill in the art that many changes may be made to the details of the above-described embodiments without departing from the underlying principles presented herein. For example, any suitable combination of features of the various embodiments of assemblies described above is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Recitation in the claims of the term "first" with respect to a feature or element does not necessarily imply the existence of a second or additional such feature or element. Elements recited in means-plus-function format are intended to be construed in accordance with 35 U.S.C. Sec. 112, Para. 6. It will be apparent to those having skill in the art that changes may be made to the details of the above-described embodiments without departing from the underlying principles of the invention.

We claim:

1. A male-disinfecting cap for applying an antiseptic agent to a medical male luer-lock connector of the type including a post having a lumen through which fluid flows and an internally helically threaded skirt surrounding the post, the post having a distal end with a distal-facing surface and having an inner edge formed by the distal-facing surface and the lumen, the cap comprising:
    a receiving portion defining a chamber into which the post of the male luer-lock connector can be received, the receiving portion defining an external surface, wherein the receiving portion is configured to fit within the skirt of the male luer-lock connector when the post is received into the receiving portion;
    an antiseptic agent disposed in the chamber; and
    a member movably disposed within the chamber, the member having a seal region that projects proximally and is shaped to contact just the edge of the post when the post is received into the receiving portion to diminish flow of the antiseptic agent into the lumen while permitting flow of the antiseptic agent past the member to the post of the male luer-lock connector.

2. The cap according to claim 1, further comprising means for engaging helical threads of the internally helically threaded skirt, wherein the means for engaging the helical threads are disposed on the external surface of the receiving portion.

3. The cap according to claim 1, further comprising protrusions on the external surface of the receiving portion for engaging helical threads of the internally helically threaded skirt.

4. The cap according to claim 3, further comprising a removable cover disposed over an opening of the chamber.

5. The cap according to claim 4, wherein the chamber has only a single opening.

6. The cap according to claim 5, further comprising a gripping portion.

7. The cap according to claim 6, wherein at least a portion of a wall of the chamber has a taper that narrows toward an interior of the chamber.

8. The cap according to claim 1, further comprising a removable cover disposed over an opening of the chamber.

9. The cap according to claim 1, wherein the chamber has only a single opening.

10. The cap according to claim 1, further comprising a gripping portion.

11. The cap according to claim 1, wherein at least a portion of a wall of the chamber has a taper that narrows toward an interior of the chamber.

12. A method of disinfecting a male luer-lock connector of the type including a post having a lumen through which fluid flows and an internally helically threaded skirt surrounding the post, the post having a distal end with a distal-facing surface and having an inner edge formed by the distal-facing surface and the lumen, the method comprising:
    providing a male-disinfecting cap including
        a receiving portion defining a chamber into which the post of the male luer-lock connector can be received, the receiving portion defining an external surface, wherein the receiving portion is configured to fit within the skirt of the male luer-lock connector when the post is received into the receiving portion,
        an antiseptic agent disposed in the chamber, and
        a member movably disposed within the chamber, the member having a seal region that projects proximally and is shaped to contact just the edge of the post when the post is received into the receiving portion to diminish flow of the antiseptic agent into the lumen while permitting flow of the antiseptic agent past the member to the post of the male luer-lock connector; and moving the cap in relation to the male luer-lock connector so that (i) the post is received into the chamber, (ii) the movably disposed member comes into contact with just the edge of the post, and (iii) the member covers the lumen so as to diminish flow of the antiseptic agent into the lumen while permitting flow of the antiseptic agent past the member to the post.

13. The method according to claim 12, further comprising providing the male-disinfecting cap with a cover disposed over an opening of the chamber, and removing the cover prior to the post being received into the chamber.

14. The method according to claim 13, further comprising providing the male-disinfecting cap with protrusions on the external surface of the receiving portion for engaging helical threads of the internally helically threaded skirt, and wherein moving the cap in relation to the male luer-lock connector includes twisting the cap in relation to the male luer-lock connector.

15. The method according to claim 12, further comprising providing the male-disinfecting cap with protrusions on the external surface of the receiving portion for engaging helical threads of the internally helically threaded skirt, and wherein moving the cap in relation to the male luer-lock connector includes twisting the cap in relation to the male luer-lock connector.

\* \* \* \* \*